US010435709B2

(12) United States Patent
Deisseroth et al.

(10) Patent No.: US 10,435,709 B2
(45) Date of Patent: Oct. 8, 2019

(54) DOPAMINE RECEPTOR TYPE 2 SPECIFIC PROMOTER AND METHODS OF USE THEREOF

(71) Applicant: The Board of Trustees of the Leland Stanford Junior University, Stanford, CA (US)

(72) Inventors: Karl A. Deisseroth, Stanford, CA (US); Charu Ramakrishnan, San Jose, CA (US); Kelly Zalocusky, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/531,965

(22) PCT Filed: Dec. 3, 2015

(86) PCT No.: PCT/US2015/063804
§ 371 (c)(1),
(2) Date: May 31, 2017

(87) PCT Pub. No.: WO2016/090172
PCT Pub. Date: Jun. 9, 2016

(65) Prior Publication Data
US 2017/0327841 A1    Nov. 16, 2017

Related U.S. Application Data

(60) Provisional application No. 62/087,603, filed on Dec. 4, 2014.

(51) Int. Cl.
| | |
|---|---|
| C12N 15/00 | (2006.01) |
| C12N 15/85 | (2006.01) |
| C07H 21/00 | (2006.01) |
| C07K 14/705 | (2006.01) |
| C07K 14/435 | (2006.01) |
| C12N 9/12 | (2006.01) |

(52) U.S. Cl.
CPC ........ *C12N 15/85* (2013.01); *C07K 14/43595* (2013.01); *C07K 14/70571* (2013.01); *C12N 9/1241* (2013.01); *C12N 2750/14143* (2013.01); *C12N 2830/008* (2013.01)

(58) Field of Classification Search
None
See application file for complete search history.

(56) References Cited

U.S. PATENT DOCUMENTS 6,521,814 B1 * 2/2003 Chambon .......... A01K 67/0276
435/325
2013/0317569 A1 * 11/2013 Deisseroth ........... A61N 5/0618
607/88

OTHER PUBLICATIONS

Promega, pCAT3 vector sequence, Jan. 8, 2007, pp. 1-3 (Year: 2007).*
Kozak, M. Structural Features in Eukaryotic mRNAs That Modulate the Initiation of Translation. JBC, (1991), 266:19867-19870. (Year: 1991).*
Luckow et al., CAT constructions with multiple unique restriction sites for the functional analysis of eukaryotic promoters and regulatory elements. Nucleic Acids Research, vol. 15 No. 13 1987, p. 5490. (Year: 1987).*
Cordeiro, et al.; "Association Between the DRD2-141C Insertion/Deletion Polymorphism and Schizophrenia"; Arq Neuropsiquiatr; vol. 67, vol. 2-A, pp. 191-194 (2009).
Tateno, et al.; "Differential Expression of Somatostatin and Dopamine Receptor Subtype Genes in Adrenocorticotropin (ACTH)-secreting Pituitary Tumors and Silent Corticotroph Adenomas"; Endocrine Journal; vol. 56, No. 4, pp. 579-584 (2009).
AC096118.6. GenBank Acession No. AC096118.6 Rattus norvegicus clone CH230-11B15, Working Draft Sequence, 3 unordered pieces. May 10, 2003 [online]. [Retrieved on Jan. 27, 2016]. Retrieved from website <URL: http://www.ncbi.nlm.nih.gov/nuccore/AC096118> Entire document.
Minowa, et al.; "Analysis of the Promoter Region of the Rat $D_2$ Dopamine Receptor Gene"; Biochemistry; vol. 31, No. 36, pp. 8389-8396 (1992).
Stonehouse et al. "Caffeine Regulates Neuronal Expression of the Dopamine 2 Receptor Gene"; Mal Pharmacol (2003) vol. 64, No. 6, pp. 1463-1473.
Takeuchi, et al.; "Activation of the rat dopamine D2 receptor promoter by mitogen-activated protein kinase and $Ca^{2+}$/calmodulin-dependent protein kinase II pathways"; Journal of Neurochemistry; vol. 83, pp. 784-796 (2002).
U79717.1, Genbank direct submission U79717.1, Rattus norvegicus dopamine D2 receptor gene, promoter region and exon 1. Jan. 31, 1997 [online]. [Retrieved on Feb. 4, 2016]. Retrieved from website <URL: http://www.ncbi.nlm.nih.gov/nuccore/1809138> Entire document.

* cited by examiner

*Primary Examiner* — Kevin K Hill
*Assistant Examiner* — Arthur S Leonard
(74) *Attorney, Agent, or Firm* — Bozicevic, Field & Francis LLP; Paul A. Borden; Payal B. Sud

(57) ABSTRACT

A nucleic acid containing a dopamine receptor type 2-specific promoter (D2SP) is provided. In certain embodiments, the nucleic acid includes a dopamine receptor type 2-specific promoter (D2SP), wherein the D2SP does not include exon 1 of a D2 receptor gene, wherein the D2SP comprises a Kozak sequence, and wherein the D2SP includes a nucleotide sequence having at least 95% sequence identity to the nucleotide sequence set forth in SEQ ID NO: 1. Also provided are expression vectors, genetically modified host cells and kits that include the subject nucleic acid.

26 Claims, 29 Drawing Sheets
Specification includes a Sequence Listing.

FIG. 1
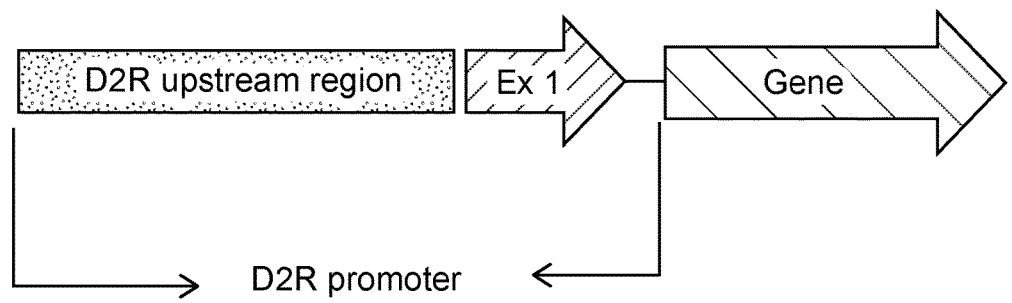
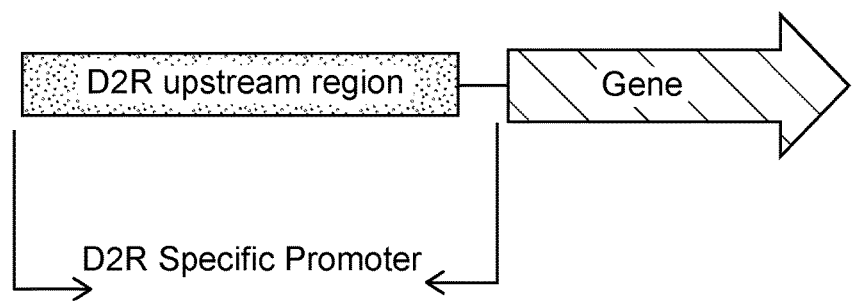

FIG. 2

```
D2SP    ttatcctcggtgcatctcagagaaataagcattgcttggaccaatgtggaccggatgtta    60
        ||||||||||||||||||||||||||||||||||||||||||||||||||||||||||||
D2R     ttatcctcggtgcatctcagagaaataagcattgcttggaccaatgtggaccggatgtta    60

D2SP    acacctagagccagagagattaaaaaatttaatcaacatctacaactggcaagggataga    120
        ||||||||||||||||||||||||||||||||||||||||||||||||||||||||||||
D2R     acacctagagccagagagattaaaaaatttaatcaacatctacaactggcaagggataga    120

D2SP    cataggacacacgactgggtggaaaacgtatagaggtgatgggttgagaagaacaaaatc    180
        ||||||||||||||||||||||||||||||||||||||||||||||||||||||||||||
D2R     cataggacacacgactgggtggaaaacgtatagaggtgatgggttgagaagaacaaaatc    180

D2SP    cctgtttaagtaggttatttcttgggaagaacatgtccagggcacataggaaaatagtgg    240
        ||||||||||||||||||||||||||||||||||||||||||||||||||||||||||||
D2R     cctgtttaagtaggttatttcttgggaagaacatgtccagggcacataggaaaatagtgg    240

D2SP    ggattcaaccatgtctgtaatgtgtgagtgccttaaaagcaaatgtgaaaaattctaatg    300
        ||||||||||||||||||||||||||||||||||||||||||||||||||||||||||||
D2R     ggattcaaccatgtctgtaatgtgtgagtgccttaaaagcaaatgtgaaaaattctaatg    300

D2SP    tttctggtagttctaacacttccctaccatgcctatagagagccatgaatagaccatacc    360
        ||||||||||||||||||||||||||||||||||||||||||||||||||||||||||||
D2R     tttctggtagttctaacacttccctaccatgcctatagagagccatgaatagaccatacc    360

D2SP    ccaagaataatgataggggaaggggaggctagttcccttttcttaaatgcctccataa     420
        ||||||||||||||||||||||||||||||||||||||||||||||||||||||||||
D2R     ccaagaataatgataggggaaggggaggctagttcccttttcttaaatgcctccataa     420

D2SP    ctggccacatctaagaaaaatgtgctgtgtatagggactgttccactgctggttccccgt    480
        ||||||||||||||||||||||||||||||||||||||||||||||||||||||||||||
D2R     ctggccacatctaagaaaaatgtgctgtgtatagggactgttccactgctggttccccgt    480

D2SP    gaggtttggaggggcatgcctctttgggtcccagattccacctttgaaatcaaacagggg    540
        ||||||||||||||||||||||||||||||||||||||||||||||||||||||||||||
D2R     gaggtttggaggggcatgcctctttgggtcccagattccacctttgaaatcaaacagggg    540

D2SP    ttagttgaatattagtgtctgtctttccaaccttaattttccaggattgtgtggatcaat    600
        ||||||||||||||||||||||||||||||||||||||||||||||||||||||||||||
D2R     ttagttgaatattagtgtctgtctttccaaccttaattttccaggattgtgtggatcaat    600

D2SP    ggaaggagtttcttctttgtggctaagtggcatgactgccggctatatgcagactgtcct    660
        ||||||||||||||||||||||||||||||||||||||||||||||||||||||||||||
D2R     ggaaggagtttcttctttgtggctaagtggcatgactgccggctatatgcagactgtcct    660

D2SP    ctgtgctcctgcccttggaattctgtggtgccttctccttggggacttgaattggccaat    720
        ||||||||||||||||||||||||||||||||||||||||||||||||||||||||||||
D2R     ctgtgctcctgcccttggaattctgtggtgccttctccttggggacttgaattggccaat    720

D2SP    ggccagctcctgtgaggtctccggagctgtcggtactccacagcacctatttaagctaca    780
        ||||||||||||||||||||||||||||||||||||||||||||||||||||||||||||
D2R     ggccagctcctgtgaggtctccggagctgtcggtactccacagcacctatttaagctaca    780

D2SP    agtatttggaagactctactctggattgaccccatgcattctgaatctcatgtagaagct    840
        ||||||||||||||||||||||||||||||||||||||||||||||||||||||||||||
D2R     agtatttggaagactctactctggattgaccccatgcattctgaatctcatgtagaagct    840

D2SP    ggccaaggcaggacagagggacagaaagcaccagctggatttgagaagaagaggatggaa    900
        ||||||||||||||||||||||||||||||||||||||||||||||||||||||||||||
D2R     ggccaaggcaggacagagggacagaaagcaccagctggatttgagaagaagaggatggaa    900
```

FIG. 2 (cont.)

```
D2SP    agggttgtaggttccctgggtgggagatgaccctggacagggctgaagaagatcacattt    960
        ||||||||||||||||||||||||||||||||||||||||||||||||||||||||||||
D2R     agggttgtaggttccctgggtgggagatgaccctggacagggctgaagaagatcacattt    960

D2SP    ctcttcctcctgctcctcagtgcagacggaagggtgagctagaattttcacggccttctt    1020
        ||||||||||||||||||||||||||||||||||||||||||||||||||||||||||||
D2R     ctcttcctcctgctcctcagtgcagacggaagggtgagctagaattttcacggccttctt    1020

D2SP    tatcattcccatcttagatctgctctgcccaagtcttcctctcagaaagcacaacagcag    1080
        ||||||||||||||||||||||||||||||||||||||||||||||||||||||||||||
D2R     tatcattcccatcttagatctgctctgcccaagtcttcctctcagaaagcacaacagcag    1080

D2SP    aacgaactgctgtgattttcagacctgaggtctgtacaccgactctggatatccttccgg    1140
        ||||||||||||||||||||||||||||||||||||||||||||||||||||||||||||
D2R     aacgaactgctgtgattttcagacctgaggtctgtacaccgactctggatatccttccgg    1140

D2SP    aatctatttctcctttaaagacttgatgtaccacacgtagtgcttcagctagcccttggc    1200
        ||||||||||||||||||||||||||||||||||||||||||||||||||||||||||||
D2R     aatctatttctcctttaaagacttgatgtaccacacgtagtgcttcagctagcccttggc    1200

D2SP    cctgactcctcaaaggaggggatcgacccgctggtgttgtgattgctagaccagagtagg    1260
        ||||||||||||||||||||||||||||||||||||||||||||||||||||||||||||
D2R     cctgactcctcaaaggaggggatcgacccgctggtgttgtgattgctagaccagagtagg    1260

D2SP    tttggatgggcagggtgttacttaaaaagtataggatgacaccggcgagcagtccggagc    1320
        ||||||||||||||||||||||||||||||||||||||||||||||||||||||||||||
D2R     tttggatgggcagggtgttacttaaaaagtataggatgacaccggcgagcagtccggagc    1320

D2SP    acaggctatccccactcaaagccagagatggattctcggtctcagctctcaaggttcctt    1380
        ||||||||||||||||||||||||||||||||||||||||||||||||||||||||||||
D2R     acaggctatccccactcaaagccagagatggattctcggtctcagctctcaaggttcctt    1380

D2SP    ccccaggccccacagtgcagagatagttctggggccctgggtgggtggggcctctgtaca    1440
        ||||||||||||||||||||||||||||||||||||||||||||||||||||||||||||
D2R     ccccaggccccacagtgcagagatagttctggggccctgggtgggtggggcctctgtaca    1440

D2SP    aggggcggggttcccgggcgcctcgtggccagggtgaccccgcccccctcctcctgcgcag    1500
        ||||||||||||||||||||||||||||||||||||||||||||||||||||||||||||
D2R     aggggcggggttcccgggcgcctcgtggccagggtgaccccgcccccctcctcctgcgcag    1500

D2SP    cgctctgattccgcggagctgtccagcctcagtgccggggggatccgccacc--------    1552
        ||||||||||||||||||||||||||||||||||||||||
D2R     cgctctgattccgcggagctgtccagcctcagtgccggggctggtcccctcttgtgcgcg    1560

D2SP    ------------------------------------------------------------    1552
D2R     gcgcctcctggccggcttcccgcctggttcccgcgctgggctcccgtcctcccgccccgc    1620

D2SP    ------------------------------------------------------------    1552
D2R     cttcgtcctgccccgccgcggccggtctactgctccccgcgggcccgagccggccgagcg    1680

D2SP    ------------------------------------------------------------    1552
D2R     gctgcccgccggggatctgaacggcgcggcggggccggaagccgagggacccgcggaggg    1740

D2SP    ------------------------------------------------------------    1552
D2R     gaccggcggccccggacggctgccggaggggcggccgtgcgtggatgcggcgggagctgg    1800

D2SP    ----------    1552
D2R     aagcctcgag    1810
```

FIG. 5
D2SP::NpHR3.0-eYFP
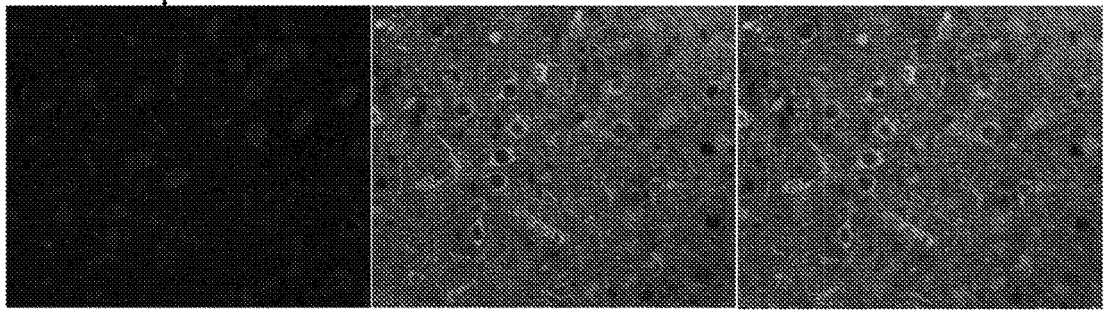
D2R::NpHR3.0-eYFP
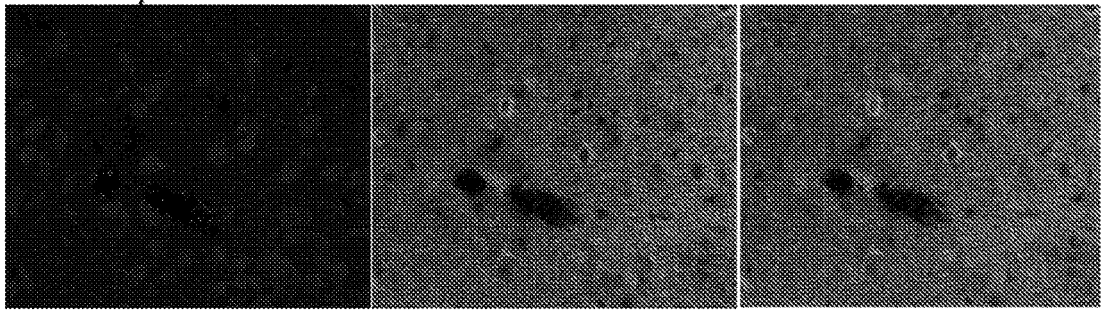

FIG. 15

Exon 1 of rat D2R (based on traditional D2R promoter sequence +
sequence information from GenBank Accession # U04330 + information
from complete mRNA Accession # NM_012547 (SEQ ID NO: 3)

ctggtcccctcttgtgcgcggcgcctcctggccggcttcccgcctggttcccgcgctgggctcccgtcct
cccgccccgccttcgtcctgccccgccgcggccggtctactgctccccgcgggcccgagccggccgagcg
gctgcccgccggggatctgaacggcgcggcggggccggaagccgagggacccgcggaggggaccggcggc
cccggacggctgccggaggggcggccgtgcgtggatgcggcgggagctggaagcctcgagcagccggcgc
cttctctggccccgggcgccatatggcttgaag

FIG. 16

(Depolarizing opsins)

Amino acid sequence of ChR2 (SEQ ID NO: 4)

MDYGGALSAVGRELLFVTNPVVVNGSVLVPEDQCYCAGWIESRGTNGAQTASNVLQWLAAGF
SILLLMFYAYQTWKSTCGWEEIYVCAIEMVKVILEFFFEFKNPSMLYLATGHRVQWLRYAEWLL
TCPVILIHLSNLTGLSNDYSRRTMGLLVSDIGTIVWGATSAMATGYVKVIFFCLGLCYGANTFFH
AAKAYIEGYHTVPKGRCRQVVTGMAWLFFVSWGMFPILFILGPEGFGVLSVYGSTVGHTIIDLM
SKNCWGLLGHYLRVLIHEHILIHGDIRKTTKLNIGGTEIEVETLVEDEAEAGAVP

Amino acid sequence of ChR2 with ER export and trafficking signal
sequences (SEQ ID NO: 5)

MDYGGALSAVGRELLFVTNPVVVNGSVLVPEDQCYCAGWIESRGTNGAQTASNVLQWLAAGF
SILLLMFYAYQTWKSTCGWEEIYVCAIEMVKVILEFFFEFKNPSMLYLATGHRVQWLRYAEWLL
TCPVILIHLSNLTGLSNDYSRRTMGLLVSDIGTIVWGATSAMATGYVKVIFFCLGLCYGANTFFH
AAKAYIEGYHTVPKGRCRQVVTGMAWLFFVSWGMFPILFILGPEGFGVLSVYGSTVGHTIIDLM
SKNCWGLLGHYLRVLIHEHILIHGDIRKTTKLNIGGTEIEVETLVEDEAEAGAVP*AAA***KSRITSEGE
YIPLDQIDINV**FCYENEV amino acid sequence of a ChR2 SSFO (SEQ ID NO: 6)

MDYGGALSAVGRELLFVTNPVVVNGSVLVPEDQCYCAGWIESRGTNGAQTASNVLQWLAAGF
SILLLMFYAYQTWKSTCGWEEIYVCAIEMVKVILEFFFEFKNPSMLYLATGHRVQWLRYAEWLL
TSPVILIHLSNLTGLSNDYSRRTMGLLVSAIGTIVWGATSAMATGYVKVIFFCLGLCYGANTFFH
AAKAYIEGYHTVPKGRCRQVVTGMAWLFFVSWGMFPILFILGPEGFGVLSVYGSTVGHTIIDLM
SKNCWGLLGHYLRVLIHEHILIHGDIRKTTKLNIGGTEIEVETLVEDEAEAGAVP amino acid sequence of a ChR2 SSFO with ER export and trafficking signal
sequences (SEQ ID NO: 7)

MDYGGALSAVGRELLFVTNPVVVNGSVLVPEDQCYCAGWIESRGTNGAQTASNVLQWLAAGF
SILLLMFYAYQTWKSTCGWEEIYVCAIEMVKVILEFFFEFKNPSMLYLATGHRVQWLRYAEWLL
TSPVILIHLSNLTGLSNDYSRRTMGLLVSAIGTIVWGATSAMATGYVKVIFFCLGLCYGANTFFH
AAKAYIEGYHTVPKGRCRQVVTGMAWLFFVSWGMFPILFILGPEGFGVLSVYGSTVGHTIIDLM
SKNCWGLLGHYLRVLIHEHILIHGDIRKTTKLNIGGTEIEVETLVEDEAEAGAVP*AAA***KSRITSEGE
YIPLDQIDINV**FCYENEV

FIG. 16 (cont.)

Amino acid sequence of a VChR1 (SEQ ID NO: 8)
Mdypvarslivryptdlgngtvcmprgqcycegwlrsrgtsiektiaitlqwvvfalsvaclgw
yayqawratcgweevyvaliemmksiieafhefdspatlwlssgngvvwmrygewlltcpvlli
hlsnltglkddyskrtmgllvsdvgcivwgatsamctgwtkilfflislsygmytyfhaakvyi
eafhtvpkgicrelvrvmawtffvawgmfpvlfllgtegfghispygsaighsildliaknmwgvl
gnylrvkihehillygdirkkqkitiagqemevetlvaeeed

Amino acid sequence of a VChR1 with ER export and trafficking signal
sequences (SEQ ID NO: 9)
Mdypvarslivryptdlgngtvcmprgqcycegwlrsrgtsiektiaitlqwvvfalsvaclgw
yayqawratcgweevyvaliemmksiieafhefdspatlwlssgngvvwmrygewlltcpvlli
hlsnltglkddyskrtmgllvsdvgcivwgatsamctgwtkilfflislsygmytyfhaakvyi
eafhtvpkgicrelvrvmawtffvawgmfpvlfllgtegfghispygsaighsildliaknmwgvl
gnylrvkihehillygdirkkqkitiagqemevetlvaeeed*AAA*KSRITSEGEYIPLDQIDINVFCY
ENEV amino acid sequence of C1V1 (SEQ ID NO: 10)

MSRRPWLLALALAVALAAGSAGASTGSDATVPVATQDGPDYVFHRAHERMLFQTSYTLENN
GSVICIPNNGQCFCLAWLKSNGTNAEKLAANILQWITFALSALCLMFYGYQTWKSTCGWEEIY
VATIEMIKFIIEYFHEFDEPAVIYSSNGNKTVWLRYAEWLLTCPVLLIHLSNLTGLKDDYSKRT
MGLLVSDVGCIVWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLGNYLRVKIHEHI
LLYGDIRKKQKITIAGQEMEVETLVAEEED amino acid sequence of C1V1 with ER export and trafficking signal sequences
(SEQ ID NO: 11)

MSRRPWLLALALAVALAAGSAGASTGSDATVPVATQDGPDYVFHRAHERMLFQTSYTLENN
GSVICIPNNGQCFCLAWLKSNGTNAEKLAANILQWITFALSALCLMFYGYQTWKSTCGWEEIY
VATIEMIKFIIEYFHEFDEPAVIYSSNGNKTVWLRYAEWLLTCPVLLIHLSNLTGLKDDYSKRT
MGLLVSDVGCIVWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLGNYLRVKIHEHI
LLYGDIRKKQKITIAGQEMEVETLVAEEED*AAA*KSRITSEGEYIPLDQIDINVFCYENEV

Amino acid sequence of a C1C2 (SEQ ID NO: 12)

MSRRPWLLALALAVALAAGSAGASTGSDATVPVATQDGPDYVFHRAHERMLFQTSYTLENNGSVICIPNN
GQCFCLAWLKSNGTNAEKLAANILQWITFALSALCLMFYGYQTWKSTCGWEEIYVATIEMIKFIIEYFHE
FDEPAVIYSSNGNKTVWLRYAEWLLTCPVILHLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
VYGSTVGHTIIDLMSKNCWGLLGHYLRVLIHEHILIHGDIRKTTKLNIGGTEIEVETLVEDEAEAGAV

FIG. 16 (cont.)

Amino acid sequence of a C1C2 with ER export and trafficking signal sequences (SEQ ID NO: 13)

MSRRPWLLALALAVALAAGSAGASTGSDATVPVATQDGPDYVFHRAHERMLFQTSYTLENNGSVICIPNN
GQCFCLAWLKSNGTNAEKLAANILQWITFALSALCLMFYGYQTWKSTCGWEEIYVATIEMIKFIIEYFHE
FDEPAVIYSSNGNKTVWLRYAEWLLTCPVILIHLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
VYGSTVGHTIIDLMSKNCWGLLGHYLRVLIHEHILIHGDIRKTTKLNIGGTEIEVETLVEDEAEAGAV*AA
A*KSRITSEGEYIPLDQIDINVFCYENEV

Amino acid sequence of ReaChR (red shifted ChR) (SEQ ID NO: 14)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVTFALSVACLGWYAYQAWRATCGWEEVYVALIEMMKSIIEAFH
EFDSPATLWLSSGNGVVWMRYGEWLLTCPVILIHLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SPYGSAIGHSILDLIAKNMWGVLGNYLRVKIHEHILLYGDIRKKQKITIAGQEMEVETLVAEEEDKYESS

Amino acid sequence of ReaChR (red shifted ChR) with ER export and trafficking signal sequences (SEQ ID NO: 15)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVTFALSVACLGWYAYQAWRATCGWEEVYVALIEMMKSIIEAFH
EFDSPATLWLSSGNGVVWMRYGEWLLTCPVILIHLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SPYGSAIGHSILDLIAKNMWGVLGNYLRVKIHEHILLYGDIRKKQKITIAGQEMEVETLVAEEEDKYESS
*AAA*KSRITSEGEYIPLDQIDINVFCYENEV

Amino acid sequence of SdChR (CheRiff) (SEQ ID NO: 16)

Mggapapdahsappgndsaggseyhapagyqvnppyhpvhgyeeqcssiyiyygalweqetargfqwfavflsalfl
afygwhaykasvgweevyvcsvelikvileiyfeftspamlflyggnitpwlryaewlltcpvilihlsnitglsee
ynkrtmallvsdlgticmgvtaalatgwvkwlfyciglvygtqtfynagiiyvesyyimpaggckklvlamtavyys
swlmfpglfifgpegmhtlsvagstightiadllskniwgllghflrikihehiimygdirrpvssqflgrkvdvla
fvteedkv

Amino acid sequence of SdChR (CheRiff) with ER export and trafficking signal sequences (SEQ ID NO: 17)

Mggapapdahsappgndsaggseyhapagyqvnppyhpvhgyeeqcssiyiyygalweqetargfqwfavflsalfl
afygwhaykasvgweevyvcsvelikvileiyfeftspamlflyggnitpwlryaewlltcpvilihlsnitglsee
ynkrtmallvsdlgticmgvtaalatgwvkwlfyciglvygtqtfynagiiyvesyyimpaggckklvlamtavyys
swlmfpglfifgpegmhtlsvagstightiadllskniwgllghflrikihehiimygdirrpvssqflgrkvdvla
fvteedkv*AAA*KSRITSEGEYIPLDQIDINVFCYENEV

FIG. 16 (cont.)

Amino acid sequence of CnChR1 (Chrimson) (SEQ ID NO: 18)

Maelissatrslfaagginpwpnpyhhedmgcggmtptgecfstewwcdpsyglsdagygycfveatggylvvgvek
kqawlhsrgtpgekigaqvcqwiafsiaialltfygfsawkatcgweevyvccvevlfvtleifkefsspatvylst
gnhayclryfewllscpviliklsnlsglkndyskrtmglivscvgmivfgmaaglatdwlkwllyivsciyggymy
fqaakcyveanhsvpkghcrmvvklmayayfaswgsypilwavgpegllklspyansighsicdiiakefwtflahh
lrikihehilihgdirktttkmeiggeeveveefveeededtv

Amino acid sequence of CnChR1 (Chrimson) with ER export and trafficking signal sequences (SEQ ID NO: 19)

Maelissatrslfaagginpwpnpyhhedmgcggmtptgecfstewwcdpsyglsdagygycfveatggylvvgvek
kqawlhsrgtpgekigaqvcqwiafsiaialltfygfsawkatcgweevyvccvevlfvtleifkefsspatvylst
gnhayclryfewllscpviliklsnlsglkndyskrtmglivscvgmivfgmaaglatdwlkwllyivsciyggymy
fqaakcyveanhsvpkghcrmvvklmayayfaswgsypilwavgpegllklspyansighsicdiiakefwtflahh
lrikihehilihgdirktttkmeiggeeveveefveeededtv*AAA*KSRITSEGEYIPLDQIDINVFCYENEV

Amino acid sequence of CsChrimson (SEQ ID NO: 20)

Msrlvaaswllalllcgitstttassapaasstdgtaaaavshyamngfdelakgavvpedhfvcgpadkcycsawl
hsrgtpgekigaqvcqwiafsiaialltfygfsawkatcgweevyvccvevlfvtleifkefsspatvylstgnhay
clryfewllscpviliklsnlsglkndyskrtmglivscvgmivfgmaaglatdwlkwllyivsciyggymyfqaak
cyveanhsvpkghcrmvvklmayayfaswgsypilwavgpegllklspyansighsicdiiakefwtflahhlriki
hehilihgdirktttkmeiggeeveveefveeededtv

Amino acid sequence of CsChrimson with ER export and trafficking signal sequences (SEQ ID NO: 21)

Msrlvaaswllalllcgitstttassapaasstdgtaaaavshyamngfdelakgavvpedhfvcgpadkcycsawl
hsrgtpgekigaqvcqwiafsiaialltfygfsawkatcgweevyvccvevlfvtleifkefsspatvylstgnhay
clryfewllscpviliklsnlsglkndyskrtmglivscvgmivfgmaaglatdwlkwllyivsciyggymyfqaak
cyveanhsvpkghcrmvvklmayayfaswgsypilwavgpegllklspyansighsicdiiakefwtflahhlriki
hehilihgdirktttkmeiggeeveveefveeededtv*AAA*KSRITSEGEYIPLDQIDINVFCYENEV

Amino acid sequence of ShChR1 (Chronos) (SEQ ID NO: 22)

metaatmthafisavpsaeatirgllsaaavvtpaadahgetsnattagadhgcfphinhgtelqhkiavglqwftv
ivaivqlifygwhsfkattgweevyvcvielvkcfielfhevdspatvyqtnggaviwlrysmwlltcpvilihlsn
ltglheeyskrtmtilvtdignivwgitaaftkgplkilffmiglfygvtcffqiakvyiesyhtlpkgvcrkicki
mayvffcswlmfpvmfiagheglglitpytsgighlildliskntwgflghhlrvkihehilihgdirkttttinvag
enmeietfvdeeeeggv

FIG. 16 (cont.)

Amino acid sequence of ShChR1 (Chronos) with ER export and trafficking signal sequences (SEQ ID NO: 23)

metaatmthafisavpsaeatirgllsaaavvtpaadahgetsnattagadhgcfphinhgtelqhkiavglqwftv
ivaivqlifygwhsfkattgweevyvcvielvkcfielfhevdspatvyqtnggaviwlrysmwlltcpvilihlsn
ltglheeyskrtmtilvtdignivwgitaaftkgplkilffmiglfygvtcffqiakvyiesyhtlpkgvcrkicki
mayvffcswlmfpvmfiagheglglitpytsgighlildliskntwgflghhlrvkihehilihgdirkttinvag
enmeietfvdeeeeggv*AAA*KSRITSEGEYIPLDQIDINVFCYENEV

FIG. 17

(hyperpolarizing opsins)
amino acid sequence of Archaerhodopsin-3 (SEQ ID NO: 24)

MDPIALQAGYDLLGDGRPETLWLGIGTLLMLIGTFYFLVRGWGVTDKDAREYYAVTILVPGIASAAYLSM
FFGIGLTEVTVGGEMLDIYYARYADWLFTTPLLLLDLALLAKVDRVTIGTLVGVDALMIVTGLIGALSHT
AIARYSWWLFSTICMIVVLYFLATSLRSAAKERGPEVASTFNTLTALVLVLWTAYPILWIIGTEGAGVVG
LGIETLLFMVLDVTAKVGFGFILLRSRAILGDTEAPEPSAGADVSAAD amino acid sequence of eArch3.0 (SEQ ID NO: 25)

MDPIALQAGYDLLGDGRPETLWLGIGTLLMLIGTFYFLVRGWGVTDKDAREYYAVTILVPGIASAAYLSM
FFGIGLTEVTVGGEMLDIYYARYADWLFTTPLLLLDLALLAKVDRVTIGTLVGVDALMIVTGLIGALSHT
AIARYSWWLFSTICMIVVLYFLATSLRSAAKERGPEVASTFNTLTALVLVLWTAYPILWIIGTEGAGVVG
LGIETLLFMVLDVTAKVGFGFILLRSRAILGDTEAPEPSAGADVSAAD*RPVVAAAA***KSRITSEGEYIPLD
QIDINV**FCYENEV

Amino acid sequence of ArchT (SEQ ID NO: 26)

MDPIALQAGYDLLGDGRPETLWLGIGTLLMLIGTFYFIVKGWGVTDKEAREYYSITILVP
GIASAAYLSMFFGIGLTEVTVAGEVLDIYYARYADWLFTTPLLLLDLALLAKVDRVSIGT
LVGVDALMIVTGLIGALSHTPLARYSWWLFSTICMIVVLYFLATSLRAAAKERGPEVAST
FNTLTALVLVLWTAYPILWIIGTEGAGVVGLGIETLLFMVLDVTAKVGFGFILLRSRAIL
GDTEAPEP

Amino acid sequence of ArchT with ER export and trafficking signal
sequences (SEQ ID NO: 27)

MDPIALQAGYDLLGDGRPETLWLGIGTLLMLIGTFYFIVKGWGVTDKEAREYYSITILVP
GIASAAYLSMFFGIGLTEVTVAGEVLDIYYARYADWLFTTPLLLLDLALLAKVDRVSIGT
LVGVDALMIVTGLIGALSHTPLARYSWWLFSTICMIVVLYFLATSLRAAAKERGPEVAST
FNTLTALVLVLWTAYPILWIIGTEGAGVVGLGIETLLFMVLDVTAKVGFGFILLRSRAIL
GDTEAPEP*AAA*KSRITSEGEYIPLDQIDINVFCYENEV

FIG. 17 (cont.)

amino acid sequence of GtR3 (SEQ ID NO: 28)

MLVGEGAKLDVHGCKTVDMASSFGKALLEFVFIVFACITLLLGINAAKSKAASRVLFPATFVTGIASIAY
FSMASGGGWVIAPDCRQLFVARYLDWLITTPLLLIDLGLVAGVSRWDIMALCLSDVLMIATGAFGSLTVG
NVKWVWWFFGMCWFLHIIFALGKSWAEAAKAKGGDSASVYSKIAGITVITWFCYPVVWVFAEGFGNFSVT
FEVLIYGVLDVISKAVFGLILMSGAATGYESI amino acid sequence of GtR3 with ER export and trafficking signal
sequences (SEQ ID NO: 29)

MLVGEGAKLDVHGCKTVDMASSFGKALLEFVFIVFACITLLLGINAAKSKAASRVLFPATFVTGIASIAY
FSMASGGGWVIAPDCRQLFVARYLDWLITTPLLLIDLGLVAGVSRWDIMALCLSDVLMIATGAFGSLTVG
NVKWVWWFFGMCWFLHIIFALGKSWAEAAKAKGGDSASVYSKIAGITVITWFCYPVVWVFAEGFGNFSVT
FEVLIYGVLDVISKAVFGLILMSGAATGYESI*AAA*KSRITSEGEYIPLDQIDINVFCYENEV

Amino acid sequence of rhodopsin type II proton pump (Oxy) (SEQ ID NO:
30)

MAPLAQDWTYAEWSAVYNALSFGIAGMGSATIFFWLQLPNVTKNYRTALTITGIVTLIATYHYFRIFNSW
VAAFNVGLGVNGAYEVTVSGTPFNDAYRYVDWLLTVPLLLVELILVMKLPAKETVCLAWTLGIASAVMVA
LGYPGEIQDDLSVRWFWWACAMVPFVYVVGTLVVGLGAATAKQPEGVVDLVSAARYLTVVSWLTYPFVYI
VKNIGLAGSTATMYEQIGYSAADVTAKAVFGVLIWAIANAKSRLEEEGKLRA

Amino acid sequence of rhodopsin type II proton pump with ER export
and trafficking signal sequences(SEQ ID NO: 31)

MAPLAQDWTYAEWSAVYNALSFGIAGMGSATIFFWLQLPNVTKNYRTALTITGIVTLIATYHYFRIFNSW
VAAFNVGLGVNGAYEVTVSGTPFNDAYRYVDWLLTVPLLLVELILVMKLPAKETVCLAWTLGIASAVMVA
LGYPGEIQDDLSVRWFWWACAMVPFVYVVGTLVVGLGAATAKQPEGVVDLVSAARYLTVVSWLTYPFVYI
VKNIGLAGSTATMYEQIGYSAADVTAKAVFGVLIWAIANAKSRLEEEGKLRA*AAA***KSRITSEGEYIPLDQ
IDINV**FCYENEV

FIG. 17 (cont.)

Amino acid sequence of L. maculans rhodopsin (Mac) (SEQ ID NO: 32)

MIVDQFEEVLMKTSQLFPLPTATQSAQPTHVAPVPTVLPDTPIYETVGDSGSKTLWVVFVLMLIASAAFT
ALSWKIPVNRRLYHVITTIITLTAALSYFAMATGHGVALNKIVIRTQHDHVPDTYETVYRQVYYARYIDW
AITTPLLLLDLGLLAGMSGAHIFMAIVADLIMVLTGLFAAFGSEGTPQKWGWYTIACIAYIFVVWHLVLN
GGANARVKGEKLRSFFVAIGAYTLILWTAYPIVWGLADGARKIGVDGEIIAYAVLDVLAKGVFGAWLLVT
HANLRESDVELNGFWANGLNREGAIRIGEDDGA

Amino acid sequence of Mac 3.0 (SEQ ID NO: 33)
MIVDQFEEVLMKTSQLFPLPTATQSAQPTHVAPVPTVLPDTPIYETVGDSGSKTLWVVFVLMLIASAAFT
ALSWKIPVNRRLYHVITTIITLTAALSYFAMATGHGVALNKIVIRTQHDHVPDTYETVYRQVYYARYIDW
AITTPLLLLDLGLLAGMSGAHIFMAIVADLIMVLTGLFAAFGSEGTPQKWGWYTIACIAYIFVVWHLVLN
GGANARVKGEKLRSFFVAIGAYTLILWTAYPIVWGLADGARKIGVDGEIIAYAVLDVLAKGVFGAWLLVT
HANLRESDVELNGFWANGLNREGAIRIGEDDGARPVVAVSKAAAKSRITSEGEYIPLDQIDINVFCYENE
V amino acid sequence of NpHR (SEQ ID NO: 34)

<u>MTETLPPVTESAVALQAE</u>VTQRELFEFVLNDPLLASSLYINIALAGLSILLFVFMTRGLDDPRAKLI
AVSTILVPVVSIASYTGLASGLTISVLEMPAGHFAEGSSVMLGGEEVDGVVTMWGRYLTWALST
PMILLALGLLAGSNATKLFTAITFDIAMCVTGLAAALTTSSHLMRWFWYAISCACFLVVLYILLV
EWAQDAKAAGTADMFNTLKLLTVVMWLGYPIVWALGVEGIAVLPVGVTSWGYSFLDIVAKYI
FAFLLLNYLTSNESVVSGSILDVPSASGTPADD amino acid sequence of NpHR3.0 (SEQ ID NO: 35)

<u>MTETLPPVTESAVALQAE</u>VTQRELFEFVLNDPLLASSLYINIALAGLSILLFVFMTRGLDDPRAKLI
AVSTILVPVVSIASYTGLASGLTISVLEMPAGHFAEGSSVMLGGEEVDGVVTMWGRYLTWALST
PMILLALGLLAGSNATKLFTAITFDIAMCVTGLAAALTTSSHLMRWFWYAISCACFLVVLYILLV
EWAQDAKAAGTADMFNTLKLLTVVMWLGYPIVWALGVEGIAVLPVGVTSWGYSFLDIVAKYI
FAFLLLNYLTSNESVVSGSILDVPSASGTPADD<u>AAAKSRITSEGEYIPLDQIDINFCYENEV</u> amino acid sequence of NpHR3.1 (SEQ ID NO: 36)

MVTQRELFEFVLNDPLLASSLYINIALAGLSILLFVFMTRGLDDPRAKLIAVSTILVPVVSIASYTG
LASGLTISVLEMPAGHFAEGSSVMLGGEEVDGVVTMWGRYLTWALSTPMILLALGLLAGSNAT
KLFTAITFDIAMCVTGLAAALTTSSHLMRWFWYAISCACFLVVLYILLVEWAQDAKAAGTADM
FNTLKLLTVVMWLGYPIVWALGVEGIAVLPVGVTSWGYSFLDIVAKYIFAFLLLNYLTSNESVVS
GSILDVPSASGTPADD<u>AAAKSRITSEGEYIPLDQIDINFCYENEV</u>

FIG. 17 (cont.)

**Amino acid sequence of *Dunaliella salina* channelrhodopsin** (SEQ ID NO: 37)
Mrrresqlaylclfvliagwaprltesapdlaerrppserntpyanikkvpnitepnanvqldg
walyqdfyylagsdkewvvgpsdqcycrawskshgtdregeaavvwayivfaicivqlvyfmfa
awkatvgweevyvniielvhialviwvefdkpamlylndgqmvpwlrysawllscpvilihlsn
ltglkgdyskrtmgllvsdigtivfgtsaalappnhvkvilftigllyglftfftaakvyieay
htvpkgqcrnlvramawtyfvswamfpilfilgregfghityfgssighfileifsknlwsllg
hglryrirqhiiihgnltkknkiniagdnveveeyvdsndkdsdv

**Amino acid sequence of *Dunaliella salina* channelrhodopsin** with ER export and trafficking signal sequences (SEQ ID NO: 38)
mrrresqlaylclfvliagwaprltesapdlaerrppserntpyanikkvpnitepnanvqldg
walyqdfyylagsdkewvvgpsdqcycrawskshgtdregeaavvwayivfaicivqlvyfmfa
awkatvgweevyvniielvhialviwvefdkpamlylndgqmvpwlrysawllscpvilihlsn
ltglkgdyskrtmgllvsdigtivfgtsaalappnhvkvilftigllyglftfftaakvyieay
htvpkgqcrnlvramawtyfvswamfpilfilgregfghityfgssighfileifsknlwsllg
hglryrirqhiiihgnltkknkiniagdnveveeyvdsndkdsdv*AAA***KSRITSEGEYIPLDQID
INV**FCYENEV

Amino acid sequence of a iC1C2 (SEQ ID NO: 39)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV

Amino acid sequence of a iC1C2 with ER export and trafficking signal sequences (SEQ ID NO: 40)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAVAA
*A*KSRITSEGEYIPLDQIDINVFCYENEV

Amino acid sequence of a SwiChR (iC1C2-C167A or T or S) (SEQ ID NO: 41)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTXPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV

FIG. 17 (cont.)

Amino acid sequence of a SwiChR (iC1C2-C167A or T or S) with ER export and trafficking signal sequences (SEQ ID NO: 42)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTXPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV*AA
A*KSRITSEGEYIPLDQIDINVFCYENEV

Amino acid sequence of ibC1C2 (SEQ ID NO: 43)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVILIRLSNLTG
LANDYNKRTMGLLVSDIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV

Amino acid sequence of ibC1C2 with ER export and trafficking signal sequences (SEQ ID NO: 44)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVILIRLSNLTG
LANDYNKRTMGLLVSDIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV*AAA*KSRITSEGEYIPLDQIDINVFCYENEV

Amino acid sequence of iChR2 (SEQ ID NO: 45)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTCPVILIRLSNLTG
LSNDYSRRTMGLLVSDIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP

Amino acid sequence of iChR2 with ER export and trafficking signal sequences (SEQ ID NO: 46)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTCPVILIRLSNLTG
LSNDYSRRTMGLLVSDIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP*AAA*KSRITSEGEYIPLDQIDINVFCYENEV

FIG. 17 (cont.)

Amino acid sequence of iC1V1 (SEQ ID NO: 47)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVLLIRLSNLTGLKDDYSKRTMGLLVSDVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED

Amino acid sequence of iC1V1 with ER export and trafficking signal sequences (SEQ ID NO: 48)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVLLIRLSNLTGLKDDYSKRTMGLLVSDVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED*AAA***KSR
ITSEGEYIPLDQIDINV**FCYENEV

Amino acid sequence of ibC1V1 (SEQ ID NO: 49)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVLLIRLSNLTG
LKDDYSKRTMGLLVSDVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED

Amino acid sequence of ibC1V1 with ER export and trafficking signal sequences (SEQ ID NO: 50)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVLLIRLSNLTG
LKDDYSKRTMGLLVSDVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED*AAA*KSRITSEGEYIPLDQIDINVFCYENEV

Amino acid sequence of iReaChR (SEQ ID NO: 51)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTCPVILIRLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS

FIG. 17 (cont.)

Amino acid sequence of iReaChR with ER export and trafficking signal sequences (SEQ ID NO: 52)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTCPVILIRLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS
*AAA*KSRITSEGEYIPLDQIDINVFCYENEV

Amino acid sequence of ibReaChR (SEQ ID NO: 53)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTCPVILIRLSNLTG
LKDDYSKRTMGLLVSDVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS

Amino acid sequence of ibReaChR with ER export and trafficking signal sequences (SEQ ID NO: 54)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTCPVILIRLSNLTG
LKDDYSKRTMGLLVSDVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS*AAA*KSRITSEGEYIPLDQIDINVFCYENEV

FIG. 18

Amino Acids 1-11 of ChR2 (SEQ ID NO: 55)

MDYGGALSAVG

Membrane Trafficking signal (SEQ ID NO: 56)

KSRITSEGEYIPLDQIDINV

ER export signals

VKESL (SEQ ID NO:57);

VLGSL (SEQ ID NO:58);

NANSFCYENEVALTSK (SEQ ID NO:59);

FXYENE (SEQ ID NO:60)

FCYENEV (SEQ ID NO: 61)

Signal sequence of hCHR2

MDYGGALSAVGRELLFVTNPVVVNGS (SEQI ID NO: 62)

Signal sequence of neuronal nAChR beta 2 subunit

MAGHSNSMALFSFSLLWLCSGVLGTEF (SEQI ID NO: 63)

Signal sequence of a nAChR

MGLRALMLWLLAAAGLVRESLQG (SEQI ID NO: 64)

Signal sequence of a nAChR

MRGTPLLLVVSLFSLLQD (SEQI ID NO: 65)

MTETLPPVTESAVALQAE (SEQ ID NO: 66)

DOPAMINE RECEPTOR TYPE 2 SPECIFIC PROMOTER AND METHODS OF USE THEREOF

CROSS-REFERENCE

This application claims the benefit of U.S. Provisional Patent Application No. 62/087,603, filed Dec. 4, 2014, which application is incorporated herein by reference in its entirety.

INTRODUCTION

Dopamine is a catecholamine neurotransmitter involved in signaling between cells in the brain and throughout the body. Dopamine exerts its cellular and biochemical effects on target cells by binding to its receptor, a G protein-coupled, seven-transmembrane receptor. The dopamine type 2 (D2) receptor is one of several dopamine receptors that have been identified. Cells, including neurons, which express the D2 receptor, are involved in many psychological disorders, including drug addiction, obesity, and gambling disorders.

SUMMARY

A nucleic acid comprising a dopamine receptor type 2-specific promoter (D2SP) is provided. In certain embodiments, the nucleic acid comprises a dopamine receptor type 2-specific promoter (D2SP), wherein the D2SP does not include exon 1 of a D2 receptor gene, wherein the D2SP comprises a Kozak sequence, and wherein the D2SP includes a nucleotide sequence having at least 95% sequence identity to the nucleotide sequence set forth in SEQ ID NO: 1. In some cases, the Kozak sequence is at the 3' terminus of the D2SP. In some cases, the D2SP includes a BamHI restriction site. In certain embodiments, the BamHI restriction site is located 5' of the Kozak sequence. In some cases, the D2SP comprises a nucleotide sequence having at least 98% sequence identity to the nucleotide sequence set forth in SEQ ID NO: 1.

In any embodiment set out above or infra, the D2SP is operably linked to a nucleotide sequence encoding a gene product that provides a detectable signal. In certain embodiments, the gene product that provides a detectable signal is a fluorescent protein. In some embodiments, the fluorescent protein is selected from the group consisting of a green fluorescent protein, a yellow fluorescent protein, a cyan fluorescent protein, a calcium indicator and a voltage indicator.

In any embodiment set out above or infra, the D2SP is operably linked to a nucleotide sequence encoding a light-responsive polypeptide. In certain embodiments, the light-responsive polypeptide is a depolarizing light-responsive polypeptide, wherein the depolarizing light-responsive polypeptide includes an amino acid sequence having at least 75% sequence identity to any one of SEQ ID NOs: 4-23. In some embodiments, the light-responsive polypeptide is a hyperpolarizing light-responsive polypeptide, wherein the hyperpolarizing light-responsive polypeptide includes an amino acid sequence having at least 75% sequence identity to any one of SEQ ID NOs: 24-54.

In any embodiment set out above or infra, the D2SP is operably linked to a nucleotide sequence encoding a recombinase. In certain embodiments, the recombinase is selected from the group consisting of a Cre recombinase and a FLP recombinase.

Also provided herein is a recombinant expression vector comprising the nucleic acid of any of the above embodiments.

Also provided herein is a genetically modified host cell comprising the nucleic acid of any of the above nucleic acid embodiments, or the recombinant expression vector of any of the above expression vector embodiments. In certain embodiments, the host cell is a neuronal cell. In certain embodiments, the host cell is a progenitor cell. In certain embodiments, the progenitor cell is a stem cell.

Also provided herein is a method of modulating activity of a target neuron, the method comprising introducing into the target neuron the nucleic acid of any of the above nucleic acid embodiments, wherein the D2SP is operably linked to a light-responsive polypeptide that, when activated by light, induces hyperpolarization or depolarization of the target neuron.

Also provided herein is a method of fluorescently labeling a target cell, the method comprising introducing into the target cell the nucleic acid of any of any of the above embodiments, wherein the D2SP is operably linked to a fluorescent protein that, when expressed, fluorescently labels the target cell. In certain embodiments, the target cell is a neuronal cell. In certain embodiments, the target cell is a progenitor cell. In certain embodiments, the progenitor cell is a stem cell.

Also provided herein is a kit comprising: a) a recombinant expression vector that comprises a nucleic acid comprising a dopamine receptor type 2-specific promoter (D2SP), wherein the D2SP does not include exon 1 of a D2 receptor gene, wherein the D2SP includes a Kozak sequence, and wherein the D2SP comprises a nucleotide sequence having at least 95% sequence identity to the nucleotide sequence set forth in SEQ ID NO: 1; and b) instructions for introducing the recombinant expression vector into a target cell.

In any of the kit embodiments described above or infra, the kit further comprises a control expression vector that comprises a nucleic acid comprising a dopamine receptor type 2-specific promoter (D2SP), wherein the D2SP does not include exon 1 of a D2 receptor gene, wherein the D2SP includes a Kozak sequence, and wherein the D2SP comprises a nucleotide sequence having at least 95% sequence identity to the nucleotide sequence set forth in SEQ ID NO: 1.

BRIEF DESCRIPTION OF THE DRAWINGS

FIG. 1 shows a schematic drawing of the conventional promoter for the type 2 dopamine receptor (D2R) and the D2 specific promoter (D2SP), according to an embodiment of the present disclosure.

FIG. 2 shows aligned nucleotide sequences of D2SP (SEQ ID NO: 1) and the conventional D2 receptor promoter (D2R; SEQ ID NO: 2), according to an embodiment of the present disclosure.

FIG. 5 shows expression of eNpHR 3.0-EYFP under the D2SP and under the conventional D2 receptor promoter (D2R) and antibody staining for D2 receptors, according to an embodiment of the present disclosure.

FIG. 15 shows a nucleotide sequence of exon 1 of the rat D2 receptor.

FIG. 16 shows the amino acid sequences of depolarizing light-responsive polypeptides and derivatives thereof (SEQ ID NOs: 4-23), according to an embodiment of the present disclosure.

FIG. 17 shows the amino acid sequences of hyperpolarizing light-responsive polypeptides and derivatives thereof (SEQ ID NOs: 24-54), according to an embodiment of the present disclosure.

FIG. 18 shows the peptide sequences (SEQ ID NOs: 55-66) that may be used to enhance expression of the light-responsive polypeptides in a host cell or a target cell, according to an embodiment of the present disclosure.

DEFINITIONS

Figure 3:
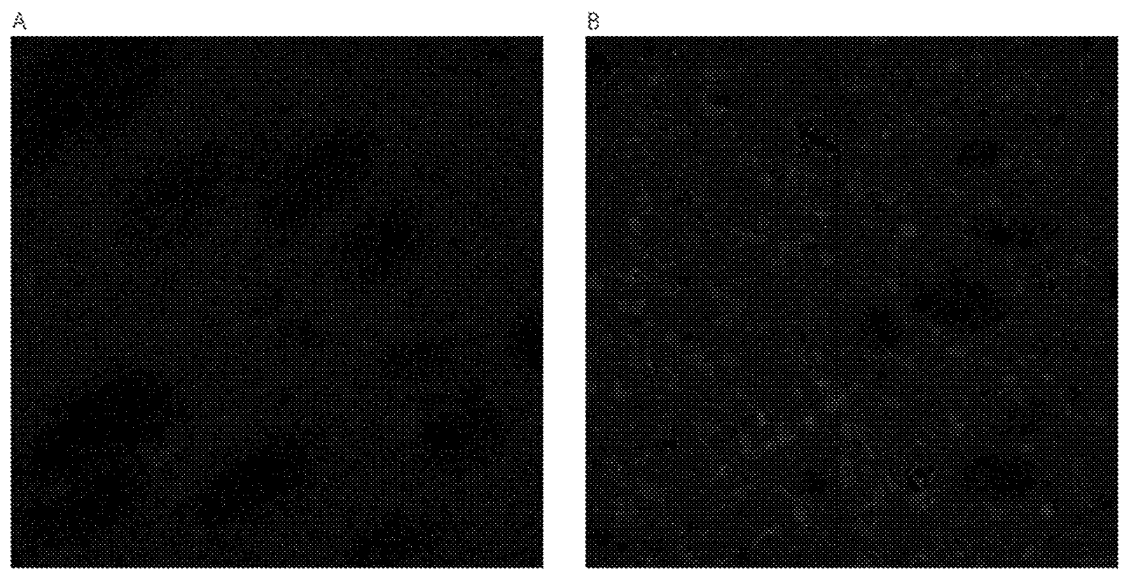
FIG. 3 shows staining of tissue slices with a D2 receptor-specific antibody using a standard protocol (left) and a modified protocol (right).

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

The terms "polypeptide", "peptide" and "protein" are used interchangeably herein to refer to polymers of amino acids of any length. The polymer may be linear, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and, therefore, do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Any suitable means for making this adjustment may be used. This may involve scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Any suitable methods of alignment of sequences for comparison may be employed. Thus, the determination of percent identity between any two sequences can be accomplished using a mathematical algorithm. Preferred, non-limiting examples of such mathematical algorithms are the algorithm of Myers and Miller, CABIOS, 4:11 (1988), which is hereby incorporated by reference in its entirety; the local homology algorithm of Smith et al, Adv. Appl. Math., 2:482 (1981), which is hereby incorporated by reference in its entirety; the homology alignment algorithm of Needleman and Wunsch, J M B, 48:443 (1970), which is hereby incorporated by reference in its entirety; the search-for-similarity-method of Pearson and Lipman, Proc. Natl. Acad. Sci. USA, 85:2444 (1988), which is hereby incorporated by reference in its entirety; the algorithm of Karlin and Altschul, Proc. Natl. Acad. Sci. USA, 87:2264 (1990), which is hereby incorporated by reference in its entirety; modified as in Karhn and Altschul, Proc. Natl. Acad. Sci. USA, 90:5873 (1993), which is hereby incorporated by reference in its entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988), Higgins et al., CABIOS, 5:151 (1989); Corpet et al., Nucl. Acids Res., 16:10881 (1988); Huang et al., CABIOS, 8:155 (1992); and Pearson et al., Meth. Mol. Biol., 24:307 (1994), which are hereby incorporated by reference in their entirety. The ALIGN program is based on the algorithm of Myers and Miller, supra. The BLAST programs of Altschul et al., JMB, 215:403 (1990); Nucl. Acids Res., 25:3389 (1990), which are hereby incorporated by reference in their entirety, are based on the algorithm of Karlin and Altschul supra.

Software for performing BLAST analyses is publicly available through the National Center for Biotechnology Information (NCBI; worldwideweb.ncbi.nlm.nih.gov).

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as "gene product," depending on the context.

"Gene" refers to a polynucleotide sequence that includes control and coding sequences necessary for the production of a polypeptide or precursor. The polypeptide can be encoded by a full length coding sequence or by any portion of the coding sequence. A gene may constitute an uninterrupted coding sequence or it may include one or more introns, bound by the appropriate splice junctions. Moreover, a gene may comprise one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. In this regard, such modified genes may be referred to as "variants" of the "native" gene.

The term "genetic modification" refers to a permanent or transient genetic change induced in a cell following introduction into the cell of a heterologous nucleic acid (i.e., nucleic acid exogenous to the cell). Genetic change ("modification") can be accomplished by incorporation of the heterologous nucleic acid into the genome of the host cell, or by transient or stable maintenance of the heterologous nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

The term "promoter" as used herein refers to a sequence of DNA that directs the expression (transcription) of a gene. A promoter may direct the transcription of a prokaryotic or eukaryotic gene. A promoter may be "inducible", initiating transcription in response to an inducing agent or, in contrast, a promoter may be "constitutive", whereby an inducing agent does not regulate the rate of transcription. A promoter may be regulated in a tissue-specific or tissue-preferred manner, such that it is only active in transcribing the operable linked coding region in a specific tissue type or types.

The term "operably-linked" refers to a functional linkage between a regulatory sequence and a coding sequence. The components so described are thus in a relationship permitting them to function in their intended manner. For example, placing a coding sequence under regulatory control of a promoter means positioning the coding sequence such that the expression of the coding sequence is controlled by the promoter.

As used herein, "terminus," or "end" with respect to the terminus or end of a nucleotide or amino acid sequence, refers to the 5' or 3' end of a nucleotide sequence, or the amino or carboxyl end of an amino acid sequence. Thus, a sequence at the terminus of a nucleotide sequence or polypeptide sequence is a sequence that includes the 5'-most or 3'-most nucleotide of the nucleotide sequence, or the amino or carboxyl end of the polypeptide sequence.

The terms "light-activated," "light-responsive" in reference to a polypeptide or protein that is light-responsive, are used interchangeably and include light-responsive ion channels or opsins, and ion pumps as described herein. Such light-responsive proteins may have a depolarizing or hyperpolarizing effect on the cell on whose plasma membrane the protein is expressed depending on the ion permeability of the activated protein, and the electrochemical gradients present across the plasma membrane.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a genetically modified host cell" includes a plurality of such genetically modified host cells and reference to "the neuronal cell" includes reference to one or more neuronal cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

A nucleic acid comprising a dopamine receptor type 2-specific promoter (D2SP) and methods of using the same to express a polypeptide in a target cell of interest are provided. Aspects of the present disclosure include a nucleic acid comprising a D2SP wherein the D2SP does not include exon 1 of a D2 receptor gene, wherein the D2SP comprises a Kozak sequence, and wherein the D2SP comprises a nucleotide sequence having at least 95% sequence identity to the nucleotide sequence set forth in SEQ ID NO: 1 (FIG. 2).

In some embodiments, a subject nucleic acid comprises a D2SP, wherein the D2SP does not include exon 1 of a D2 receptor gene, wherein the D2SP comprises a Kozak sequence, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1.

In certain embodiments, a subject nucleic acid comprises a D2SP wherein the D2SP does not include exon 1 of a D2 receptor gene, wherein the D2SP comprises a Kozak sequence at the 3' terminus of the D2SP, wherein the D2SP comprises a BamHI restriction site located 5' of the Kozak sequence, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1.

In certain embodiments, a subject nucleic acid comprises a D2SP wherein the D2SP does not include exon 1 of a D2 receptor gene, wherein the D2SP comprises a Kozak sequence at the 3' terminus of the D2SP, wherein the D2SP comprises a BamHI restriction site located 5' of the Kozak sequence, wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1, and wherein the D2SP is operably linked to a nucleotide sequence encoding a gene product. In some cases, the gene product is a polypeptide. In some cases, the gene product is a polynucleotide. In some instances, the gene product is a polypeptide that provides a detectable signal, such as a fluorescent protein; a genetically encoded indicator; a light-responsive polypeptide; a recombinase; or a combination thereof.

In certain embodiments, the subject nucleic acid comprises a D2SP wherein the D2SP does not include exon 1 of a D2 receptor gene, wherein the D2SP comprises a Kozak sequence at the 3' terminus of the D2SP, wherein the D2SP comprises a BamHI restriction site located 5' of the Kozak sequence, wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1, and wherein the D2SP is operably linked to a nucleotide sequence encoding a light-responsive polypeptide selected from the polypeptides of SEQ ID NOs: 4-54.

In certain embodiments, the subject nucleic acid comprises a D2SP wherein the D2SP does not include exon 1 of a D2 receptor gene, wherein the D2SP comprises a Kozak sequence at the 3' terminus of the D2SP, wherein the D2SP comprises a BamHI restriction site located 5' of the Kozak sequence, wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1, and wherein the D2SP is operably linked to a nucleotide sequence encoding a fluorescent protein selected from a green fluorescent protein, a yellow fluorescent protein, a cyan fluorescent protein, a calcium indicator and a voltage indicator.

Also provided herein is a recombinant expression vector comprising a nucleic acid that includes a D2SP, wherein the D2SP does not include exon 1 of a D2 receptor gene, wherein the D2SP comprises a Kozak sequence, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1.

In certain embodiments, the recombinant expression vector comprises a nucleic acid that includes a D2SP, wherein the D2SP does not include exon 1 of a D2 receptor gene, wherein the D2SP comprises a Kozak sequence at the 3' terminus of the D2SP, wherein the D2SP comprises a BamHI restriction site located 5' of the Kozak sequence, wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1, and wherein the D2SP is operably linked to a nucleotide sequence encoding a gene product. In some instances, the gene product is a polypeptide that provides a detectable signal, such as a fluorescent protein; a genetically encoded indicator; a light-responsive polypeptide; a recombinase; or a combination thereof.

Also provided herein is a genetically modified host cell comprising a nucleic acid that comprises a D2SP, wherein the D2SP does not include exon 1 of a D2 receptor gene, wherein the D2SP comprises a Kozak sequence, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1. In some instances the nucleic acid is contained in a recombinant expression vector in the genetically modified host cell.

In certain embodiments, a genetically modified host cell of the present disclosure comprises a recombinant expression vector comprising a nucleic acid that comprises a D2SP, wherein the D2SP does not include exon 1 of a D2 receptor gene, wherein the D2SP comprises a Kozak sequence at the 3' terminus of the D2SP, wherein the D2SP comprises a BamHI restriction site located 5' of the Kozak sequence, wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1, and wherein the D2SP is operably linked to a nucleotide sequence encoding a gene product. In some instances, the gene product is a polypeptide that provides a detectable signal, such as a fluorescent protein; a genetically encoded indicator; a light-responsive polypeptide; a recombinase; or a combination thereof.

Also provided herein is a method of modulating activity of a target neuron, the method including introducing into the target neuron a nucleic acid that comprises a D2SP wherein the D2SP does not include exon 1 of a D2 receptor gene, wherein the D2SP comprises a Kozak sequence at the 3' terminus of the D2SP and a BamHI restriction site located 5' of the Kozak sequence, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1, wherein the D2SP is operably linked to a light-responsive polypeptide that, when activated by light, induces hyperpolarization or depolarization of the target neuron.

Also provided herein is a method of modulating activity of a target neuron, the method comprising introducing into the target neuron a nucleic acid that comprises a D2SP wherein the D2SP does not include exon 1 of a D2 receptor gene, wherein the D2SP comprises a Kozak sequence at the 3' terminus of the D2SP and a BamHI restriction site located 5' of the Kozak sequence, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1, wherein the D2SP is operably linked to a light-responsive polypeptide comprising the amino acid sequence set forth in any one of SEQ ID NOs: 4-23, that, when activated by light, induces depolarization of the target neuron.

Also provided herein is a method of modulating activity of a target neuron, the method comprising introducing into the target neuron a nucleic acid that comprises a D2SP wherein the D2SP does not include exon 1 of a D2 receptor gene, wherein the D2SP comprises a Kozak sequence at the 3' terminus of the D2SP and a BamHI restriction site located 5' of the Kozak sequence, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1, wherein the D2SP is operably linked to a light-responsive polypeptide comprising the amino acid sequence set forth in any one of SEQ ID NOs: 24-54, that, when activated by light, induces hyperpolarization of the target neuron.

Also provided herein is a method of fluorescently labeling a target cell, the method comprising introducing into the target cell a nucleic acid that comprises a D2SP wherein the D2SP does not include exon 1 of a D2 receptor gene, wherein the D2SP comprises a Kozak sequence at the 3' terminus of the D2SP and a BamHI restriction site located 5' of the Kozak sequence, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1, wherein the D2SP is operably linked to a fluorescent protein that, when expressed, fluorescently labels the target cell.

In certain embodiments, a method of the present disclosure of fluorescently labeling a target cell comprises introducing into a target neuron a nucleic acid that comprises a D2SP wherein the D2SP does not include exon 1 of a D2 receptor gene, wherein the D2SP comprises a Kozak sequence at the 3' terminus of the D2SP and a BamHI restriction site located 5' of the Kozak sequence, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1, wherein the D2SP is operably linked to a fluorescent protein that, when expressed, fluorescently labels the target neuron.

In certain embodiments, a method of the present disclosure of fluorescently labeling a target cell comprises introducing into a target progenitor cell a nucleic acid that includes a D2SP wherein the D2SP does not include exon 1 of a D2 receptor gene, wherein the D2SP comprises a Kozak sequence at the 3' terminus of the D2SP and a BamHI restriction site located 5' of the Kozak sequence, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1, wherein the D2SP is operably linked to a fluorescent protein that, when expressed, fluorescently labels the target progenitor cell.

In certain embodiments, a method of the present disclosure of fluorescently labeling a target cell comprises introducing into a target stem cell a nucleic acid that comprises a D2SP wherein the D2SP does not include exon 1 of a D2 receptor gene, wherein the D2SP comprises a Kozak sequence at the 3' terminus of the D2SP and a BamHI restriction site located 5' of the Kozak sequence, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1, wherein the D2SP is operably linked to a fluorescent protein that, when expressed, fluorescently labels the target stem cell.

Further aspects of the present disclosure will now be described in more detail below.

Nucleic Acids

Dopamine Receptor Type 2-specific Promoter (D2SP)

As summarized above, aspects of the present disclosure include a nucleic acid comprising a D2SP, i.e., a promoter sequence that directs expression of genes operably linked to the promoter in cells that express the type 2 dopamine (D2) receptor. In certain embodiments, the D2SP is derived from a genomic sequence 5' of the first exon of a D2 receptor in a genome.

In certain embodiments, the D2 receptor is derived from a mammalian genome, such as, but not limited to, rat, mouse, monkey, non-human primate or human genome.

In some embodiments, the D2SP is derived from a genomic sequence that is 5' of the first exon of a D2 receptor. Thus, in some embodiments, the D2SP is derived from a genomic sequence that begins 3.0 kilobases (kb) or less, e.g., 2.5 kb of less, such as 2.0 kb or less, including 1.6 kb or less 5' of the beginning of the first exon of a D2 receptor. In other embodiments, the D2SP is derived from a genomic sequence that begins 0.5 kilobases (kb) or more, e.g., 1.0 kb of more, such as 1.2 kb or more, including 1.5 kb or more 5' of the beginning of the first exon of a D2 receptor. In certain embodiments, the D2SP is derived from a genomic sequence that begins in the range of 3.0 to 0.5 kb, e.g., 2.5 kb to 1.0 kb, or 2.0 kb to 1.2 kb 5' of the beginning of the first exon or transcriptional start site of the D2 receptor.

The transcriptional start site, or the beginning of the first exon of a gene, as used interchangeably herein, may be defined as the 5' end of a mature RNA (mRNA) transcribed from the genetic locus encoding the gene. Thus in certain embodiments, the beginning of the first exon of a D2 receptor is defined by the 5' end of the mRNA transcribed from the D2 receptor genomic locus. In certain embodiments, the beginning of the first exon of a D2 receptor is defined by the sequence represented by GenBank Accession numbers: NM_012547 (*Rattus norvegicus*); NM_010077 (*Mus musculus*); or NM_000795 (*Homo sapiens*).

In certain embodiments, the length of the D2SR is from 500 base pairs (bp) to 2500 bp, e.g., 750 bp to 2250 bp, 1000 bp to 2000 bp, including 1250 bp to 1750 bp. In some instances, the length of the D2SR is 500 bp or more, e.g., 750 bp or more, 1000 bp or more, 1250 bp or more, 1350 bp or more, 1450 bp or more, 1500 bp or more, 1510 bp or more, 1520 bp or more, or 1530 bp or more. In some instances, the length of the D2SR is 2000 bp or less, e.g., 1750 bp or less, 1700 bp or less, 1650 bp or less, 1600 bp or less, 1590 bp or less, 1580 bp or less, 1570 bp or less, 1560 bp or less, or 1550 bp or less. In another embodiment, the length of the D2SR is about 1540 bp.

Aspects of the present disclosure include a nucleic acid that comprises a D2SP that does not include exon 1 of a D2 receptor gene (FIG. 1). The D2 receptor gene may be any mammalian D2 receptor gene, including, but not limited to the rat D2 receptor gene (GeneID 24318), the mouse D2 receptor gene (GeneID 13489) or the human D2 receptor gene (GeneID 1813). Other mammalian D2 receptor genes include monkey and non-human primate D2 receptor genes. Any suitable method for determining the first exon of a D2 receptor gene may be used. In certain embodiments, the exon 1 of a rat D2 receptor gene is defined by the sequence that is 80% or more, e.g., 85% or more, 90% or more, 95% or more, 98% or more, 99% or more, or 100% identical to the sequence shown in SEQ ID NO: 3 (FIG. 15). Thus, in certain embodiments, the D2SP does not include a sequence that is 80% or more, e.g., 85% or more, 90% or more, 95% or more, 98% or more, 99% or more, or 100% identical to the sequence shown in SEQ ID NO: 3 (FIG. 15). In certain embodiments, the D2SP does not include a nucleotide sequence that is 90% or more, e.g., 95% or more, 98% or more, 99% or more, or 100% identical to nucleotides 1-313, e.g., nucleotides 1-300, nucleotides 1-250, nucleotides 1-200, nucleotides 1-150, nucleotides 1-100, nucleotides 1-90, nucleotides 1-80, nucleotides 1-70, nucleotides 1-60, nucleotides 1-50, nucleotides 1-40, including nucleotides 1-30, of the sequence shown in SEQ ID NO: 3 (FIG. 15). In certain embodiments, the D2SP does not include a nucleotide sequence that is 90% or more, e.g., 95% or more, 98% or more, 99% or more, or 100% identical to nucleotides 1-270 of the sequence shown in SEQ ID NO: 3 (FIG. 15).

Further aspects of the present disclosure include a nucleic acid that comprises a D2SP comprising a Kozak sequence. The term "Kozak sequence" refers to a sequence for facilitating the initial binding of mRNA to the small subunit of the ribosome for initiation of translation. An exemplary Kozak sequence is GCCRCC where R is a purine (A or G). In certain embodiments, the Kozak sequence is GCCACC. In certain embodiments, one, two, three or more nucleotides may be substituted in the exemplary Kozak sequence without significantly affecting the ability of the Kozak sequence to function. (Kozak, M., Cell, 44(2):283-92, 1986; Kozak, M. Nucleic Acids Res., October 26; 15(20):8125-48, 1987; Kozak, M, J. Biol. Chem., 266(30): 19867-19870, 1991.)

In certain embodiments, the Kozak sequence is at the 3' terminus, or end, of the D2SP. Thus, in certain embodiments where the D2SP directs expression of an RNA transcript encoding a polypeptide, the coding sequence for the polypeptide starts immediately 3' of the terminal end of the D2SP. "Immediately," as used herein in reference to a first sequence that is immediately adjacent to a second sequence, indicates that there are no intervening sequences (i.e., no nucleotides or amino acids) between the first and second sequences. Thus, in certain embodiments, the Kozak sequence is immediately followed 3' by the start codon (i.e., the nucleotide sequence ATG) of the coding sequence.

In certain embodiments, the D2SP includes a recognition site for a restriction nuclease. In certain embodiments, the restriction nuclease is BamHI. The recognition site of BamHI is GGATCC. Thus, in certain embodiments, the D2SP includes a BamHI recognition site, defined by the sequence GGATCC. In certain embodiments, the BamHI restriction site is located 5' of the Kozak sequence. In certain embodiments, the BamHI site is located immediately 5' of the Kozak sequence. In some embodiments, the Bam HI restriction site is located 3' of the genomic sequence of the D2 receptor genomic locus from which the D2SP is derived. Thus, in certain embodiments, the Bam HI restriction site is located 3' of the genomic sequence of the D2 receptor genomic locus from which the D2SP is derived and 5' of the Kozak sequence.

In certain embodiments, the D2SP includes a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1 (FIG. 2). Thus, an aspect of the present disclosure includes a nucleic acid comprising a D2SP, wherein the D2SP does not include exon 1 of a D2 receptor gene, wherein the D2SP comprises a Kozak sequence, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1. In another aspect, a subject nucleic acid comprises a D2SP, wherein the D2SP does not include exon 1 of a D2 receptor gene, wherein the D2SP comprises a Kozak sequence and a BamHI restriction site, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1. In certain embodiments, the nucleic acid comprises a D2SP, wherein the D2SP does not include exon 1 of a D2 receptor gene, wherein the D2SP comprises a Kozak sequence at the 3' terminus of the D2SP and a BamHI restriction site located 5' of the Kozak sequence, and wherein the D2SP comprises a nucleotide sequence having at least 75%, e.g., at least 80%, 85%, 90%, 91%, 92%, 93%, 94%, 95%, 96%, 97%, 98%, 99% or 100% sequence identity to the nucleotide sequence set forth in SEQ ID NO: 1.

In certain embodiments, the D2SP is operably linked to a nucleotide sequence encoding a gene product. The gene product may be any suitable gene product that finds use being expressed specifically in target cells that express the D2 receptor. In some cases, the gene product is a polypeptide. In some cases, the gene product is a polynucleotide. In certain embodiments, the gene product is a light-responsive polypeptide. In certain embodiments, the light-responsive polypeptide is a polypeptide that, when expressed on the cell membrane of the target cell and activated by exposure to light of appropriate wavelength and intensity, depolarizes or activates the target cell. In certain embodiments, the light-responsive polypeptide is a polypeptide that, when expressed on the cell membrane of the target cell and activated by exposure to light of appropriate wavelength and intensity, hyperpolarizes or inhibits the target cell. Exemplary light-responsive polypeptides that may be operably linked to the subject D2SP are further described below.

In certain embodiments, the gene product operably linked to a D2SP provides a detectable signal. A detectable signal may be fluorescence, chemiluminescence, enzymatic activity, etc. In certain embodiments, the gene product to which the D2SP is operably linked and that provides a detectable signal is a fluorescent protein, including, but not limited to, a green fluorescent protein, a yellow fluorescent protein, a cyan fluorescent protein, etc. In some embodiments, the gene product to which the D2SP is operably linked and that provides a detectable signal is a genetically encoded indicator, such as, but not limited to, a calcium indicator or a voltage indicator. A calcium indicator is a fluorescent polypeptide that is engineered to bind one or more calcium ions, wherein the binding of the calcium ions alters the fluorescence properties, such as intensity, excitation and/or emission wavelengths, etc., of the polypeptide. Any suitable calcium indicator may be used to provide a detectable signal in the target cell. In some instances, the calcium indicator is a ratiometric calcium indicator, such as Cameleon and derivatives thereof. Other calcium indicators of interest include, but are not limited to GCaMP1, GCaMP2, GCaMP3, and derivatives thereof, as well as those cited in U.S. Pat. No. 8,629,256, and Tian et al. 2012 Prog Brain Res, 196:79 which are incorporated herein by reference. A voltage indicator is a fluorescent polypeptide that is engineered to respond to changes in membrane potential, wherein a change in membrane potential alters the fluorescence properties, such as intensity, excitation and/or emission wavelengths, etc., of the polypeptide. Any suitable voltage indicator may be used to provide a detectable signal in the target cell. Voltage indicators of interest include, but are not limited to QuasAr1, QuasAr2, VSFP, and derivatives thereof, as well as those cited in US App. Pub. No. 20130224756, Hochbaum et al., Nat Methods 2014 11:825, Baker et al. Brain Cell Biol 2008 36:53; and Mutoh et al., Exp Physiol 2011 96:13, which are incorporated herein by reference.

In certain embodiments the D2SP is operably linked to a nucleotide sequence encoding a recombinase. Any suitable recombinase that may be operably linked to the D2SP can be used. Suitable recombinases include, but are not limited to Cre and Flp recombinases, and derivatives thereof. The recombinases and use thereof in inducing site-specific recombination with a target nucleic acid are described, e.g., in US App. Pub. Nos. 20130019325 and 20060003443, U.S. Pat. No. 8,518,392 and Wu et al. PLoS One 2009 4:e8054, which are incorporated herein by reference.

Light-responsive Polypeptides

As summarized above, aspects of the present disclosure include a D2SP operably linked to a nucleotide sequence encoding a light-responsive polypeptide. The light-activated ion channel polypeptides are adapted to allow one or more ions to pass through the plasma membrane of a target cell when the polypeptide is illuminated with light of an activating wavelength. Light-activated proteins may be characterized as ion pump proteins, which facilitate the passage of a small number of ions through the plasma membrane per photon of light, or as ion channel proteins, which allow a stream of ions to freely flow through the plasma membrane when the channel is open. In some embodiments, the light-responsive polypeptide depolarizes the target cell when activated by light of an activating wavelength. In some embodiments, the light-responsive polypeptide hyperpolarizes the target cell when activated by light of an activating wavelength.

In some embodiments, the light-responsive polypeptides are activated by blue light. In some embodiments, the light-responsive polypeptides are activated by green light. In some embodiments, the light-responsive polypeptides are activated by yellow light. In some embodiments, the light-responsive polypeptides are activated by orange light. In some embodiments, the light-responsive polypeptides are activated by red light.

In some embodiments, the light-responsive polypeptide expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-responsive protein transport to the plasma membranes of mammalian cells can be fused to the N-terminus, the C-terminus, or to both the N- and C-terminal ends of the light-responsive polypeptide. In some cases, the one or more amino acid sequence motifs which enhance light-responsive polypeptide transport to the plasma membranes of mammalian cells is fused internally within a light-responsive polypeptide. Optionally, the light-responsive polypeptide and the one or more amino acid sequence motifs may be separated by a linker.

In some embodiments, the light-responsive polypeptide can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

ER export sequences that are suitable for use with a light-responsive polypeptide include, e.g., VXXSL (where X is any amino acid) (e.g., VKESL (SEQ ID NO: 57); VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

Signal sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such as one of the following: 1) the signal peptide of hChR2 (e.g., MDYGGALSAVGRELLFVTNPVVVNGS (SEQ ID NO: 62)); 2) the β2 subunit signal peptide of the neuronal nicotinic acetylcholine receptor (e.g., MAGHSNS-MALFSFSLLWLCSGVLGTEF (SEQ ID NO: 63)); 3) a nicotinic acetylcholine receptor signal sequence (e.g., MGL- RALMLWLLAAAGLVRESLQG (SEQ ID NO: 64)); and 4) a nicotinic acetylcholine receptor signal sequence (e.g., MRGTPLLLVVSLFSLLQD (SEQ ID NO: 65)).

A signal sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

In some embodiments, the signal peptide sequence in the protein can be deleted or substituted with a signal peptide sequence from a different protein.

Exemplary light-responsive polypeptides are described in, e.g., PCT App. No. PCT/US2011/028893, which is incorporated herein by reference. Representative light-responsive polypeptides that find use in the present disclosure are further described below.

Depolarizing Light-responsive Polypeptides
ChR

In some aspects, a depolarizing light-responsive polypeptide is derived from *Chlamydomonas reinhardtii*, wherein the polypeptide is capable of transporting cations across a cell membrane when the cell is illuminated with light. In another embodiment, the light-responsive polypeptide comprise an amino acid sequence at least 75%, 85%, 90%, 91%, 92%, 93%, 94%, 95%, 96%, 97%, 98%, 99%, or 100% identical to the sequence shown in SEQ ID NO: 4. The light used to activate the light-responsive cation channel protein derived from *Chlamydomonas reinhardtii* can have a wavelength between about 460 and about 495 nm or can have a wavelength of about 480 nm. Additionally, light pulses having a temporal frequency of about 100 Hz can be used to activate the light-responsive protein. In some embodiments, activation of the light-responsive cation channel derived from *Chlamydomonas reinhardtii* with light pulses having a temporal frequency of about 100 Hz can cause depolarization of the neurons expressing the light-responsive cation channel. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can comprise one or more conservative amino acid substitutions and/or one or more non-conservative amino acid substitutions. The light-responsive proton pump protein containing substitutions, deletions, and/or insertions introduced into the native amino acid sequence suitably retains the ability to transport cations across a cell membrane.

In some embodiments, the light-responsive cation channel includes a T159C substitution of the amino acid sequence set forth in SEQ ID NO: 4. In some embodiments, the light-responsive cation channel includes a L132C substitution of the amino acid sequence set forth in SEQ ID NO: 4. In some embodiments, the light-responsive cation channel includes an E123T substitution of the amino acid sequence set forth in SEQ ID NO: 4. In some embodiments, the light-responsive cation channel includes an E123A substitution of the amino acid sequence set forth in SEQ ID NO: 4. In some embodiments, the light-responsive cation channel includes a T159C substitution and an E123T substitution of the amino acid sequence set forth in SEQ ID NO: 4. In some embodiments, the light-responsive cation channel includes a T159C substitution and an E123A substitution of the amino acid sequence set forth in SEQ ID NO: 4. In some embodiments, the light-responsive cation channel includes a T159C substitution, an L132C substitution, and an E123T substitution of the amino acid sequence set forth in SEQ ID NO: 4. In some embodiments, the light-responsive cation channel includes a T159C substitution, an L132C substitution, and an E123A substitution of the amino acid sequence set forth in SEQ ID NO: 4. In some embodiments, the light-responsive cation channel includes an L132C substitution and an E123T substitution of the amino acid sequence set forth in SEQ ID NO: 4. In some embodiments, the light-responsive cation channel includes an L132C substitution and an E123A substitution of the amino acid sequence set forth in SEQ ID NO: 4.

In some embodiments, a ChR2 protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the ChR2 protein comprises an N-terminal signal peptide and a C-terminal ER export signal. In some embodiments, the ChR2 protein comprises an N-terminal signal peptide and a C-terminal trafficking signal. In some embodiments, the ChR2 protein comprises an N-terminal signal peptide, a C-terminal ER export signal, and a C-terminal trafficking signal. In some embodiments, the ChR2 protein comprises a C-terminal ER export signal and a C-terminal trafficking signal. In some embodiments, the C-terminal ER export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

In certain embodiments, the ChR2 protein can have an amino acid sequence that is at least 75%, 85%, 90%, 91%, 92%, 93%, 94%, 95%, 96%, 97%, 98%, 99%, or 100% identical to the sequence shown in SEQ ID NO: 5.

In other embodiments, the light-responsive polypeptide is a step function opsin (SFO) protein or a stabilized step function opsin (SSFO) protein that can have specific amino acid substitutions at key positions in the retinal binding pocket of the protein. In some embodiments, the SFO protein can have a mutation at amino acid residue C128 of SEQ ID NO: 4. In other embodiments, the SFO protein has a C128A mutation in SEQ ID NO: 4. In other embodiments, the SFO protein has a C128S mutation in SEQ ID NO: 4. In another embodiment, the SFO protein has a C128T mutation in SEQ ID NO: 4.

In some embodiments, the SSFO protein can have a mutation at amino acid residue D156 of SEQ ID NO: 4. In other embodiments, the SSFO protein can have a mutation at both amino acid residues C128 and D156 of SEQ ID NO: 4. In one embodiment, the SSFO protein has an C128S and a D156A mutation in SEQ ID NO: 4. In another embodiment, the SSFO protein can comprise an amino acid sequence at least 75%, 85%, 90%, 91%, 92%, 93%, 94%, 95%, 96%, 97%, 98%, 99%, or 100% identical to the sequence shown in SEQ ID NO: 6; and includes an alanine, serine, or threonine at amino acid 128; and includes a alanine at amino acid 156. In another embodiment, the SSFO protein can comprise a C128T mutation in SEQ ID NO: 4. In some embodiments, the SSFO protein includes C128T and D156A mutations in SEQ ID NO: 6.

In some embodiments the SFO or SSFO proteins provided herein can be capable of mediating a depolarizing current in the cell when the cell is illuminated with blue light. In other embodiments, the light can have a wavelength of about 445 nm. Additionally, in some embodiments the light can be delivered as a single pulse of light or as spaced pulses of light due to the prolonged stability of SFO and SSFO photocurrents. In some embodiments, activation of the SFO or SSFO protein with single pulses or spaced pulses of light can cause depolarization of a neuron expressing the SFO or SSFO protein. In some embodiments, each of the disclosed step function opsin and stabilized step function opsin proteins can have specific properties and characteristics for use in depolarizing the membrane of a neuronal cell in response to light.

Further disclosure related to SFO or SSFO proteins can be found in International Patent Application Publication No. WO 2010/056970, the disclosure of which is hereby incorporated by reference in its entirety.

In some cases, the ChR2-based SFO or SSFO comprises a membrane trafficking signal and/or an ER export signal. In some embodiments, the trafficking signal is derived from the amino acid sequence of the human inward rectifier potassium channel Kir2.1. In other embodiments, the trafficking signal comprises the amino acid sequence KSRITSEGEYIPLDQIDINV (SEQ ID NO: 56). Trafficking sequences that are suitable for use comprises an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

In certain embodiments, the SSFO protein comprises an amino acid sequence that is at least 75%, 85%, 90%, 91%, 92%, 93%, 94%, 95%, 96%, 97%, 98%, 99%, or 100% identical to the sequence shown in SEQ ID NO: 7.

Volvox Carteri Light-responsive Polypeptide

In some embodiments, a suitable light-responsive polypeptide is a cation channel derived from Volvox carteri (VChR1) and is activated by illumination with light of a wavelength of from about 500 nm to about 600 nm, e.g., from about 525 nm to about 550 nm, e.g., 545 nm. In some embodiments, the light-responsive ion channel protein comprises an amino acid sequence at least 75%, 85%, 90%, 91%, 92%, 93%, 94%, 95%, 96%, 97%, 98%, 99%, or 100% identical to the sequence shown in SEQ ID NO: 8. The light-responsive ion channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive ion channel protein to regulate the polarization state of the plasma membrane of the cell. Additionally, the light-responsive ion channel protein can comprise one or more conservative amino acid substitutions and/or one or more non-conservative amino acid substitutions. The light-responsive ion channel protein containing substitutions, deletions, and/or insertions introduced into the native amino acid sequence suitably retains the ability to transport ions across the plasma membrane of a neuronal cell in response to light.

In some cases, a VChR1 light-responsive cation channel protein comprises a core amino acid sequence at least 75%, 85%, 90%, 91%, 92%, 93%, 94%, 95%, 96%, 97%, 98%, 99%, or 100% identical to the sequence shown in SEQ ID NO: 8 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton ion channel comprises an N-terminal signal peptide and a C-terminal ER export signal. In some embodiments, the light-responsive ion channel protein comprises an N-terminal signal peptide and a C-terminal trafficking signal. In some embodiments, the light-responsive ion channel protein comprises an N-terminal signal peptide, a C-terminal ER Export signal, and a C-terminal trafficking signal. In some embodiments, the light-responsive ion channel protein comprises a C-terminal ER Export signal and a C-terminal trafficking signal. In some embodiments, the C-terminal ER Export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

In some embodiments, the trafficking signal is derived from the amino acid sequence of the human inward rectifier potassium channel Kir2.1. In other embodiments, the trafficking signal comprises the amino acid sequence KSRITSEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

In certain embodiments, the VChR1 protein comprises an amino acid sequence that is at least 75%, 85%, 90%, 91%, 92%, 93%, 94%, 95%, 96%, 97%, 98%, 99%, or 100% identical to the sequence shown in SEQ ID NO: 9.

Step Function Opsins and Stabilized Step Function Opsins Based on VChR1

In other embodiments, the light-responsive polypeptide is a SFO or an SSFO based on VChR1. In some embodiments, the SFO protein can have a mutation at amino acid residue C123 of SEQ ID NO: 8. In other embodiments, the SFO protein has a C123A mutation in SEQ ID NO: 8. In other embodiments, the SFO protein has a C123S mutation in SEQ ID NO: 8. In another embodiment, the SFO protein has a C123T mutation in SEQ ID NO: 8.

In some embodiments, the SFO protein can have a mutation at amino acid residue D151 of SEQ ID NO: 8. In other embodiments, the SFO protein can have a mutation at both amino acid residues C123 and D151 of SEQ ID NO: 8. In one embodiment, the SFO protein has an C123S and a D151A mutation in SEQ ID NO: 8.

In some embodiments an SFO or SSFO protein is capable of mediating a depolarizing current in the cell when the cell is illuminated with blue light. In some embodiments, the light has a wavelength of about 560 nm. Additionally, in some embodiments the light is delivered as a single pulse of light or as spaced pulses of light due to the prolonged stability of SFO and SSFO photocurrents. In some embodiments, activation of the SFO or SSFO protein with single pulses or spaced pulses of light can cause depolarization of a neuron expressing the SFO or SSFO protein. In some embodiments, each of the disclosed step function opsin and stabilized step function opsin proteins can have specific properties and characteristics for use in depolarizing the membrane of a neuronal cell in response to light.

In some cases, the VChR1-based SFO or SSFO comprises a membrane trafficking signal and/or an ER export signal. In some embodiments, the trafficking signal can be derived from the amino acid sequence of the human inward rectifier potassium channel Kir2.1. Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

C1V1 Chimeric Cation Channels

In other embodiments, the light-responsive cation channel protein is a C1V1 chimeric protein derived from the VChR1 protein of *Volvox carteri* and the ChR1 protein from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some embodiments, the C1V1 protein further comprises a replacement within the intracellular loop domain located between the second and third transmembrane helices of the chimeric light responsive protein, wherein at least a portion of the intracellular loop domain is replaced by the corresponding portion from ChR1. In another embodiment, the portion of the intracellular loop domain of the C1V1 chimeric protein can be replaced with the corresponding portion from ChR1 extending to amino acid residue A145 of the ChR1. In other embodiments, the C1V1 chimeric protein further comprises a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1. In other embodiments, the C1V1 chimeric protein comprises an amino acid sequence at least 75%, 85%, 90%, 91%, 92%, 93%, 94%, 95%, 96%, 97%, 98%, 99%, or 100% identical to the sequence shown in SEQ ID NO: 10.

In some embodiments, the C1V1 protein mediates a depolarizing current in the cell when the cell is illuminated with green light. In some embodiments, the light has a wavelength of between about 540 nm to about 560 nm. In some embodiments, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, in some embodiments, light pulses having a temporal frequency of about 100 Hz can be used to activate the C1V1 protein.

In some cases, the C1V1 polypeptide comprises a membrane trafficking signal and/or an ER export signal. In some embodiments, the trafficking signal is derived from the amino acid sequence of the human inward rectifier potassium channel Kir2.1. In other embodiments, the trafficking signal comprises the amino acid sequence KSRITSEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

In certain embodiments, the C1V1 protein comprises an amino acid sequence that is at least 75%, 85%, 90%, 91%, 92%, 93%, 94%, 95%, 96%, 97%, 98%, 99%, or 100% identical to the sequence shown in SEQ ID NO: 11.

C1V1 Variants

In some aspects, a suitable light-responsive polypeptide comprises substituted or mutated amino acid sequences, wherein the mutant polypeptide retains the characteristic light-activatable nature of the precursor C1V1 chimeric polypeptide but may also possess altered properties in some specific aspects. For example, the mutant light-responsive C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-responsive cation channels, and/or strong expression in animal cells.

Accordingly, suitable light-responsive proteins include C1V1 chimeric light-responsive proteins that can have specific amino acid substitutions at key positions throughout the retinal binding pocket of the VChR1 portion of the chimeric polypeptide. In some embodiments, the C1V1 protein comprises an amino acid substitution at amino acid residue E122 of SEQ ID NO: 10. In some embodiments, the C1V1 protein comprises a substitution at amino acid residue E162 of SEQ ID NO: 10. In other embodiments, the C1V1 protein comprises a substitution at both amino acid residues E162 and E122 of SEQ ID NO: 10.

In some aspects, the C1V1-E122 mutant chimeric protein is capable of mediating a depolarizing current in the cell when the cell is illuminated with light. In some embodiments the light is green light. In other embodiments, the light has a wavelength of between about 540 nm to about 560 nm. In some embodiments, the light has a wavelength of about 546 nm. In other embodiments, the C1V1-E122 mutant chimeric protein mediates a depolarizing current in the cell when the cell is illuminated with red light. In some embodiments, the red light has a wavelength of about 630 nm. In some embodiments, the C1V1-E122 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, in some embodiments, light pulses having a temporal frequency of about 100 Hz can be used to activate the C1V1-E122 mutant chimeric protein. In some embodiments, activation of the C1V1-E122 mutant chimeric protein with light pulses having a frequency of 100 Hz can cause depolarization of the neurons expressing the C1V1-E122 mutant chimeric protein.

In other aspects, the C1V1-E162 mutant chimeric protein is capable of mediating a depolarizing current in the cell when the cell is illuminated with light. In some embodiments the light can be green light. In other embodiments, the light can have a wavelength of between about 535 nm to about 540 nm. In some embodiments, the light can have a wavelength of about 542 nm. In other embodiments, the light can have a wavelength of about 530 nm. In some embodiments, the C1V1-E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, in some embodiments, light pulses having a temporal frequency of about 100 Hz can be used to activate the C1V1-E162 mutant chimeric protein. In some embodiments, activation of the C1V1-E162 mutant chimeric protein with light pulses having a frequency of 100 Hz can cause depolarization-induced synaptic depletion of the neurons expressing the C1V1-E162 mutant chimeric protein.

In yet other aspects, the C1V1-E122/E162 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In some embodiments, the C1V1-E122/E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. In some embodiments, the C1V1-E122/E162 mutant chimeric protein can exhibit less activation when exposed to violet light relative to C1V1 chimeric proteins lacking mutations at E122/E162 or relative to other light-responsive cation channel proteins. Additionally, in some embodiments, light pulses having a temporal frequency of about 100 Hz can be used to activate the C1V1-E122/E162 mutant chimeric protein. In some embodiments, activation of the C1V1-E122/E162 mutant chimeric protein with light pulses having a frequency of 100 Hz can cause depolarization-induced synaptic depletion of the neurons expressing the C1V1-E122/E162 mutant chimeric protein.

In some cases, the C1V1 variant polypeptide comprises a membrane trafficking signal and/or an ER export signal. In some embodiments, the trafficking signal can be derived from the amino acid sequence of the human inward rectifier potassium channel Kir2.1. In other embodiments, the trafficking signal comprises the amino acid sequence KSRITSEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

C1C2 Chimeric Cation Channels

In other embodiments, the light-responsive cation channel protein is a C1C2 chimeric protein derived from the ChR1 and the ChR2 proteins from *Chlamydomonas reinhardti*, wherein the protein is responsive to light and is capable of mediating a depolarizing current in the cell when the cell is illuminated with light. In another embodiment, the light-responsive polypeptide comprises an amino acid sequence at least 75%, 85%, 90%, 91%, 92%, 93%, 94%, 95%, 96%, 97%, 98%, 99%, or 100% identical to the sequence shown in SEQ ID NO: 12. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein comprises one or more conservative amino acid substitutions and/or one or more non-conservative amino acid substitutions. The light-responsive proton pump protein containing substitutions, deletions, and/or insertions introduced into the native amino acid sequence suitably retains the ability to transport cations across a cell membrane.

In some embodiments, a C1C2 protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the C1C2 protein comprises an N-terminal signal peptide and a C-terminal ER export signal. In some embodiments, the C1C2 protein comprises an N-terminal signal peptide and a C-terminal trafficking signal. In some embodiments, the C1C2 protein comprises an N-terminal signal peptide, a C-terminal ER export signal, and a C-terminal trafficking signal. In some embodiments, the C1C2 protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

In certain embodiments, the C1C2 protein comprises an amino acid sequence that is at least 75%, 85%, 90%, 91%, 92%, 93%, 94%, 95%, 96%, 97%, 98%, 99%, or 100% identical to the sequence shown in SEQ ID NO: 13.

ReaChR

In some aspects, a depolarizing light-responsive polypeptide is a red shifted variant of a depolarizing light-responsive polypeptide derived from *Chlamydomonas reinhardtii*; such light-responsive polypeptides are referred to herein as a "ReaChR polypeptide" or "ReaChR protein" or "ReaChR." In another embodiment, the light-responsive polypeptide comprises an amino acid sequence at least 75%, 85%, 90%, 91%, 92%, 93%, 94%, 95%, 96%, 97%, 98%, 99%, or 100% identical to the sequence shown in SEQ ID NO: 14. The light used to activate the ReaChR polypeptide can have a wavelength between about 590 and about 630 nm or can have a wavelength of about 610 nm. The ReaChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the ReaChR protein can comprise one or more conservative amino acid substitutions and/or one or more non-conservative amino acid substitutions. The ReaChR containing substitutions, deletions, and/or insertions introduced into the native amino acid sequence suitably retains the ability to transport cations across a cell membrane.

In some embodiments, a ReaChR protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the ReaChR protein comprises an N-terminal signal peptide and a C-terminal ER export signal. In some embodiments, the ReaChR protein comprises an N-terminal signal peptide and a C-terminal trafficking signal. In some embodiments, the ReaChR protein comprises an N-terminal signal peptide, a C-terminal ER export signal, and a C-terminal trafficking signal. In some embodiments, the ReaChR protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

In certain embodiments, the ReaChR protein comprises an amino acid sequence that is at least 75%, 85%, 90%, 91%, 92%, 93%, 94%, 95%, 96%, 97%, 98%, 99%, or 100% identical to the sequence shown in SEQ ID NO: 15.

SdChR

In some aspects, a depolarizing light-responsive polypeptide is a SdChR polypeptide derived from *Scherffelia dubia*, wherein the SdChR polypeptide is capable of transporting cations across a cell membrane when the cell is illuminated with light. In some cases, the SdChR polypeptide comprises an amino acid sequence at least 75%, 85%, 90%, 91%, 92%, 93%, 94%, 95%, 96%, 97%, 98%, 99%, or 100% identical to the sequence shown in SEQ ID NO: 16. The light used to activate the SdChR polypeptide can have a wavelength between about 440 and about 490 nm or can have a wavelength of about 460 nm. The SdChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the SdChR protein to regulate the polarization state of the plasma membrane of the cell. In some instances, the SdChR protein comprises one or more conservative amino acid substitutions and/or one or more non-conservative amino acid substitutions. The SdChR protein containing substitutions, deletions, and/or insertions introduced into the native amino acid sequence suitably retains the ability to transport cations across a cell membrane.

In some embodiments, a SdChR protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the SdChR protein comprises an N-terminal signal peptide and a C-terminal ER export signal. In some embodiments, the SdChR protein comprises an N-terminal signal peptide and a C-terminal trafficking signal. In some embodiments, the SdChR protein comprises an N-terminal signal peptide, a C-terminal ER export signal, and a C-terminal trafficking signal. In some embodiments, the SdChR protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal comprises the amino acid sequence KSRITSEGEYIPLDQIDINV (SEQ ID NO: 56). Trafficking sequences that are suitable for use comprises an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCY-ENEVALTSK (SEQ ID NO: 59); FXYENE (SEQ ID NO: 60) (where X is any amino acid), e.g., FCYENEV (SEQ ID NO: 61); and the like.

In certain embodiments, the SdChR protein comprises an amino acid sequence that is at least 75%, 85%, 90%, 91%, 92%, 93%, 94%, 95%, 96%, 97%, 98%, 99%, or 100% identical to the sequence shown in SEQ ID NO: 17.

CnChR1

In some aspects, a depolarizing light-responsive polypeptide can be, e.g. CnChR1, derived from *Chlamydomonas noctigama*, wherein the CnChR1 polypeptide is capable of transporting cations across a cell membrane when the cell is illuminated with light. In some cases, the CnChR1 polypeptide comprises an amino acid sequence at least 75%, 85%, 90%, 91%, 92%, 93%, 94%, 95%, 96%, 97%, 98%, 99%, or 100% identical to the sequence shown in SEQ ID NO: 18. The light used to activate the CnChR1 polypeptide can have a wavelength between about 560 and about 630 nm or can have a wavelength of about 600 nm. The CnChR1 protein can additionally comprise substitutions, deletions, and/or insertions introduced into a native amino acid sequence to increase or decrease sensitivity to light, increase or decrease sensitivity to particular wavelengths of light, and/or increase or decrease the ability of the CnChR1 protein to regulate the polarization state of the plasma membrane of the cell. In some cases, the CnChR1 protein comprises one or more conservative amino acid substitutions and/or one or more non-conservative amino acid substitutions. The CnChR1 protein containing substitutions, deletions, and/or insertions introduced into the native amino acid sequence suitably retains the ability to transport cations across a cell membrane.

In some embodiments, a CnChR1 protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the CnChR1 protein includes an N-terminal signal peptide and a C-terminal ER export signal. In some embodiments, the CnChR1 protein includes an N-terminal signal peptide and a C-terminal trafficking signal. In some embodiments, the CnChR1 protein comprises an N-terminal signal peptide, a C-terminal ER export signal, and a C-terminal trafficking signal. In some embodiments, the CnChR1 protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal is derived from the amino acid sequence of the human inward rectifier potassium channel Kir2.1. In other embodiments, the trafficking signal comprises the amino acid sequence KSRITSEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCY-ENEVALTSK (SEQ ID NO: 59); FXYENE (SEQ ID NO: 60) (where X is any amino acid), e.g., FCYENEV (SEQ ID NO: 61); and the like.

In certain embodiments, the CnChR1 protein comprises an amino acid sequence that is at least 75%, 85%, 90%, 91%, 92%, 93%, 94%, 95%, 96%, 97%, 98%, 99%, or 100% identical to the sequence shown in SEQ ID NO: 19.

CsChrimson

In other embodiments, the light-responsive cation channel protein is a CsChrimson chimeric protein derived from a CsChR protein of *Chloromonas subdivisa* and CnChR1 protein from *Chlamydomonas noctigama*, wherein the N terminus of the protein comprises the amino acid sequence of residues 1-73 of CsChR followed by residues 79-350 of the amino acid sequence of CnChR1; is responsive to light; and is capable of mediating a depolarizing current in the cell when the cell is illuminated with light. In another embodiment, the CsChrimson polypeptide comprises an amino acid sequence at least 75%, 85%, 90%, 91%, 92%, 93%, 94%, 95%, 96%, 97%, 98%, 99%, or 100% identical to the sequence shown in SEQ ID NO: 20. The CsChrimson protein can additionally comprise substitutions, deletions, and/or insertions introduced into a native amino acid sequence to increase or decrease sensitivity to light, increase or decrease sensitivity to particular wavelengths of light, and/or increase or decrease the ability of the CsChrimson protein to regulate the polarization state of the plasma membrane of the cell. Additionally, the CsChrimson protein can comprise one or more conservative amino acid substitutions and/or one or more non-conservative amino acid substitutions. A CsChrimson protein containing substitutions, deletions, and/or insertions introduced into the native amino acid sequence suitably retains the ability to transport cations across a cell membrane.

In some embodiments, a CsChrimson protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the CsChrimson protein comprises an N-terminal signal peptide and a C-terminal ER export signal. In some embodiments, the CsChrimson protein comprises an N-terminal signal peptide and a C-terminal trafficking signal. In some embodiments, the CsChrimson protein comprises an N-terminal signal peptide, a C-terminal ER export signal, and a C-terminal trafficking signal. In some embodiments, the CsChrimson protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal is derived from the amino acid sequence of the human inward rectifier potassium channel Kir2.1. In other embodiments, the trafficking signal comprises the amino acid sequence KSRITSEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

In certain embodiments, the CsChrimson protein comprises an amino acid sequence that is at least 75%, 85%, 90%, 91%, 92%, 93%, 94%, 95%, 96%, 97%, 98%, 99%, or 100% identical to the sequence shown in SEQ ID NO: 21.

ShChR1

In some aspects, a depolarizing light-responsive polypeptide can be, e.g. ShChR1, derived from *Stigeoclonium helveticum*, wherein the ShChR1 polypeptide is capable of transporting cations across a cell membrane when the cell is illuminated with light. In some cases, the ShChR1 polypeptide comprises an amino acid sequence at least 75%, 85%, 90%, 91%, 92%, 93%, 94%, 95%, 96%, 97%, 98%, 99%, or 100% identical to the sequence shown in SEQ ID NO: 22. The light used to activate the ShChR1 protein derived from *Stigeoclonium helveticum* can have a wavelength between about 480 and about 510 nm or can have a wavelength of about 500 nm. The ShChR1 protein can additionally comprise substitutions, deletions, and/or insertions introduced into a native amino acid sequence to increase or decrease sensitivity to light, increase or decrease sensitivity to particular wavelengths of light, and/or increase or decrease the ability of the ShChR1 protein to regulate the polarization state of the plasma membrane of the cell. Additionally, the ShChR1 protein can comprise one or more conservative amino acid substitutions and/or one or more non-conservative amino acid substitutions. A ShChR1 protein containing substitutions, deletions, and/or insertions introduced into the native amino acid sequence suitably retains the ability to transport cations across a cell membrane.

In some embodiments, a ShChR1 protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the ShChR1 protein comprises an N-terminal signal peptide and a C-terminal ER export signal. In some embodiments, the ShChR1 protein comprises an N-terminal signal peptide and a C-terminal trafficking signal. In some embodiments, the ShChR1 protein comprises an N-terminal signal peptide, a C-terminal ER export signal, and a C-terminal trafficking signal. In some embodiments, the ShChR1 protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal comprises the amino acid sequence KSRITSEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

In certain embodiments, the ShChR1 protein comprises an amino acid sequence that is at least 75%, 85%, 90%, 91%, 92%, 93%, 94%, 95%, 96%, 97%, 98%, 99%, or 100% identical to the sequence shown in SEQ ID NO: 23.

Other suitable depolarizing light-responsive polypeptides are described in, e.g., Klapoetke et al. Nat Methods 2014 11:338.

Hyperpolarizing Light-responsive Polypeptides

Arch

In some embodiments, a suitable light-responsive polypeptide is an Archaerhodopsin (Arch) proton pump (e.g., a proton pump derived from *Halorubrum sodomense*) that can transport one or more protons across the plasma membrane of a cell when the cell is illuminated with light. The light can have a wavelength between about 530 and about 595 nm or can have a wavelength of about 560 nm. In some embodiments, the Arch protein comprises an amino acid sequence that is at least 75%, 85%, 90%, 91%, 92%, 93%, 94%, 95%, 96%, 97%, 98%, 99%, or 100% identical to the sequence shown in SEQ ID NO: 24. The Arch protein can additionally have substitutions, deletions, and/or insertions introduced into a native amino acid sequence to increase or decrease sensitivity to light, increase or decrease sensitivity to particular wavelengths of light, and/or increase or decrease the ability of the Arch protein to transport ions across the plasma membrane of a target cell. Additionally, the Arch protein can comprise one or more conservative amino acid substitutions and/or one or more non-conservative amino acid substitutions. An Arch protein containing substitutions, deletions, and/or insertions introduced into the native amino acid sequence suitably retains the ability to transport ions across the plasma membrane of a target cell in response to light.

In some embodiments, the Arch protein comprises at least one (such as one, two, three, or more) amino acid sequence motifs selected from a signal peptide, an ER export signal, and a membrane trafficking signal, that enhance transport to the plasma membranes of target cells. In some embodiments, the Arch protein comprises an N-terminal signal peptide and a C-terminal ER export signal. In some embodiments, the Arch protein comprises an N-terminal signal peptide and a C-terminal trafficking signal. In some embodiments, the Arch protein comprises an N-terminal signal peptide, a C-terminal ER export signal, and a C-terminal trafficking signal. In some embodiments, the Arch protein includes a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further include a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal is derived from the amino acid sequence of the human inward rectifier potassium channel Kir2.1. In other embodiments, the trafficking signal can include the amino acid sequence KSRITSEGEYIPLDQIDINV (SEQ ID NO: 56). Trafficking sequences that are suitable for use can include an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

In certain embodiments, the Arch protein comprises an amino acid sequence that is at least 75%, 85%, 90%, 91%, 92%, 93%, 94%, 95%, 96%, 97%, 98%, 99%, or 100% identical to the sequence shown in SEQ ID NO: 25.

ArchT

In some embodiments, a suitable light-activated protein is an Archaerhodopsin (ArchT) proton pump (e.g., a proton pump derived from Halorubrum sp. TP009) that can transport one or more protons across the plasma membrane of a cell when the cell is illuminated with light. The light can have a wavelength between about 530 and about 595 nm or can have a wavelength of about 560 nm. In some embodiments, the ArchT protein comprises an amino acid sequence that is at least 75%, 85%, 90%, 91%, 92%, 93%, 94%, 95%, 96%, 97%, 98%, 99%, or 100% identical to the sequence shown in SEQ ID NO: 26 (ArchT). The ArchT protein can additionally comprise substitutions, deletions, and/or insertions introduced into a native amino acid sequence to increase or decrease sensitivity to light, increase or decrease sensitivity to particular wavelengths of light, and/or increase or decrease the ability of the ArchT protein to transport ions across the plasma membrane of a target cell. Additionally, the ArchT protein can comprise one or more conservative amino acid substitutions and/or one or more non-conservative amino acid substitutions. The ArchT protein containing substitutions, deletions, and/or insertions introduced into the native amino acid sequence suitably retains the ability to transport ions across the plasma membrane of a target cell in response to light.

In some cases, the ArchT polypeptide comprises a membrane trafficking signal and/or an ER export signal. In some embodiments, the trafficking signal can be derived from the amino acid sequence of the human inward rectifier potassium channel Kir2.1. In other embodiments, the trafficking signal comprises the amino acid sequence KSRITSEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

In certain embodiments, the ArchT protein comprises an amino acid sequence that is at least 75%, 85%, 90%, 91%, 92%, 93%, 94%, 95%, 96%, 97%, 98%, 99%, or 100% identical to the sequence shown in SEQ ID NO: 27.

GtR3

In some embodiments, the light-responsive polypeptide is responsive to blue light and is a proton pump protein derived from Guillardia theta, wherein the proton pump protein is capable of mediating a hyperpolarizing current in the cell when the cell is illuminated with blue light; such a protein is referred to herein as a "GtR3 protein" or a "GtR3 polypeptide". The light can have a wavelength between about 450 and about 495 nm or can have a wavelength of about 490 nm. In some embodiment, a GtR3 protein comprises an amino acid sequence at least 85%, 90%, 91%, 92%, 93%, 94%, 95%, 96%, 97%, 98%, 99%, or 100% identical to the sequence shown in SEQ ID NO: 28 (GtR3). The GtR3 protein can additionally comprise substitutions, deletions, and/or insertions introduced into a native amino acid sequence to increase or decrease sensitivity to light, increase or decrease sensitivity to particular wavelengths of light, and/or increase or decrease the ability of the GtR3 protein to regulate the polarization state of the plasma membrane of the cell. Additionally, the GtR3 protein can comprise one or more conservative amino acid substitutions and/or one or more non-conservative amino acid substitutions. The GtR3 protein containing substitutions, deletions, and/or insertions introduced into the native amino acid sequence suitably retains the ability to hyperpolarize the plasma membrane of a neuronal cell in response to light.

In some cases, a GtR3 protein comprises a core amino acid sequence at least 75%, 85%, 90%, 91%, 92%, 93%, 94%, 95%, 96%, 97%, 98%, 99%, or 100% identical to the sequence shown in SEQ ID NO: 28 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, GtR3 protein comprises an N-terminal signal peptide and a C-terminal ER export signal. In some embodiments, the GtR3 protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the GtR3 protein comprises a C-terminal ER Export signal and a C-terminal trafficking signal. In some embodiments, the signal peptide comprises the amino acid sequence MDYGGALSAVGRELLFVTNPVVVNGS (SEQ ID NO: 62). In some embodiments, the first 19 amino acids are replaced with MDYGGALSAVGRELLFVTNPV-VVNGS (SEQ ID NO: 62). In some embodiments, the C-terminal ER Export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The GtR3 protein may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

In some embodiments, the trafficking signal is derived from the amino acid sequence of the human inward rectifier potassium channel Kir2.1. In other embodiments, the trafficking signal comprises the amino acid sequence KSRIT-SEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCY-ENEVALTSK (SEQ ID NO: 59); FXYENE (SEQ ID NO: 60) (where X is any amino acid), e.g., FCYENEV (SEQ ID NO: 61); and the like.

In certain embodiments, a GtR3 protein comprises an amino acid sequence that is at least 75%, 85%, 90%, 91%, 92%, 93%, 94%, 95%, 96%, 97%, 98%, 99%, or 100% identical to the sequence shown in SEQ ID NO: 29.

Oxy

In some embodiments, a light-activated protein is an Oxyrrhis marina (Oxy) proton pump that can transport one or more protons across the plasma membrane of a cell when the cell is illuminated with light. The light can have a wavelength between about 500 and about 560 nm or can have a wavelength of about 530 nm. In some embodiments, the Oxy protein comprises an amino acid sequence that is at least 75%, 85%, 90%, 91%, 92%, 93%, 94%, 95%, 96%, 97%, 98%, 99%, or 100% identical to the sequence shown in SEQ ID NO: 30. The Oxy protein can additionally comprise substitutions, deletions, and/or insertions introduced into a native amino acid sequence to increase or decrease sensitivity to light, increase or decrease sensitivity to particular wavelengths of light, and/or increase or decrease the ability of the Oxy protein to transport ions across the plasma membrane of a target cell. Additionally, the Oxy protein can comprise one or more conservative amino acid substitutions and/or one or more non-conservative amino acid substitutions. The Oxy protein containing substitutions, deletions, and/or insertions introduced into the native amino acid sequence suitably retains the ability to transport ions across the plasma membrane of a target cell in response to light.

In some embodiments, an Oxy protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the Oxy protein comprises an N-terminal signal peptide and a C-terminal ER export signal. In some embodiments, the Oxy protein includes an N-terminal signal peptide and a C-terminal trafficking signal. In some embodiments, the Oxy protein comprises an N-terminal signal peptide, a C-terminal ER export signal, and a C-terminal trafficking signal. In some embodiments, the Oxy protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The Oxy protein may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some cases, the Oxy polypeptide comprises a membrane trafficking signal and/or an ER export signal. In some embodiments, the trafficking signal can be derived from the amino acid sequence of the human inward rectifier potassium channel Kir2.1. In other embodiments, the trafficking signal comprises the amino acid sequence KSRITSEGEYI-PLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

In certain embodiments, the Oxy protein comprises an amino acid sequence that is at least 75%, 85%, 90%, 91%, 92%, 93%, 94%, 95%, 96%, 97%, 98%, 99%, or 100% identical to the sequence shown in SEQ ID NO: 31.

Mac

In some embodiments, the light-responsive proton pump protein (referred to herein as "Mac protein") is responsive to light and is derived from Leptosphaeria maculans, wherein the Mac proton pump protein is capable of pumping protons across the membrane of a cell when the cell is illuminated with 520 nm to 560 nm light. The light can have a wavelength between about 520 nm to about 560 nm. In some cases, a Mac protein comprises an amino acid sequence at least 75%, 85%, 90%, 91%, 92%, 93%, 94%, 95%, 96%, 97%, 98%, 99%, or 100% identical to the sequence shown in SEQ ID NO: 32 or SEQ ID NO: 33 (Mac; Mac 3.0). The Mac protein can additionally comprise substitutions, deletions, and/or insertions introduced into a native amino acid sequence to increase or decrease sensitivity to light, increase or decrease sensitivity to particular wavelengths of light, and/or increase or decrease the ability of the Mac protein to regulate the polarization state of the plasma membrane of the cell. Additionally, the Mac protein can comprise one or more conservative amino acid substitutions and/or one or more non-conservative amino acid substitutions. A Mac protein containing substitutions, deletions, and/or insertions introduced into the native amino acid sequence suitably retains the ability to pump protons across the plasma membrane of a neuronal cell in response to light.

In other aspects, a Mac protein comprises a core amino acid sequence at least 75%, 85%, 90%, 91%, 92%, 93%, 94%, 95%, 96%, 97%, 98%, 99%, or 100% identical to the sequence shown in SEQ ID NO: 32 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the Mac protein comprises an N-terminal signal peptide and a C-terminal ER export signal. In some embodiments, the Mac protein comprises an N-terminal signal peptide and a C-terminal trafficking signal. In some embodiments, the Mac protein comprises an N-terminal signal peptide, a C-terminal ER Export signal, and a C-terminal trafficking signal. In some embodiments, the Mac protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The Mac protein may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

In some cases, the Mac polypeptide includes a membrane trafficking signal and/or an ER export signal. In some embodiments, the trafficking signal can be derived from the amino acid sequence of the human inward rectifier potassium channel Kir2.1. In other embodiments, the trafficking signal comprises the amino acid sequence KSRITSEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

Further disclosure related to light-activated proton pump proteins can be found in International Patent Application No. PCT/US2011/028893, the disclosure of which is hereby incorporated by reference in its entirety.

NpHR

In some cases, a suitable light-responsive chloride pump protein is derived from Natronomonas pharaonis; such a protein is referred to herein as an "NpHR protein" or an "NpHR polypeptide." In some embodiments, the NpHR protein can be responsive to amber light as well as red light and can mediate a hyperpolarizing current in the neuron when the NpHR protein is illuminated with amber or red light. The wavelength of light that can activate the NpHR protein can be between about 580 and 630 nm. In some embodiments, the light can be at a wavelength of about 589 nm or the light can have a wavelength greater than about 630 nm (e.g. less than about 740 nm). In another embodiment, the light has a wavelength of around 630 nm. In some embodiments, the NpHR protein can hyperpolarize a neural membrane for at least about 90 minutes when exposed to a continuous pulse of light. In some embodiments, the NpHR protein comprises an amino acid sequence at least about 75%, 85%, 90%, 91%, 92%, 93%, 94%, 95%, 96%, 97%, 98%, 99%, or 100% identical to the sequence shown in SEQ ID NO: 34. Additionally, the NpHR protein can comprise substitutions, deletions, and/or insertions introduced into a native amino acid sequence to increase or decrease sensitivity to light, increase or decrease sensitivity to particular wavelengths of light, and/or increase or decrease the ability of the NpHR protein to regulate the polarization state of the plasma membrane of the cell. In some embodiments, the NpHR protein comprises one or more conservative amino acid substitutions. In some embodiments, the NpHR protein comprises one or more non-conservative amino acid substitutions. A NpHR protein containing substitutions, deletions, and/or insertions introduced into the native amino acid sequence suitably retains the ability to hyperpolarize the plasma membrane of a neuronal cell in response to light.

In some cases, an NpHR protein comprises a core amino acid sequence at least about 75%, 85%, 90%, 91%, 92%, 93%, 94%, 95%, 96%, 97%, 98%, 99%, or 100% identical to the sequence shown in SEQ ID NO: 34; and an endoplasmic reticulum (ER) export signal. This ER export signal can be fused to the C-terminus of the core amino acid sequence or can be fused to the N-terminus of the core amino acid sequence. In some embodiments, the ER export signal is linked to the core amino acid sequence by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal comprises the amino acid sequence FXYENE (SEQ ID NO: 60), where X can be any amino acid. In another embodiment, the ER export signal comprises the amino acid sequence VXXSL, where X can be any amino acid. In some embodiments, the ER export signal comprises the amino acid sequence FCYENEV (SEQ ID NO: 61).

Endoplasmic reticulum (ER) export sequences that are suitable for use include, e.g., VXXSL (where X is any amino acid)) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In other aspects, an NpHR protein comprises core amino acid sequence at least 75%, 85%, 90%, 91%, 92%, 93%, 94%, 95%, 96%, 97%, 98%, 99%, or 100% identical to the sequence shown in SEQ ID NO: 34 and a trafficking signal (e.g., which can enhance transport of the NpHR protein to the plasma membrane). The trafficking signal may be fused to the C-terminus of the core amino acid sequence or may be fused to the N-terminus of the core amino acid sequence. In some embodiments, the trafficking signal can be linked to the core amino acid sequence by a linker, which can be any of about 5, 10, 20, 30, 40, 50, 75, 100, 125, 150, 175, 200, 225, 250, 275, 300, 400, or 500 amino acids in length. The NpHR protein may further comprise a fluorescent protein, for example, but not limited to, a yellow fluorescent protein, a red fluorescent protein, a green fluorescent protein, or a cyan fluorescent protein. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO: 56).

In some aspects, an NpHR protein comprises a core amino acid sequence at least 75%, 85%, 90%, 91%, 92%, 93%, 94%, 95%, 96%, 97%, 98%, 99%, or 100% identical to the sequence shown in SEQ ID NO: 34; and at least one (such as one, two, three, or more) amino acid sequence motifs which enhance transport to the plasma membranes of mammalian cells selected from the group consisting of an ER export signal, a signal peptide, and a membrane trafficking signal. In some embodiments, the NpHR protein includes an N-terminal signal peptide, a C-terminal ER Export signal, and a C-terminal trafficking signal. In some embodiments, the C-terminal ER Export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The NpHR protein can also further comprise a fluorescent protein, for example, but not limited to, a yellow fluorescent protein, a red fluorescent protein, a green fluorescent protein, or a cyan fluorescent protein. In some embodiments the ER Export signal can be more C-terminally located than the trafficking signal. In other embodiments the trafficking signal is more C-terminally located than the ER Export signal. In some embodiments, the signal peptide includes the amino acid sequence MTETLPPVTESAVALQAE (SEQ ID NO: 66). In another embodiment, the NpHR protein includes an amino acid sequence at least 95% identical to SEQ ID NO: 35. In another embodiment, the NpHR protein includes an amino acid sequence at least 95% identical to SEQ ID NO: 36.

Moreover, in other aspects, an NpHR protein a core amino acid sequence at least 75%, 85%, 90%, 91%, 92%, 93%, 94%, 95%, 96%, 97%, 98%, 99%, or 100% identical to the sequence shown in SEQ ID NO: 34, wherein the N-terminal signal peptide of SEQ ID NO: 34 is deleted or substituted. In some embodiments, other signal peptides (such as signal peptides from other opsins) can be used. The light-responsive protein can further comprise an ER transport signal and/or a membrane trafficking signal described herein.

In some embodiments, the light-responsive protein is an NpHR protein that comprises an amino acid sequence at least 75%, at least 85%, at least 90%, at least 95%, at least 96%, at least 97%, at least 98%, at least 99% or 100% identical to the sequence shown in SEQ ID NO: 34. In some embodiments, the NpHR protein further comprises an endoplasmic reticulum (ER) export signal and/or a membrane trafficking signal. For example, the NpHR protein comprises an amino acid sequence at least 95% identical to the sequence shown in SEQ ID NO: 34 and an endoplasmic reticulum (ER) export signal. In some embodiments, the amino acid sequence at least 95% identical to the sequence shown in SEQ ID NO: 34 is linked to the ER export signal through a linker. In some embodiments, the ER export signal comprises the amino acid sequence FXYENE (SEQ ID NO: 60), where X can be any amino acid. In another embodiment, the ER export signal comprises the amino acid sequence VXXSL, where X can be any amino acid. In some embodiments, the ER export signal comprises the amino acid sequence FCYENEV (SEQ ID NO: 61). In some embodiments, the NpHR protein comprises an amino acid sequence at least 95% identical to the sequence shown in SEQ ID NO: 34, an ER export signal, and a membrane trafficking signal. In other embodiments, the NpHR protein comprises, from the N-terminus to the C-terminus, the amino acid sequence at least 95% identical to the sequence shown in SEQ ID NO: 34, the ER export signal, and the membrane trafficking signal. In other embodiments, the NpHR protein comprises, from the N-terminus to the C-terminus, the amino acid sequence at least 95% identical to the sequence shown in SEQ ID NO: 34, the membrane trafficking signal, and the ER export signal. In some embodiments, the membrane trafficking signal is derived from the amino acid sequence of the human inward rectifier potassium channel Kir2.1. In some embodiments, the membrane trafficking signal comprises the amino acid sequence KSRITSEGEYIPLDQIDINV (SEQ ID NO: 56). In some embodiments, the membrane trafficking signal is linked to the amino acid sequence at least 95% identical to the sequence shown in SEQ ID NO: 34 by a linker. In some embodiments, the membrane trafficking signal is linked to the ER export signal through a linker. The linker may be any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the light-responsive protein further comprises an N-terminal signal peptide.

Further disclosure related to light-responsive chloride pump proteins can be found in U.S. Patent Application Publication Nos: 2009/0093403 and 2010/0145418 as well as in International Patent Application NO: PCT/US2011/028893, the disclosures of each of which are hereby incorporated by reference in their entireties.

*Dunaliella salina* Light-responsive Polypeptide

In some embodiments, a suitable light-responsive ion channel protein is, e.g., a DsChR protein derived from *Dunaliella salina*, wherein the ion channel protein is capable of mediating a hyperpolarizing current in the cell when the cell is illuminated with light. The light can have a wavelength between about 470 nm and about 510 nm or can have a wavelength of about 490 nm.

In some embodiments, a DsChR protein comprises an amino acid sequence at least 75%, 85%, 90%, 91%, 92%, 93%, 94%, 95%, 96%, 97%, 98%, 99%, or 100% identical to the sequence shown in SEQ ID NO: 37. The DsChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the DsChR protein to regulate the polarization state of the plasma membrane of the cell. Additionally, the DsChR protein can comprise one or more conservative amino acid substitutions and/or one or more non-conservative amino acid substitutions. A DsChR protein containing substitutions, deletions, and/or insertions introduced into the native amino acid sequence suitably retains the ability to transport ions across the plasma membrane of a neuronal cell in response to light.

In some case, a DsChR protein comprises a core amino acid sequence at least 75%, 85%, 90%, 91%, 92%, 93%, 94%, 95%, 96%, 97%, 98%, 99%, or 100% identical to the sequence shown in SEQ ID NO: 37; and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the DsChR protein comprises an N-terminal signal peptide and a C-terminal ER export signal. In some embodiments, the DsChR protein comprises an N-terminal signal peptide and a C-terminal trafficking signal. In some embodiments, the DsChR protein comprises an N-terminal signal peptide, a C-terminal ER Export signal, and a C-terminal trafficking signal. In some embodiments, the DsChR protein comprises a C-terminal ER Export signal and a C-terminal trafficking signal. In some embodiments, the C-terminal ER Export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The DsChR protein may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

In some cases, the DsChR polypeptide comprises a membrane trafficking signal and/or an ER export signal. In some embodiments, the trafficking signal is derived from the amino acid sequence of the human inward rectifier potassium channel Kir2.1. In other embodiments, the trafficking signal comprises the amino acid sequence KSRITSEGEYIPLDQIDINV (SEQ ID NO: 56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 56)). In some cases, the ER export signal is, e.g., VXXSL (where X is any amino acid) (e.g., VKESL (SEQ ID NO: 57), VLGSL (SEQ ID NO: 58); etc.); NANSFCYENEVALTSK (SEQ ID NO: 59); FXYENE (SEQ ID NO: 60) (where X is any amino acid), e.g., FCYENEV (SEQ ID NO: 61); and the like.

In certain embodiments, the DsChR protein comprises an amino acid sequence that is at least 75%, 85%, 90%, 91%, 92%, 93%, 94%, 95%, 96%, 97%, 98%, 99%, or 100% identical to the sequence shown in SEQ ID NO: 38.

Anion Channel Polypeptides Based on C1C2

In some embodiments, a light-responsive anion channel polypeptide is a C1C2 protein. In some embodiments, a C1C2 polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 12. In some embodiments, the amino acid sequence of the C1C2 protein is modified by introducing one or more of the following mutations into the amino acid sequence: T98S, E129S, E140S, E162S, V156K, H173R, T285N, V281K and/or N297Q. In some embodiments, a C1C2 protein comprises the amino acid sequence of the protein C1C2 with all 9 of the above-listed amino acid substitutions, such that the amino acid sequence of the C1C2 polypeptide is that set forth in SEQ ID NO: 39.

In some embodiments, a C1C2 polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 39; and includes 1, 2, 3, 4, 5, 6, 7, 8, or 9 amino acid substitutions selected from T98S, E129S, E140S, E162S, V156K, H173R, T285N, V281K and/or N297Q, relative to the amino acid sequence of C1C2 (SEQ ID NO: 12). In some embodiments, a C1C2 polypeptide includes an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 39; and includes T98S, E129S, E140S, E162S, and T285N substitutions relative to the amino acid sequence of C1C2. In some embodiments, a C1C2 polypeptide includes an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 39; and includes V156K, H173R, V281K, and N297Q substitutions relative to the amino acid sequence of C1C2.

In some embodiments, a C1C2 polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 39; and includes 1, 2, 3, 4, 5, 6, 7, 8, or 9 of: S98, S129, S140, S162, K156, R173, N285, K281, and Q297, where the amino acid numbering is as set forth in SEQ ID NO: 39. In some embodiments, a C1C2 polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 39; and includes S98, S129, S140, S162, K156, R173, N285, K281, and Q297, where the amino acid numbering is as set forth in SEQ ID NO: 39. In any one of these embodiments, a C1C2 polypeptide can comprise a membrane trafficking signal (e.g., KSRITSEGEYIPLDQIDINV (SEQ ID NO: 56)). In any one of these embodiments, a C1C2 polypeptide can comprise an ER export signal (e.g., FCYENEV (SEQ ID NO: 61)). In any one of these embodiments, a C1C2 polypeptide comprises both a membrane trafficking signal (e.g., KSRITSEGEYIPLDQIDINV (SEQ ID NO: 56)) and an ER export signal (e.g., FCYENEV (SEQ ID NO: 61)). Thus, in certain embodiments, the C1C2 protein comprises an amino acid sequence that is at least 75%, 85%, 90%, 91%, 92%, 93%, 94%, 95%, 96%, 97%, 98%, 99%, or 100% identical to the sequence shown in SEQ ID NO: 40.

In some embodiments, a C1C2 polypeptide is based on the amino acid sequence of the protein C1C2 (SEQ ID NO: 12), wherein the amino acid sequence has been modified by replacing the first 50 N-terminal amino acids of C1C2 with amino acids 1-11 from the protein ChR2 (MDYGGAL- SAVG) (SEQ ID NO: 55). In some embodiments, a suitable light-responsive anion channel polypeptide is referred to as "ibC1C2" and comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 43; and includes 1, 2, 3, 4, 5, 6, 7, 8, or 9 of: S59, S90, S101, S123, K117, R134, N246, K242, and Q258, where the amino acid numbering is as set forth in SEQ ID NO: 43. In some embodiments, a suitable light-responsive anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 43; and includes S59, S90, S101, S123, K117, R134, N246, K242, and Q258, where the amino acid numbering is as set forth in SEQ ID NO: 43. In some embodiments, a suitable light-responsive anion channel polypeptide comprises the amino acid sequence set forth in SEQ ID NO: 43. In any one of these embodiments, a suitable anion channel polypeptide comprises a membrane trafficking signal (e.g., KSRITSEGEYIPLDQIDINV (SEQ ID NO: 56)). In any one of these embodiments, a suitable anion channel polypeptide comprises an ER export signal (e.g., FCYENEV (SEQ ID NO: 61)). In any one of these embodiments, a suitable anion channel polypeptide comprises both a membrane trafficking signal (e.g., KSRITSEGEYIPLDQIDINV (SEQ ID NO: 56)) and an ER export signal (e.g., FCYENEV (SEQ ID NO: 61)). Thus, in certain embodiments, the ibC1C2 protein comprises an amino acid sequence that is at least 75%, 85%, 90%, 91%, 92%, 93%, 94%, 95%, 96%, 97%, 98%, 99%, or 100% identical to the sequence shown in SEQ ID NO: 44.

In some embodiments, a suitable light-responsive anion channel polypeptide is based on the amino acid sequence of the protein C1C2 (SEQ ID NO: 12), wherein the cysteine amino acid residue at position 167 has been replaced by a threonine residue. In some embodiments, a suitable light-responsive anion channel polypeptide, e.g., SwiChR$_{CT}$, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 41; and comprises 1, 2, 3, 4, 5, 6, 7, 8, or 9 of: S98, S129, S140, S162, K156, R173, N285, K281, and Q297; and includes T167. In some embodiments, a suitable light-responsive anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO: 41; and includes S98, S129, S140, S162, K156, R173, N285, K281, and Q297; and includes T167, where the amino acid numbering is as set forth in SEQ ID NO: 41. In some embodiments, a light-responsive anion channel polypeptide comprises the amino acid sequence provided in SEQ ID NO: 5. In some of these embodiments, the light-responsive polypeptide exhibits prolonged stability of photocurrents. In some embodiments, the first 50 amino acids are replaced with MDYGGALSAVG (SEQ ID NO: 55). In any one of these embodiments, a suitable anion channel polypeptide comprises a membrane trafficking signal (e.g., KSRITSEGEYIPLDQIDINV (SEQ ID NO: 56)). In any one of these embodiments, a suitable anion channel polypeptide comprises an ER export signal (e.g., FCYENEV (SEQ ID NO: 61)). In any one of these embodiments, a suitable anion channel polypeptide comprises both a membrane trafficking signal (e.g., KSRITSEGEYIPLDQIDINV (SEQ ID NO: 56)) and an ER export signal (e.g., FCYENEV (SEQ ID NO: 61)).

In some embodiments, a suitable light-responsive anion channel polypeptide is based on the amino acid sequence of the protein C1C2, wherein the cysteine amino acid residue at position 167 has been replaced by an alanine residue. In some embodiments, a suitable light-responsive anion channel polypeptide, SwiChR$_{CA}$, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO: 41; and includes 1, 2, 3, 4, 5, 6, 7, 8, or 9 of: S98, S129, S140, S162, K156, R173, N285, K281, and Q297; and includes A167, where the amino acid numbering is as set forth in SEQ ID NO: 41. In some embodiments, a suitable light-responsive anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO: 41; and includes S98, S129, S140, S162, K156, R173, N285, K281, and Q297; and includes A167, where the amino acid numbering is as set forth in SEQ ID NO: 41. In some embodiments, the first 50 amino acids are replaced with MDYGGALSAVG (SEQ ID NO: 55). In any one of these embodiments, a suitable anion channel polypeptide comprises a membrane trafficking signal (e.g., KSRITSEGEYIPLDQIDINV (SEQ ID NO: 56)). In any one of these embodiments, a subject anion channel polypeptide includes an ER export signal (e.g., FCYENEV (SEQ ID NO: 61)). In any one of these embodiments, a subject anion channel polypeptide comprises both a membrane trafficking signal (e.g., KSRITSEGEYIPLDQIDINV (SEQ ID NO: 56)) and an ER export signal (e.g., FCYENEV (SEQ ID NO: 61)).

In some embodiments, a suitable light-responsive anion channel polypeptide is based on the amino acid sequence of the protein C1C2, wherein the cysteine amino acid residue at position 167 has been replaced by a serine residue. In some embodiments, a suitable light-responsive anion channel polypeptide, SwiChR$_{CS}$, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO: 41; and includes 1, 2, 3, 4, 5, 6, 7, 8, or 9 of: S98, S129, S140, S162, K156, R173, N285, K281, and Q297; and includes S167, where the amino acid numbering is as set forth in SEQ ID NO: 41. In some embodiments, a suitable light-responsive anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO: 41; and includes S98, S129, S140, S162, K156, R173, N285, K281, and Q297; and includes S167, where the amino acid numbering is as set forth in SEQ ID NO: 41. In some embodiments, the first 50 amino acids are replaced with MDYGGALSAVG (SEQ ID NO: 55). In any one of these embodiments, a suitable anion channel polypeptide comprises a membrane trafficking signal (e.g., KSRITSEGEYIPLDQIDINV (SEQ ID NO: 56)). In any one of these embodiments, a subject anion channel polypeptide includes an ER export signal (e.g., FCYENEV (SEQ ID NO: 61)). In any one of these embodiments, a subject anion channel polypeptide comprises both a membrane trafficking signal (e.g., KSRITSEGEYIPLDQIDINV (SEQ ID NO: 56)) and an ER export signal (e.g., FCYENEV (SEQ ID NO: 61)).

In certain embodiments, the SwiChR protein comprises an amino acid sequence that is at least 75%, 85%, 90%, 91%, 92%, 93%, 94%, 95%, 96%, 97%, 98%, 99%, or 100% identical to the sequence shown in SEQ ID NO: 42.

In some embodiments, a suitable light-responsive anion channel polypeptide, SwiChR, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO: 41; and includes 1, 2, 3, 4, 5, 6, 7, 8, or 9 of: S98, S129, S140, S162, K156, R173, N285, K281, and Q297; includes N195, or A195; and includes A167, where the amino acid numbering is as set forth in SEQ ID NO: 41. In some embodiments, a suitable light-responsive anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO: 41; and includes S98, S129, S140, S162, K156, R173, N285, K281, and Q297; includes A167; and includes N195, or A195, where the amino acid numbering is as set forth in SEQ ID NO: 41. In some embodiments, the first 50 amino acids are replaced with MDYGGALSAVG (SEQ ID NO: 55). In any one of these embodiments, a subject anion channel polypeptide comprises a membrane trafficking signal (e.g., KSRITSEGEYIPLDQIDINV (SEQ ID NO: 56)). In any one of these embodiments, a subject anion channel polypeptide comprises an ER export signal (e.g., FCYENEV (SEQ ID NO: 61)). In any one of these embodiments, a subject anion channel polypeptide comprises both a membrane trafficking signal (e.g., KSRITSEGEYIPLDQIDINV (SEQ ID NO: 56)) and an ER export signal (e.g., FCYENEV (SEQ ID NO: 61)).

In some embodiments, a suitable light-responsive anion channel polypeptide is based on the amino acid sequence of the protein C1C2 with one or more of the modifications described above, wherein the aspartate amino acid residue at original position 195 has been replaced by an alanine residue. In certain embodiments wherein the first 50 N-terminal amino acids of the protein are replaced by amino acids 1-11 from the protein ChR2, the aspartate amino acid residue at position 156 (which corresponds to original position 195 of the C1C2 amino acid sequence set forth in SEQ ID NO: 12) is replaced by an alanine residue.

In some embodiments, a suitable hyperpolarizing light-responsive polypeptide is based on the amino acid sequence of the protein C1C2 with one or more of the modifications described above, wherein the aspartate amino acid residue at original position 195 has been replaced by an asparagine residue. In certain embodiments wherein the first 50 N-terminal amino acids of the protein are replaced by amino acids 1-11 from the protein ChR2, the aspartate amino acid residue at position 156 (which corresponds to original position 195 of the C1C2 amino acid sequence set forth in SEQ ID NO: 12) is replaced by an asparagine residue.

In some embodiments, a suitable hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 43; and includes 1, 2, 3, 4, 5, 6, 7, 8, or 9 of: S59, S90, S101, S123, K117, R134, N246, K242, and Q258; and includes A128, T128 or S128, where the amino acid numbering is as set forth in SEQ ID NO: 43. In some embodiments, a suitable hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 43; and includes S59, S90, S101, S123, K117, R134, N246, K242, and Q258; and includes A128, T128 or S128, where the amino acid numbering is as set forth in SEQ ID NO: 43. In any one of these embodiments, a subject anion channel polypeptide comprises a membrane trafficking signal (e.g., KSRITSEGEYIPLDQIDINV (SEQ ID NO: 56)). In any one of these embodiments, a suitable anion channel polypeptide comprises an ER export signal (e.g., FCYENEV (SEQ ID NO: 61)). In any one of these embodiments, a suitable anion channel polypeptide includes both a membrane trafficking signal (e.g., KSRITSEGEYIPLDQIDINV (SEQ ID NO: 56)) and an ER export signal (e.g., FCYENEV (SEQ ID NO: 61)).

Anion Channel Proteins Based on ChR2

In some embodiments, a suitable hyperpolarizing light-responsive polypeptide is based on the amino acid sequence of the protein ChR2. The amino acid sequence of ChR2 is set forth in SEQ ID NO: 4. In some embodiments, the amino acid sequence of the ChR2 protein has been modified by introducing one or more of the following mutations into the amino acid sequence: A59S, E90S, E101S, E123S, Q117K, H134R, V242K, T246N and/or N258Q. In some embodiments, a suitable hyperpolarizing light-responsive polypeptide comprises the amino acid sequence of the protein ChR2 with all 9 of the above-listed amino acid substitutions, such that the amino acid sequence of the polypeptide is provided in SEQ ID NO: 45 (iChR2).

In some embodiments, a suitable light-responsive anion channel polypeptide iChR2 comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 45; and includes 1, 2, 3, 4, 5, 6, 7, 8, or 9 amino acid substitutions selected from A59S, E90S, E101S, E123S, Q117K, H134R, V242K, T246N and/or N258Q, relative to the amino acid sequence of ChR2 (SEQ ID NO: 4).

In some embodiments, a suitable light-responsive polypeptide ("iChR2") comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 45; and includes 1, 2, 3, 4, 5, 6, 7, 8, or 9 of: S59, S90, S101, S123, K117, R134, K242, N246 and Q258, where the amino acid numbering is as set forth in SEQ ID NO: 45. In some embodiments, an iChR2 polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 45; and includes 1, 2, 3, 4, 5, 6, 7, 8, 9, 10 or 11 of: S59, S90, S101, S123, K117, R134, K242, N246, Q258, and either N156 or A156, and either T128, A128, or S128, where the amino acid numbering is as set forth in SEQ ID NO: 45. In some embodiments, an iChR2 polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 45; and includes S59, S90, S101, S123, K117, R134, K242, N246 and Q258, where the amino acid numbering is as set forth in SEQ ID NO: 45. In any one of these embodiments, an iChR2 polypeptide can comprise a membrane trafficking signal (e.g., KSRITSEGEYIPLDQIDINV (SEQ ID NO: 56)). In any one of these embodiments, an iChR2 polypeptide can comprise an ER export signal (e.g., FCYENEV (SEQ ID NO: 61)). In any one of these embodiments, an iChR2 polypeptide can comprise both a membrane trafficking signal (e.g., KSRITSEGEYIPLDQIDINV (SEQ ID NO: 56)) and an ER export signal (e.g., FCYENEV (SEQ ID NO: 61)). Thus in certain embodiments, the iChR2 protein comprises an amino acid sequence that is at least 75%, 85%, 90%, 91%, 92%, 93%, 94%, 95%, 96%, 97%, 98%, 99%, or 100% identical to the sequence shown in SEQ ID NO: 46.

Anion Channel Polypeptides Based on C1V1

In some embodiments, a suitable hyperpolarizing light-responsive polypeptide is based on the amino acid sequence of the protein C1V1. The amino acid sequence of C1V1 is set forth in SEQ ID NO: 10. In some embodiments, the amino acid sequence of the C1V1 protein has been modified by introducing one or more of the following mutations into the amino acid sequence: T98S, E129S, E140S, E162S, V156K, H173R, A285N, P281K and/or N297Q. In some embodiments, a hyperpolarizing light-responsive polypeptide comprises the amino acid sequence of the protein C1V1 with all 9 of the above-listed amino acid substitutions, such that the amino acid sequence of the polypeptide is provided in SEQ ID NO: 47.

In some embodiments, a suitable light-responsive anion channel polypeptide, iC1V1, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 47; and includes 1, 2, 3, 4, 5, 6, 7, 8, or 9 amino acid substitutions selected from T98S, E129S, E140S, E162S, V156K, H173R, A285N, P281K and/or N297Q, relative to the amino acid sequence of C1V1 (SEQ ID NO: 10).

In some embodiments, a suitable light-responsive anion channel polypeptide, iC1V1, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 47; and includes 1, 2, 3, 4, 5, 6, 7, 8, or 9 of: S98, S129, S140, S162, K156, R173, N285, K281, and Q297, where the amino acid numbering is as set forth in SEQ ID NO: 47. In some embodiments, a suitable light-responsive anion channel polypeptide (referred to as "iC1V1"), comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 47; and includes 1, 2, 3, 4, 5, 6, 7, 8, or 9 of: S98, S129, S140, S162, K156, R173, N285, K281, and Q297, and includes N195, where the amino acid numbering is as set forth in SEQ ID NO: 47. In some embodiments, a suitable light-responsive anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 47; and includes S98, S129, S140, S162, K156, R173, N285, K281, and Q297, where the amino acid numbering is as set forth in SEQ ID NO: 47. In any one of these embodiments, a suitable anion channel polypeptide includes a membrane trafficking signal (e.g., KSRITSEGEYIPLDQIDINV (SEQ ID NO: 56)). In any one of these embodiments, a subject anion channel polypeptide includes an ER export signal (e.g., FCYENEV (SEQ ID NO: 61)). In any one of these embodiments, a suitable anion channel polypeptide comprises both a membrane trafficking signal (e.g., KSRITSEGEYIPLDQIDINV (SEQ ID NO: 56)) and an ER export signal (e.g., FCYENEV (SEQ ID NO: 61)). Thus in certain embodiments, the iC1V1 protein can have an amino acid sequence that is at least 75%, 85%, 90%, 91%, 92%, 93%, 94%, 95%, 96%, 97%, 98%, 99%, or 100% identical to the sequence shown in SEQ ID NO: 48.

In some embodiments, a suitable hyperpolarizing light-responsive polypeptide is based on the amino acid sequence of the protein C1V1 (SEQ ID NO: 10), wherein the amino acid sequence has been modified by replacing the first 50 N-terminal amino acids of C1V1 with amino acids 1-11 from the protein ChR2 (MDYGGALSAVG) (SEQ ID NO: 55). In some embodiments, a suitable hyperpolarizing light-responsive polypeptide, ibC1V1, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 49; and includes 1, 2, 3, 4, 5, 6, 7, 8, or 9 of: S59, S90, S101, S123, K117, R134, N246, K242, and Q258, where the amino acid numbering is as set forth in SEQ ID NO: 49. In some embodiments, a suitable hyperpolarizing light-responsive polypeptide (referred to as "ibC1V1"), comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 49; and includes 1, 2, 3, 4, 5, 6, 7, 8, or 9 of: S59, S90, S101, S123, K117, R134, N246, K242, and Q258, and includes N156, where the amino acid numbering is as set forth in SEQ ID NO: 49. In some embodiments, a suitable hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 49; and includes S59, S90, S101, S123, K117, R134, N246, K242, and Q258, where the amino acid numbering is as set forth in SEQ ID NO: 49. In some embodiments, a suitable light-responsive anion channel polypeptide comprises the amino acid sequence set forth in SEQ ID NO: 49. In any one of these embodiments, a suitable anion channel polypeptide comprises a membrane trafficking signal (e.g., KSRITSEGEYIPLDQIDINV (SEQ ID NO: 56)). In any one of these embodiments, a suitable anion channel polypeptide comprises an ER export signal (e.g., FCYENEV (SEQ ID NO: 61)). In any one of these embodiments, a subject anion channel polypeptide comprises both a membrane trafficking signal (e.g., KSRITSEGEYIPLDQIDINV (SEQ ID NO:

56)) and an ER export signal (e.g., FCYENEV (SEQ ID NO: 61)). Thus in certain embodiments, an ibC1V1 protein comprises an amino acid sequence that is at least 75%, 85%, 90%, 91%, 92%, 93%, 94%, 95%, 96%, 97%, 98%, 99%, or 100% identical to the sequence shown in SEQ ID NO: 50.

In some embodiments, a suitable hyperpolarizing light-responsive polypeptide is based on the amino acid sequence of the protein C1V1 (SEQ ID NO: 10), wherein the cysteine amino acid residue at position 167 has been replaced by a threonine residue. In some embodiments, a suitable hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO: 47; and includes 1, 2, 3, 4, 5, 6, 7, 8, or 9 of: S98, S129, S140, S162, K156, R173, N285, K281, and Q297; and includes T167. In some embodiments, a suitable hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO: 47; and includes S98, S129, S140, S162, K156, R173, N285, K281, and Q297; and includes T167, S167 or A167, where the amino acid numbering is as set forth in SEQ ID NO: 47. In some embodiments, a suitable hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO: 47; and includes S98, S129, S140, S162, K156, R173, N285, K281, and Q297; includes T167, S167 or A167; and includes A195 or N195, where the amino acid numbering is as set forth in SEQ ID NO: 47. In some embodiments, the first 50 amino acids are replaced with MDYGGALSAVG (SEQ ID NO: 55). In any one of these embodiments, a suitable hyperpolarizing light-responsive polypeptide comprises a membrane trafficking signal (e.g., KSRITSEGEYIPLDQIDINV (SEQ ID NO: 56)). In any one of these embodiments, a suitable hyperpolarizing light-responsive polypeptidecomprises an ER export signal (e.g., FCYENEV (SEQ ID NO: 61)). In any one of these embodiments, a suitable hyperpolarizing light-responsive polypeptide includes both a membrane trafficking signal (e.g., KSRITSEGEYIPLDQIDINV (SEQ ID NO: 56)) and an ER export signal (e.g., FCYENEV (SEQ ID NO: 61)).

In some embodiments, a suitable hyperpolarizing light-responsive polypeptide is based on the amino acid sequence of the protein C1V1 with one or more of the modifications described above, wherein the aspartate amino acid residue at original position 195 has been replaced by an alanine residue. In certain embodiments wherein the first 50 N-terminal amino acids of the protein are replaced by amino acids 1-11 from the protein ChR2, the aspartate amino acid residue at position 156 (which corresponds to original position 195 of the C1V1 amino acid sequence set forth in SEQ ID NO: 10) is replaced by an alanine residue.

In some embodiments, a suitable hyperpolarizing light-responsive polypeptide is based on the amino acid sequence of the protein C1V1 with one or more of the modifications described above, wherein the aspartate amino acid residue at original position 195 has been replaced by an asparagine residue. In certain embodiments wherein the first 50 N-terminal amino acids of the protein are replaced by amino acids 1-11 from the protein ChR2, the aspartate amino acid residue at position 156 (which corresponds to original position 195 of the C1V1 amino acid sequence set forth in SEQ ID NO: 10) is replaced by an asparagine residue.

In some embodiments, a suitable hyperpolarizing light-responsive polypeptide, ibC1V1, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 49; and includes 1, 2, 3, 4, 5, 6, 7, 8, or 9 of: S59, S90, S101, S123, K117, R134, N246, K242, and Q258; and includes T128, A128, or S128, where the amino acid numbering is as set forth in SEQ ID NO: 49. In some embodiments, a suitable hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 49; and includes S59, S90, S101, S123, K117, R134, N246, K242, and Q258; and includes T128, A128, or S128, where the amino acid numbering is as set forth in SEQ ID NO: 49. In any one of these embodiments, a suitable anion channel polypeptide comprises a membrane trafficking signal (e.g., KSRITSEGEYIPLDQIDINV (SEQ ID NO: 56)). In any one of these embodiments, a suitable anion channel polypeptide comprises an ER export signal (e.g., FCYENEV (SEQ ID NO: 61)). In any one of these embodiments, a suitable anion channel polypeptide comprises both a membrane trafficking signal (e.g., KSRITSEGEYIPLDQIDINV (SEQ ID NO: 56)) and an ER export signal (e.g., FCYENEV (SEQ ID NO: 61)).

In some embodiments, a suitable hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 49; and includes 1, 2, 3, 4, 5, 6, 7, 8, or 9 of: S59, S90, S101, S123, K117, R134, N246, K242, and Q258; and includes T128, A128, or S128; and includes A156 or N156, where the amino acid numbering is as set forth in SEQ ID NO: 49. In some embodiments, a suitable hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 49; and includes S59, S90, S101, S123, K117, R134, N246, K242, and Q258; and includes T128, A128, or S128; and includes A156 or N156, where the amino acid numbering is as set forth in SEQ ID NO: 49. In any one of these embodiments, a suitable hyperpolarizing light-responsive polypeptide comprises a membrane trafficking signal (e.g., KSRITSEGEYIPLDQID-INV (SEQ ID NO: 56)). In any one of these embodiments, a suitable hyperpolarizing light-responsive polypeptide comprises an ER export signal (e.g., FCYENEV (SEQ ID NO: 61)). In any one of these embodiments, a subject anion channel polypeptide includes both a membrane trafficking signal (e.g., KSRITSEGEYIPLDQIDINV (SEQ ID NO: 56)) and an ER export signal (e.g., FCYENEV (SEQ ID NO: 61)).

Anion Channel Polypeptides Based on ReaChR

In some embodiments, a subject hyperpolarizing light-responsive polypeptide is based on the amino acid sequence of the protein ReaChR. The amino acid sequence of ReaChR is set forth in SEQ ID NO: 14. In some embodiments, the amino acid sequence of the ReaChR protein has been modified by introducing one or more of the following mutations into the amino acid sequence: T99S, E130S, E141S, E163S, V157K, H174R, A286N, P282K and/or N298Q. In some embodiments, a subject hyperpolarizing light-responsive polypeptide comprises the amino acid sequence of the protein ReaChR with all 9 of the above-listed amino acid substitutions, such that the amino acid sequence of the polypeptide is provided in SEQ ID NO: 51.

In some embodiments, a subject light-responsive anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 51; and includes 1, 2, 3, 4, 5, 6, 7, 8, or 9 amino acid substitutions selected from T99S, E130S, E141S, E163S, V157K, H174R, A286N, P282K and/or N298Q, relative to the amino acid sequence of ReaChR (SEQ ID NO: 14).

In some embodiments, a subject light-responsive anion channel polypeptide, iReaChR, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 51; and includes 1, 2, 3, 4, 5, 6, 7, 8, or 9 of: S99, S130, S141, S163, K157, R174, N286, K281, and Q298, where the amino acid numbering is as set forth in SEQ ID NO: 51. In some embodiments, a subject light-responsive anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 51; and includes S99, S130, S141, S163, K157, R174, N286, K281, and Q298, where the amino acid numbering is as set forth in SEQ ID NO: 51. In any one of these embodiments, a subject anion channel polypeptide comprises a membrane trafficking signal (e.g., KSRITSEGEYIPLDQIDINV (SEQ ID NO: 56)). In any one of these embodiments, a subject anion channel polypeptide comprises an ER export signal (e.g., FCYENEV (SEQ ID NO: 61)). In any one of these embodiments, a subject anion channel polypeptide includes both a membrane trafficking signal (e.g., KSRITSEGEYIPLDQIDINV (SEQ ID NO: 56)) and an ER export signal (e.g., FCYENEV (SEQ ID NO: 61)). Thus in certain embodiments, the iReaChR protein comprises an amino acid sequence that is at least 75%, 85%, 90%, 91%, 92%, 93%, 94%, 95%, 96%, 97%, 98%, 99%, or 100% identical to the sequence shown in SEQ ID NO: 52.

In some embodiments, a subject light-responsive anion channel polypeptide, iReaChR, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 51; and includes 1, 2, 3, 4, 5, 6, 7, 8, or 9 of: S99, S130, S141, S163, K157, R174, N286, K281, and Q298, and includes N196, where the amino acid numbering is as set forth in SEQ ID NO: 51. In some embodiments, a subject light-responsive anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 51; and includes S99, S130, S141, S163, K157, R174, N286, K281, and Q298, and includes N196, where the amino acid numbering is as set forth in SEQ ID NO: 51. In any one of these embodiments, a subject anion channel polypeptide comprises a membrane trafficking signal (e.g., KSRITSEGEYIPLDQIDINV (SEQ ID NO: 56)). In any one of these embodiments, a subject anion channel polypeptide comprises an ER export signal (e.g., FCYENEV (SEQ ID NO: 61)). In any one of these embodiments, a subject anion channel polypeptide comprises both a membrane trafficking signal (e.g., KSRITSEGEYIPLDQIDINV (SEQ ID NO: 56)) and an ER export signal (e.g., FCYENEV (SEQ ID NO: 61)).

In some embodiments, a subject hyperpolarizing light-responsive polypeptide is based on the amino acid sequence of the protein ReaChR (SEQ ID NO: 14), wherein the amino acid sequence has been modified by replacing the first 51 N-terminal amino acids of ReaChR with amino acids 1-11 from the protein ChR2 (MDYGGALSAVG) (SEQ ID NO: 55). In some embodiments, a subject hyperpolarizing light-responsive polypeptide, ibReaChR, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 53; and includes 1, 2, 3, 4, 5, 6, 7, 8, or 9 of: S59, S90, S101, S123, K117, R134, N246, K242, and Q258, where the amino acid numbering is as set forth in SEQ ID NO: 53. In some embodiments, a subject hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 53; and includes S59, S90, S101, S123, K117, R134, N246, K242, and Q258, where the amino acid numbering is as set forth in SEQ ID NO: 53. In some embodiments, a subject light-responsive anion channel polypeptide comprises the amino acid sequence set forth in SEQ ID NO: 53. In any one of these embodiments, a subject anion channel polypeptide comprises a membrane trafficking signal (e.g., KSRITSEGEYIPLDQIDINV (SEQ ID NO: 56)). In any one of these embodiments, a subject anion channel polypeptide comprises an ER export signal (e.g., FCYENEV (SEQ ID NO: 61)). In any one of these embodiments, a subject anion channel polypeptide comprises both a membrane trafficking signal (e.g., KSRITSEGEYIPLDQIDINV (SEQ ID NO: 56)) and an ER export signal (e.g., FCYENEV (SEQ ID NO: 61)). Thus in certain embodiments, the ibReaChR protein can have an amino acid sequence that is at least 75%, 85%, 90%, 91%, 92%, 93%, 94%, 95%, 96%, 97%, 98%, 99%, or 100% identical to the sequence shown in SEQ ID NO: 54.

In some embodiments, a subject hyperpolarizing light-responsive polypeptide is based on the amino acid sequence of the protein ReaChR (SEQ ID NO: 14), wherein the amino acid sequence has been modified by replacing the first 51 N-terminal amino acids of ReaChR with amino acids 1-11 from the protein ChR2 (MDYGGALSAVG) (SEQ ID NO: 55). In some embodiments, a subject hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 53; and includes 1, 2, 3, 4, 5, 6, 7, 8, or 9 of: S59, S90, S101, S123, K117, R134, N246, K242, and Q258, and includes N156, where the amino acid numbering is as set forth in SEQ ID NO: 53. In some embodiments, a subject hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 53; and includes S59, S90, S101, S123, K117, R134, N246, K242, and Q258, and includes N156, where the amino acid numbering is as set forth in SEQ ID NO: 53. In any one of these embodiments, a subject anion channel polypeptide comprises a membrane trafficking signal (e.g., KSRITSEGEYIPLDQIDINV (SEQ ID NO: 56)). In any one of these embodiments, a subject anion channel polypeptide comprises an ER export signal (e.g., FCYENEV (SEQ ID NO: 61)). In any one of these embodiments, a subject anion channel polypeptide comprises both a membrane trafficking signal (e.g., KSRITSEGEYIPLDQIDINV (SEQ ID NO: 56)) and an ER export signal (e.g., FCYENEV (SEQ ID NO: 61)).

In some embodiments, a subject hyperpolarizing light-responsive polypeptide is based on the amino acid sequence of the protein ReaChR (SEQ ID NO: 14), wherein the cysteine amino acid residue at position 168 has been replaced by a threonine residue. In some embodiments, a subject hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO: 51; and includes 1, 2, 3, 4, 5, 6, 7, 8, or 9 of: S99, S130, S141, S163, K157, R174, N286, K281, and Q298; and includes T168, S168 or A168. In some embodiments, a subject hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO: 60; and includes S99, S130, S141, S163, K157, R174, N286, K281, and Q298; and includes T168, S168 or A168, where the amino acid numbering is as set forth in SEQ ID NO: 51. In some embodiments, the first 51 amino acids are replaced with MDYGGALSAVG (SEQ ID NO: 55). In any one of these embodiments, a subject anion channel polypeptide comprises a membrane trafficking signal (e.g., KSRITSEGEYIPLDQIDINV (SEQ ID NO: 56)). In any one of these embodiments, a subject anion channel polypeptide comprises an ER export signal (e.g., FCYENEV (SEQ ID NO: 61)). In any one of these embodiments, a subject anion channel polypeptide comprises both a membrane trafficking signal (e.g., KSRITSEGEYIPLDQIDINV (SEQ ID NO: 56)) and an ER export signal (e.g., FCYENEV (SEQ ID NO: 61)).

In some embodiments, a subject hyperpolarizing light-responsive polypeptide, iReaChR, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 51; and includes 1, 2, 3, 4, 5, 6, 7, 8, or 9 of: S99, S130, S141, S163, K157, R174, N286, K281, and Q298; includes A196 or N196; and includes T168, S168, or A168, where the amino acid numbering is as set forth in SEQ ID NO: 51. In some embodiments, a subject hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO: 51; and includes S99, S130, S141, S163, K157, R174, N286, K281, and Q298; includes A196 or N196; and includes T168, S168, or A168, where the amino acid numbering is as set forth in SEQ ID NO: 51. In some embodiments, the first 51 amino acids are replaced with MDYGGALSAVG (SEQ ID NO: 55). In any one of these embodiments, a subject anion channel polypeptide comprises a membrane trafficking signal (e.g., KSRITSEGEYIPLDQIDINV (SEQ ID NO: 56)). In any one of these embodiments, a subject anion channel polypeptide comprises an ER export signal (e.g., FCYENEV (SEQ ID NO: 61)). In any one of these embodiments, a subject anion channel polypeptide includes both a membrane trafficking signal (e.g., KSRITSEGEYIPLDQIDINV (SEQ ID NO: 56)) and an ER export signal (e.g., FCYENEV (SEQ ID NO: 61)).

In some embodiments, a subject hyperpolarizing light-responsive polypeptide is based on the amino acid sequence of the protein ReaChR with one or more of the modifications described above, wherein the aspartate amino acid residue at original position 196 has been replaced by an alanine residue. In certain embodiments wherein the first 51 N-terminal amino acids of the protein are replaced by amino acids 1-11 from the protein ChR2, the aspartate amino acid residue at position 156 (which corresponds to original position 196 of the ReaChR amino acid sequence set forth in SEQ ID NO: 14) is replaced by an alanine residue.

In some embodiments, a subject hyperpolarizing light-responsive polypeptide is based on the amino acid sequence of the protein ReaChR with one or more of the modifications described above, wherein the aspartate amino acid residue at original position 196 has been replaced by an asparagine residue. In certain embodiments wherein the first 51 N-terminal amino acids of the protein are replaced by amino acids 1-11 from the protein ChR2, the aspartate amino acid residue at position 156 (which corresponds to original position 196 of the ReaChR amino acid sequence set forth in SEQ ID NO: 14) is replaced by an asparagine residue.

In some embodiments, a subject hyperpolarizing light-responsive polypeptide, ibReaChR, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 53; and includes 1, 2, 3, 4, 5, 6, 7, 8, or 9 of: S59, S90, S101, S123, K117, R134, N246, K242, and Q258; and includes T128, S128 or A128, where the amino acid numbering is as set forth in SEQ ID NO: 53. In some embodiments, a subject hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 53; and includes S59, S90, S101, S123, K117, R134, N246, K242, and Q258; and includes T128, where the amino acid numbering is as set forth in SEQ ID NO: 53. In any one of these embodiments, a subject anion channel polypeptide comprises a membrane trafficking signal (e.g., KSRITSEGEYIPLDQIDINV (SEQ ID NO: 56)). In any one of these embodiments, a subject anion channel polypeptide comprises an ER export signal (e.g., FCYENEV (SEQ ID NO: 61)). In any one of these embodiments, a subject anion channel polypeptide comprises both a membrane trafficking signal (e.g., KSRITSEGEYIPLDQIDINV (SEQ ID NO: 56)) and an ER export signal (e.g., FCYENEV (SEQ ID NO: 61)).

In some embodiments, a subject hyperpolarizing light-responsive polypeptide, ibReaChR, includes an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 53; and includes 1, 2, 3, 4, 5, 6, 7, 8, or 9 of: S59, S90, S101, S123, K117, R134, N246, K242, and Q258; includes T128, S128 or A128; and includes A156 or N156, where the amino acid numbering is as set forth in SEQ ID NO: 53. In some embodiments, a subject hyperpolarizing light-responsive polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO: 53; and includes S59, S90, S101, S123, K117, R134, N246, K242, and Q258; includes T128, S128 or A128; and includes A156 or N156, where the amino acid numbering is as set forth in SEQ ID NO: 53. In any one of these embodiments, a subject anion channel polypeptide comprises a membrane trafficking signal (e.g., KSRITSEGEYIPLDQIDINV (SEQ ID NO: 56)). In any one of these embodiments, a subject anion channel polypeptide includes an ER export signal (e.g., FCYENEV (SEQ ID NO: 61)). In any one of these embodiments, a subject anion channel polypeptide comprises both a membrane trafficking signal (e.g., KSRITSEGEYIPLDQIDINV (SEQ ID NO: 56)) and an ER export signal (e.g., FCYENEV (SEQ ID NO: 61)).

Expression Vector

As noted above, aspects of the present disclosure include a recombinant expression vector comprising a nucleic acid that includes a D2SP. Suitable expression vectors include vectors comprising a nucleotide sequence that encodes an RNA (e.g., an mRNA) that when transcribed from the polynucleotides of the vector will result in the expression of a subject gene product. In some cases, the gene product is a polypeptide. In some cases, the gene product encoded in the expression vector is a light-responsive polypeptide that is expressed on the plasma membranes of the target cells. In other instances, the gene product encoded in the expression vector is a fluorescent protein that is expressed in the cytosol of the target cells. Vectors which may be used include, without limitation, lentiviral, herpes simplex virus, adenoviral, and adeno-associated virus (AAV) vectors. Lentiviral vectors include, but are not limited to human immunodeficiency virus (HIV)-based vectors. Lentiviral vectors may be pseudotyped with the envelope proteins of other viruses, including, but not limited to vesicular stomatitis virus (VSV), rabies, Mo-murine leukemia virus (MLV), baculovirus and Ebola. Such vectors may be prepared using standard methods in the art.

Other vectors of interest include plasmid vectors. The term plasmid as used herein can refer to nucleic acid, e.g., DNA derived from a plasmid vector, cosmid, phagemid or bacteriophage, into which one or more fragments of nucleic acid may be inserted or cloned which encode for particular genes. This includes the construction comprised of extrachromosomal genetic material, usually of a circular duplex of DNA which can replicate independently of chromosomal DNA in a host cell.

In certain embodiments, the recombinant expression vector comprises multiple cloning sites that facilitate subcloning a nucleotide sequence encoding a gene product of interest into the recombinant expression vector, thereby operably linking the nucleotide sequence encoding the gene product of interest to the D2SP.

In some embodiments, a vector may be a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and comprises an inverted terminal repeat (ITR) region of approximately 145 bases at each end, which serves as an origin of replication for the virus. The remainder of the genome is divided into two essential regions that carry the encapsidation functions: the left-hand part of the genome that comprises the rep gene involved in viral replication and expression of the viral genes; and the right-hand part of the genome that contains the cap gene encoding the capsid proteins of the virus.

AAV vectors may be prepared using standard methods in the art. Adeno-associated viruses of any serotype are suitable (see, e.g., Blacklow, pp. 165-174 of "Parvoviruses and Human Disease" J. R. Pattison, ed. (1988); Rose, Comprehensive Virology 3:1, 1974; P. Tattersall "The Evolution of Parvovirus Taxonomy" In Parvoviruses (J R Kerr, S F Cotmore. M E Bloom, R M Linden, C R Parrish, Eds.) p 5-14, Hudder Arnold, London, U K (2006); and D E Bowles, J E Rabinowitz, R J Samulski "The Genus Dependovirus" (J R Kerr, S F Cotmore. M E Bloom, R M Linden, C R Parrish, Eds.) p 15-23, Hudder Arnold, London, U K (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication-defective recombinant AAVs according to the present disclosure can be prepared by co-transfecting a plasmid comprising the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the present disclosure are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596,535, the disclosure of which is hereby incorporated by reference in its entirety. In some cases, AAV6 is used. In some cases, AAV1 is used.

In some embodiments, the subject D2SP can be operably linked to nucleotide sequences encoding various light-responsive polypeptides (LRP), fluorescent proteins (XFP) and genetically encoded indicators (GEI) for targeting D2 receptor-expressing neuronal populations in mammalian brains. For example, the following adeno associated vectors (AAVs) and components thereof may be used without limitation: AAV-D2SP-LRP-XFP, AAV-D2SP-GEI, AAV-D2SP-FLEX-LRP-XFP, AAV-D2SP-FLEX-GEI. Other AAV vectors that may be used in association with the polynucleotides include those with double floxed inverted reading frames (DIO) which allow expression of proteins under the control of recombinases such as as Cre and Flp: AAV-D2SP-DIO(Cre)-LRP-XFP (Cre-dependent expression), AAV-D2SP-DIO(Flp)-LRP-XFP (Flp-dependent expression), AAV-D2SP-DIO(Cre)-DIO(Flp)-LRP-XFP (Cre and Flp dependent expression).

Genetically Modified Host Cell

The present disclosure provides isolated genetically modified host cells (e.g., in vitro cells) that are genetically modified with a subject nucleic acid. In some embodiments, a subject isolated genetically modified host cell can produce a gene product encoded by a nucleotide sequence operably linked to a D2SP of the present disclosure.

Suitable host cells include eukaryotic host cells, such as a mammalian cell. Mammalian cells of interest include human cells, rodent cells, such as rat cells and mouse cells. Introduction of a subject nucleic acid into the host cell can be effected, for example by calcium phosphate precipitation, DEAE dextran mediated transfection, liposome-mediated transfection, electroporation, viral infection, or other known method.

Suitable mammalian cells include primary cells and progenitor cells, such as stem cells. In some cases, the mammalian cell is a neuron, e.g., a non-immortalized (primary) neuron. In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S(ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

In some instances, the host cell is a progenitor cell or a stem cell. "Stem cell," as used herein, refers to a cell having, upon being induced, both the ability to differentiate into multiple lineages of cells (multipotency or pluripotency) and the ability to maintain its multipotency or pluripotency after cell division (ability to self-renew). Stem cells encompass, for example, hematopoietic stem cells, neural stem cells, hepatic stem cells, dermal stem cells, germ stem cells, and embryonic stem (ES) or induced pluripotent stem (iPS) cells, and stem cells induced from these cells, etc. Stem cells can be obtained from embryonic, post-natal, juvenile or adult tissue. The "progenitor cell" refers to an undifferentiated cell derived from a stem cell, and is not itself a stem cell. Some progenitor cells can produce progeny that are capable of differentiating into more than one cell type.

In some embodiments, the host cell is a human ES cell. In certain embodiments, the human ES cell can be differentiated into a neuron. Any suitable method for growing and inducing differentiation of ES cells may be used, some of which are described in, e.g., U.S. Pat. Nos. 8,460,931 and 7,892,835; US App. Pub. No. 20130252335 and 20100075416; PCT App. Pub. No. WO2001/088100; and Kawasaki et al. Neuron 2000 28:31, which are incorporated herein by reference. In other embodiments, the host cell is an iPS cell, which are described in further detail in, e.g., PCT App. Pub. No. WO2007/069666, which is incorporated herein by reference.

Methods

As summarized above, aspects of the present disclosure include a method of introducing into a target cell a nucleic acid that includes a D2SP operably linked to a gene product that, when expressed, performs a function of interest, e.g., light-induced depolarization/hyperpolarization and/or fluorescent labeling. Introducing the nucleic acid into a target cell may be done by any convenient method, as described above for a genetically modified host cell. The target cell may be in in vitro culture, or may be located in vivo, e.g., a cell in a tissue in vivo, such as a neuronal cell in the brain.

In certain embodiments, the target cell is a progenitor cell, such as a neural progenitor cell. In some instances, the target cell is a stem cell. Any convenient method for introducing a nucleic acid into a progenitor cell or stem cell may be used to introduce a nucleic acid that includes a D2SP operably linked to a gene product, as described above with respect to a genetically modified host cell.

In some embodiments, a target neuron is, e.g., a sensory neuron, a motor neuron, or an interneuron. Target neurons of the disclosure may include neurons of the central nervous system and/or cells of the peripheral nervous system. In some embodiments, a target tissue may include a plurality of nerve fibers, a nerve, a nerve cell ganglion, a neuromuscular junction, a tissue that is innervated by nerves, including but not limited to muscle, skin, or endocrine tissue, or an anatomical region, such as a portion or sub-portion of the brain or spinal cord. In some embodiments, a target tissue may be a portion of an individual cell, such as a specific axon of a nerve cell.

Exemplary target cells, brain regions and tissues include but not limited to: basal ganglia, nucleus accumbens, cortex, habenula, ventral tegmental area, substantia nigra, olfactory tubercle, septum, amygdala, hippocampus, cerebellum, thalamus, chemoreceptor trigger zone, pituitary gland, hypothalamus, sympathetic ganglia, adrenal glands, peripheral afferent nerves, enteric nerves, gastrointestinal mucosa, heart, pulmonary tissues, vascular tissue, renal cortex and inner medulla of the kidney, and glioblastomas.

A nucleic acid comprising a nucleotide sequence encoding a gene product operably linked to a D2SP can be introduced into a neuron by any convenient means. For example, a nucleic acid comprising a nucleotide sequence encoding a gene product operably linked to a D2SP can be introduced (e.g., injected) into a nerve bundle or nerve fiber, such that the nucleic acid enters a neuron, where the gene product operably linked to a D2SP is produced in the neuron. A nucleic acid comprising a nucleotide sequence encoding a gene product operably linked to a D2SP can be introduced (e.g., injected) proximal to a nerve. Stereotactic injection can be used; see, e.g., Stein et al., *J. Virol,* 73:34243429, 1999; Davidson et al., *PNAS,* 97:3428-3432, 2000; Davidson et al., *Nat. Genet.* 3:219-223, 1993; and Alisky & Davidson, *Hum. Gene Ther.* 11:2315-2329, 2000, the contents of each of which are hereby incorporated by reference herein in their entireties.

Once the subject polynucleotides have been delivered to a target neuron or tissue, the polynucleotides enter the target cells and are expressed. In some embodiments, expression from the subject nucleic acids only occurs in target cells wherein the D2SP is active. In this way, if a subject polynucleotide is delivered to cells other than a target cell, the polynucleotide will not be expressed in the non-target cells because the D2SP will be inactive in those cells. In some instances, the D2SP drives expression of a gene product operably linked thereto with a high specificity. Specificity of a promoter can be expressed as the number of cells expressing a gene product operably linked to the promoter and staining positively with an antibody specific to the D2 receptor (such as Millipore ab1558; FIG. 3), divided by the total number of cells expressing the gene product operably linked to the promoter. In some instances, the D2SP drives expression of a gene product operably linked thereto with a specificity of 91% or more, e.g., 92% or more, 93% or more, 94% or more, 95% or more, 95.5% or more, 96% or more, 96.5% or more, 97% or more, 97.5% or more, 98% or more, 98.1% or more, 98.2% or more, 98.3% or more, 98.4% or more, or 98.5% or more. In some instances, the D2SP drives expression of a gene product operably linked thereto with a specificity of 99% or less, e.g., 99.5% or less, 99.3% or less, 99.1% or less, 99.0% or less, 98.9% or less, 98.8% or less, 98.7% or less, 98.6% or less, 98.5% or less, 98.4% or less, 98.3% or less, or 98.2%. In some instances, the D2SP drives expression of a gene product operably linked thereto with a specificity in the range of 91 to 99%, e.g., 92 to 99%, including 93 to 99%, 94 to 98.5%, or 95 to 98.5%. In some instances, the D2SP drives expression of a gene product operably linked thereto with a specificity of about 98.2%.

In some instances, the D2SP drives expression of a gene product operably linked thereto with a percentage specificity that is higher than the percentage specificity of expression of the gene product driven by a conventional D2 receptor promoter, e.g. a D2 receptor promoter that includes exon 1 of the D2 receptor gene, such as a nucleic acid having a sequence at least 90%, e.g., at least 95%, at least 98%, at least 99% or 100% identical to the sequence shown in SEQ ID NO: 2 (FIG. 2), by 5% or more, e.g., 6% or more, 7% or more, 8% or more, including 9% or more. In some instances, the D2SP drives expression of a gene product operably linked thereto with a percentage specificity that is higher than the percentage specificity of expression of the gene product driven by a conventional D2 receptor promoter, e.g. a D2 receptor promoter that includes exon 1 of the D2 receptor gene, such as a nucleic acid having a sequence at least 90%, e.g., at least 95%, at least 98%, at least 99% or 100% identical to the sequence shown in SEQ ID NO: 2 (FIG. 2), by 9% or less, e.g., 9.5% or less, 9.0% or less, 8.5% or less, including 8% or less. In some instances, the D2SP drives expression of a gene product operably linked thereto with a percentage specificity that is higher than the percentage specificity of expression of the gene product driven by a conventional D2 receptor promoter, e.g. a D2 receptor promoter that includes exon 1 of the D2 receptor gene, such as a nucleic acid having a sequence at least 90%, e.g., at least 95%, at least 98%, at least 99% or 100% identical to the sequence shown in SEQ ID NO: 2 (FIG. 2), in the range of 5 to 9%, e.g., 6 to 9.5%, 6.5 to 9.0%, 7 to 8.5%, including 7.5 to 8.0%.

In some instances, the D2SP drives expression of a gene product operably linked thereto with a high penetrance. Penetrance of a promoter can be expressed as the number of cells expressing a gene product operably linked to the promoter and staining positively with an antibody specific to the D2 receptor (such as Millipore ab1558; FIG. 3), divided by the total number of cells staining positively with an antibody specific to the D2 receptor (such as Millipore ab1558; FIG. 3). In some instances, the D2SP drives expression of a gene product operably linked thereto with a penetrance of 70% or more, e.g., 72% or more, 74% or more, 76% or more, 78% or more, 79% or more, 80% or more, 81% or more, 82% or more, 83% or more, 84% or more, 85% or more, 86% or more, 86.5% or more, 86.8% or more, or 87% or more. In some instances, the D2SP drives expression of a gene product operably linked thereto with a penetrance of 99% or less, e.g., 95% or less, 94% or less, 93% or less, 92% or less, 91% or less, 90% or less, 89.5% or less, 89% or less, 89.5% or less, 89% or less, 88.5% or less, 88% or less, 87.5% or less, or 87% or less. In some instances, the D2SP drives expression of a gene product operably linked thereto with a penetrance in the range of 70 to 95%, e.g., 75 to 95%, including 78 to 93%, 79 to 91%, 80 to 90%, 81 to 89%, or 82 to 87%. In some instances, the D2SP drives expression of a gene product operably linked thereto with a penetrance of about 86.8%.

In some instances, the D2SP drives expression of a gene product operably linked thereto with a percentage penetrance that is higher than the percentage penetrance of expression of the gene product driven by a conventional D2 receptor promoter, e.g. a D2 receptor promoter that includes exon 1 of the D2 receptor gene, such as a nucleic acid having a sequence at least 90%, e.g., at least 95%, at least 98%, at least 99% or 100% identical to the sequence shown in SEQ ID NO: 2, by 5% or more, e.g., 8% or more, 10% or more, 12% or more, 14% or more, 16% or more, 17% or more, including 18% or more. In some instances, the D2SP drives expression of a gene product operably linked thereto with a percentage penetrance that is higher than the percentage penetrance of expression of the gene product driven by a conventional D2 receptor promoter, e.g. a D2 receptor promoter that includes exon 1 of the D2 receptor gene, such as a nucleic acid having a sequence at least 90%, e.g., at least 95%, at least 98%, at least 99% or 100% identical to the sequence shown in SEQ ID NO: 2, by 35% or less, e.g., 30% or less, 25% or less, 24% or less, 23% or less, 22% or less, 21% or less, 20% or less, 19% or less, including 18% or less. In some instances, the D2SP drives expression of a gene product operably linked thereto with a percentage penetrance that is higher than the percentage penetrance of expression of the gene product driven by a conventional D2 receptor promoter, e.g. a D2 receptor promoter that includes exon 1 of the D2 receptor gene, such as a nucleic acid having a sequence at least 90%, e.g., at least 95%, at least 98%, at least 99% or 100% identical to the sequence shown in SEQ ID NO: 2, in the range of 5 to 35%, e.g., 8 to 30%, 10 to 25%, 12 to 20%, 14 to 19%, including 16 to 18%.

In certain instances, the gene product operably linked to a D2SP in a nucleic acid introduced into a target cell is a light-responsive polypeptide, as described above and elsewhere herein. When the gene product is a light-responsive polypeptide operably linked to a D2SP, the light-responsive polypeptide expressed in the target cell, such as a target neuron, can modulate the activity of the target cell by inducing hyperpolarization or depolarization of the target cell when the polypeptide is activated by light. In some instances, the activity modulated by activation of the light-responsive polypeptide is the pattern or amplitude of action potential firing, the resting potential, subthreshold changes in membrane potential, activity-dependent transcription and/or translation of a gene, and the like, in a target neuron.

In some embodiments, a light-activated polypeptide, when expressed on the membrane of a cell (e.g., a mammalian cell), and when exposed to light of an activating wavelength, hyperpolarizes the membrane. In some embodiments, a light-activated polypeptide exhibits prolonged stability of photocurrents. In some embodiments, a light-activated polypeptide exhibits enhanced expression in cell membranes and larger photocurrents in cultured neurons. In some embodiments, a subject light-activated polypeptide exhibits decelerated channel kinetics/decelerated channel closure. In some embodiments, a light-activated polypeptide conduct anions and inhibits the formation of action potentials in neurons for an extended period of time (e.g., from about 0.5 hours, up to about 0.75 hours, up to about 1 hour, up to about 1.25 hours, up to about 1.5 hours, up to about 1.75 hours, up to about 2 hours, up to about 2.25 hours, up to about 2.5 hours, up to about 2.75 hours, up to about 3 hours or more) after brief light stimulations at lower light intensities.

In some instances, the gene product operably linked to a D2SP in a nucleic acid introduced into a target cell is a fluorescent protein polypeptide, as described above and elsewhere herein. When the gene product is a fluorescent protein operably linked to a D2SP, the fluorescent protein expressed in the target cell, such as a target neuron, can fluorescently label the target cell by emitting light when the protein is stimulated by light of an appropriate wavelength, as described above. In certain embodiments, the fluorescent protein is a genetically encoded indicator, such as a calcium indicator or a voltage indicator. When the gene product is a genetically encoded indicator operably linked to a D2SP, the genetically encoded indicator expressed in the target cell, such as a target neuron, alters its fluorescence properties, such as intensity, excitation and/or emission wavelengths, etc.

Any convenient means may be used to deliver light to the target cell or neuron expressing a gene product operably linked to a D2SP, thereby modulating or fluorescently labeling the target cell. A target cell in culture or in an ex vivo tissue slice may be subjected to light using a fluorescent microscope, a target cell in suspension may be subjected to light using fluorescence activated cell sorting (FACS) device or a fluorimeter, and so on.

In some cases, the light is delivered transdermally or transcutaneously to a target cell or neuron in vivo. In some cases, an implantable light source is used; and the light is delivered to a site within the body. In some cases, the light is delivered to a treatment site within the body. In some cases, the light is delivered intracranially.

In some cases, the light used to activate a light-responsive polypeptide expressed in a neuron has an intensity of from about 0.05 mW/mm$^2$ to about 0.1 mW/mm$^2$, from about 0.1 mW/mm$^2$ to about 0.2 mW/mm$^2$, from about 0.2 mW/mm$^2$ to about 0.3 mW/mm$^2$, from about 0.3 mW/mm$^2$ to about 0.4 mW/mm$^2$, from about 0.4 mW/mm$^2$ to about 0.5 mW/mm$^2$, from about 0.5 mW/mm$^2$ to about 0.6 mW/mm$^2$, from about 0.6 mW/mm$^2$ to about 0.7 mW/mm$^2$, from about about 0.7 mW/mm$^2$ to about 0.8 mW/mm$^2$, from about 0.8 mW/mm$^2$ to about 0.9 mW/mm$^2$, or from about about 0.9 mW/mm$^2$ to about 1.0 mW/mm$^2$. In some cases, the light used to activate a light-responsive polypeptide expressed in a neuron has an intensity of from about 1.0 mW/mm$^2$ to about 1.1 mW/mm$^2$, from about 1.1 mW/mm$^2$ to about 1.2 mW/mm$^2$, from about 1.2 mW/mm$^2$ to about 1.3 mW/mm$^2$, from 1.3 mW/mm$^2$ to about 1.4 mW/mm$^2$, from about 1.4 mW/mm$^2$ to about 1.5 mW/mm$^2$, from about 1.5 mW/mm$^2$ to about 1.6 mW/mm$^2$, from about 1.6 mW/mm$^2$ to about 1.7 mW/mm$^2$, from about 1.7 mW/mm$^2$ to about 1.8 mW/mm$^2$, from about 1.8 mW/mm$^2$ to about 1.9 mW/mm$^2$, from about 1.9 mW/mm$^2$ to about 2.0 mW/mm$^2$, from about 2.0 mW/mm$^2$ to about 2.5 mW/mm$^2$, from about 2.5 mW/mm$^2$ to about 3 mW/mm$^2$, from about 3 mW/mm$^2$ to about 3.5 mW/mm$^2$, from about 3.5 mW/mm$^2$ to about 4 mW/mm$^2$, from about 4 mW/mm$^2$ to about 4.5 mW/mm$^2$, from about 4.5 mW/mm$^2$ to about 5 mW/mm$^2$, from about 5 mW/mm$^2$ to about 5.5 mW/mm$^2$, from about 5.5 mW/mm$^2$ to about 6 mW/mm$^2$, from about 6 mW/mm$^2$ to about 7 mW/mm$^2$, or from about 7 mW/mm$^2$ to about 10 mW/mm$^2$. In some cases, the light used to activate a light-responsive polypeptide expressed in a neuron has an intensity of from about 0.05 mW/mm$^2$ to about 0.1 mW/mm$^2$. In some cases, the light used to activate a light-responsive polypeptide expressed in a neuron has an intensity of about 0.25 mW/mm$^2$. In some cases, the light used to activate a light-responsive polypeptide expressed in a neuron has an intensity of about 1 mW/mm$^2$.

Utility

The subject nucleic acids, genetically modified host cells and methods find use in a wider variety of applications, including transfecting, identifying, targeting, and isolating live D2R-expressing cells derived from healthy or afflicted human and animal subject populations, as well as transfection, identification, and isolation of D2R-expressing cells from stem/progenitor-cell populations from healthy or afflicted subjects, for in-vitro/ex-vivo genetic, proteomic, transcriptomic, electrophysiological, and pharmacologic analyses.

A nucleic acid comprising a D2SP may find use in enrichment of D2R-expressing cells through cell-sorting techniques such as fluorescent-activated cell sorting (FACS), not only for analysis and characterization of the cell population associated with dozens of dopamine-related disorders, but also for the purpose of therapeutic transplantation of the D2R-expressing cells.

In some embodiments, factors that participate in induction of cells to differentiate into dopaminoceptive neurons may be identified using a D2SP to study D2R-expressing cultured cells and D2R-expressing human-derived stem cells as well as nonhuman-derived stem cells. In certain embodiments, graft cells for drug addiction, obesity, gambling disorder and others may be obtained from undifferentiated cells using a D2SP to identify the relevant cell populations for grafting. In other cases, novel drugs for treatment may be developed based on the dopaminoceptive neurons' differentiating and inducing factors identified using cells identified based on D2SP-driven expression of a fluorescent protein. The subject nucleic acid and method of using the same enable targeting of virally-mediated optogenetic constructs, RNA or DNA-based therapies, and other gene-therapy approaches in patient populations, both in isolation and in combination with pharmacologic, direct-stimulation, or antibody-based interventions.

In some embodiments, the subject nucleic acid and method may be used to target expression of gene products for the study and treatment of both central and peripheral disorders, which include but are not limited to: schizophrenia, gambling disorder, drug addiction, Tourette's syndrome, multiple system atrophy, supranuclear palsy, parkinson's disease, dementia, autism, ADHD, depression, tardive dyskinesia, glioblastoma, compulsive/impulsive sexual behavior, compulsive spending, obesity, functional dyspepsia, gastric stasis, emesis, diabetic gastroparesis, irritable bowel syndrome, Cushing's disease, hypertension, and renal inflammation/injury, and hyperprolactinaemia with associated alterations, such as gynaecomastia, galactorrhoea, amenorrhoea and impotence. D2R-expressing cells may also be characterized to provide animal models of these diseases, on which more detailed characterization and drug/therapeutic screening can be performed.

Kits

Further aspects of the present disclosure include a kit that includes a recombinant expression vector, as described above, comprising the subject nucleic acid, i.e., a nucleic acid comprising a dopamine receptor type 2-specific promoter (D2SP), wherein the D2SP does not include exon 1 of a D2 receptor gene, wherein the D2SP includes a Kozak sequence, and wherein the D2SP comprises a nucleotide sequence having at least 95% sequence identity to the nucleotide sequence set forth in SEQ ID NO: 1. In certain embodiments, the recombinant expression vector of the subject kit comprises multiple cloning sites, or equivalents thereof, that facilitate subcloning a nucleotide sequence encoding a gene product of interest to a user into the recombinant expression vector, thereby operably linking the nucleotide sequence encoding the gene product of interest to the D2SP.

In certain embodiments, the recombinant expression vector of the subject kit comprises a nucleotide sequence encoding a light-responsive polypeptide, a genetically encoded indicator and/or a fluorescent protein operably linked to the D2SP.

The kit may also include a control expression vector, such as a positive control expression vector and/or a negative control expression vector. In some embodiments, the positive control expression vector comprises a nucleic acid encoding a known gene product, such as a light-responsive polypeptide or a fluorescent polypeptide as described above, operably linked to the D2SP. In some instances, the positive control expression vector contains a nucleic acid encoding a fluorescent protein, such as a green fluorescent protein, a yellow fluorescent protein, or a red fluorescent protein.

Components of a subject kit can be in separate containers; or can be combined in a single container.

In addition to above-mentioned components, a subject kit can further include instructions for using the components of the kit and to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Protocol for Antibody Staining Cells Expressing a Type 2 Dopamine Receptor The following protocols were used to stain cells in a fixed tissue section with a type 2 dopamine (D2) receptor-specific antibody.

A. Standard Staining Protocol:

1) Rinsed 40 μm sections in phosphate-buffered saline (PBS) (pH 7.4) 3×10 minutes.

2) Blocked in PBS+3% normal donkey serum+0.3% Triton-X for 30 minutes (PBS++)

3) Incubated in primary antibody (rabbit anti-D2R, millipore ab1558) 1:500 in PBS++ overnight at 4° C. on a rotary shaker.

4) Washed slices 4×15 minutes in PBS

5) Incubated in secondary antibody (Alexa-fluor 647, goat anti-rabbit, Life Technologies A-21245) 1:500 in PBS++ for 3 hours at room temperature.

6) Washed for 15 min in PBS

7) Washed for 15 min in 1:50000 4',6-diamidino-2-phenylindole (DAPI) in PBS

8) Washed for 15 min in PBS

The above protocol produced the staining pattern seen in FIG. 3A.

B. Modified Staining Protocol:
1) Rinsed 40 μm sections in PBS (pH 7.4) 3×10 minutes.
2) Blocked in PBS+3% normal donkey serum+0.3% Triton-X for 30 minutes (PBS++)
3) Incubated in primary antibody (rabbit anti-D2R, millipore ab1558) 1:200 in PBS++24 hrs at room temperature on a rotary shaker.
4) Washed slices 4×15 minutes in PBS
5) Incubated in secondary antibody (Alexa-fluor 647, goat anti-rabbit, Life Technologies A-21245) 1:500 in PBS++ for 8 hours at room temperature.
6) Washed slices 4×15 minutes in PBS
7) Incubated in tertiary antibody (Alexa-fluor 647, donkey anti-goat, Life Technologies A-21447) 1:500 in PBS++ for 8 hours at room temperature.
8) Washed for 15 min in PBS
9) Washed for 15 min in 1:50000 DAPI in PBS
10) Washed for 15 min in PBS The above protocol produced the staining pattern seen in FIG. 3B.

Example 2: D2SP Drives Expression in Rat Hippocampal Primary Neurons

Figure 4:
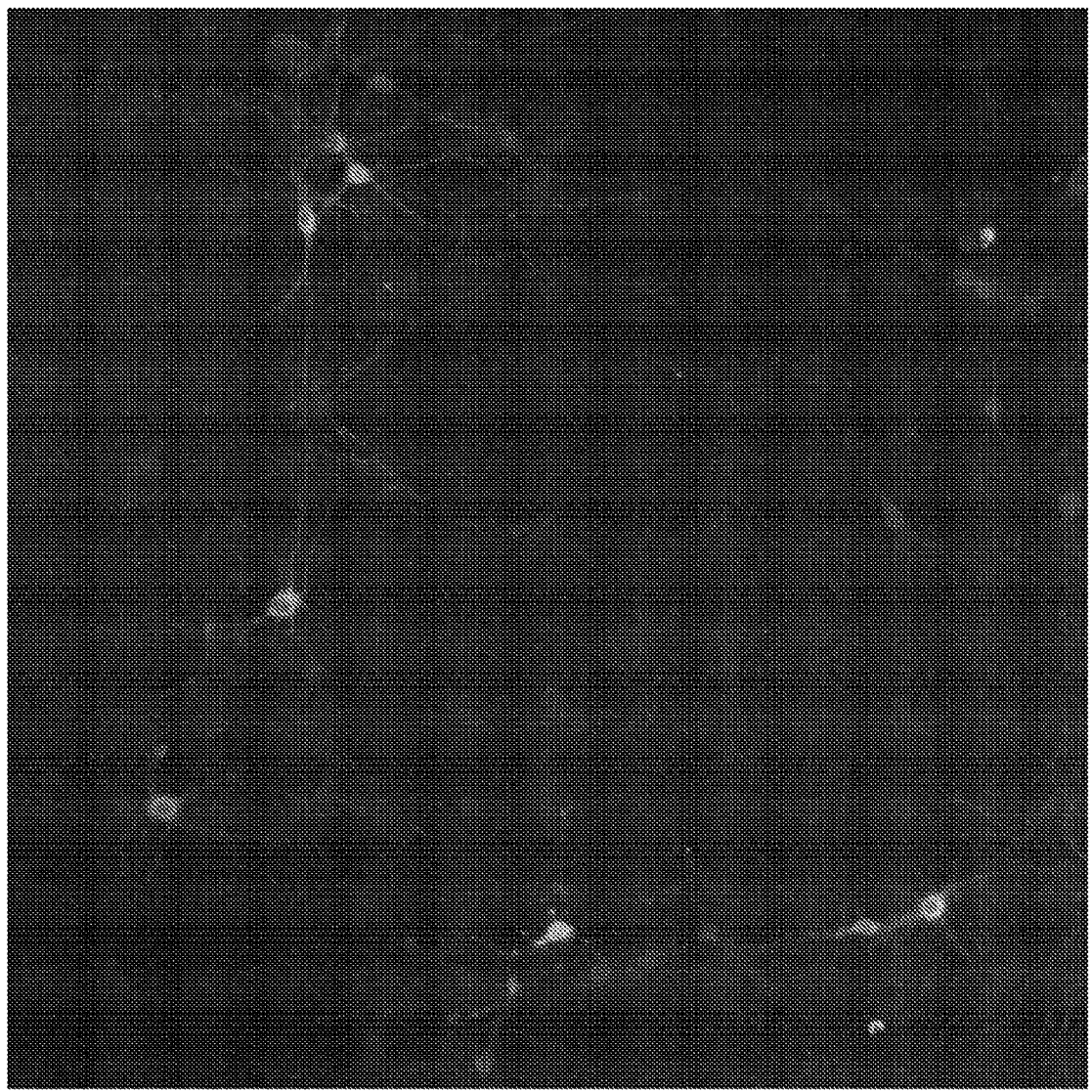
FIG. 4 shows rat hippocampal primary neurons expressing eNpHR 3.0-EYFP under the D2SP and antibody stained for D2 receptors using the modified staining protocol, according to an embodiment of the present disclosure.

Rat Hippocampal primary neurons were transfected with D2SP-eNpHR 3.0-EYFP and stained for D2R using the modified staining procedure described in Example 1 (FIG. 4). The green color is from the EYFP, showing the cells expressing D2SP-eNpHR 3.0-EYFP and blue shows all Dopamine Receptor 2 cells.

Example 3: Comparison of Expression of eNpHR 3.0-EYFP Under D2SP and D2R

With reference to FIG. 5, the middle panels show EYFP, showing the cells expressing D2SP-eNpHR 3.0-EYFP (top) or D2R-eNpHR 3.0-EYFP (bottom) and the left panels show all Dopamine Receptor 2 cells. The right panels for each promoter construct show the merge of the two previous panels.

The specificity and penetrance of the two promoters were also compared and are shown in Table 1.

TABLE 1

|  | Specificity | Penetrance |
| --- | --- | --- |
| D2SP::NY | 112/114 = 98.2% | 112/129 = 86.8% |
| D2R::NY | 76/84 = 90.5% | 76/110 = 69% |

Example 4: Recombinant Expression Vectors Containing D2SP

Figure 6:
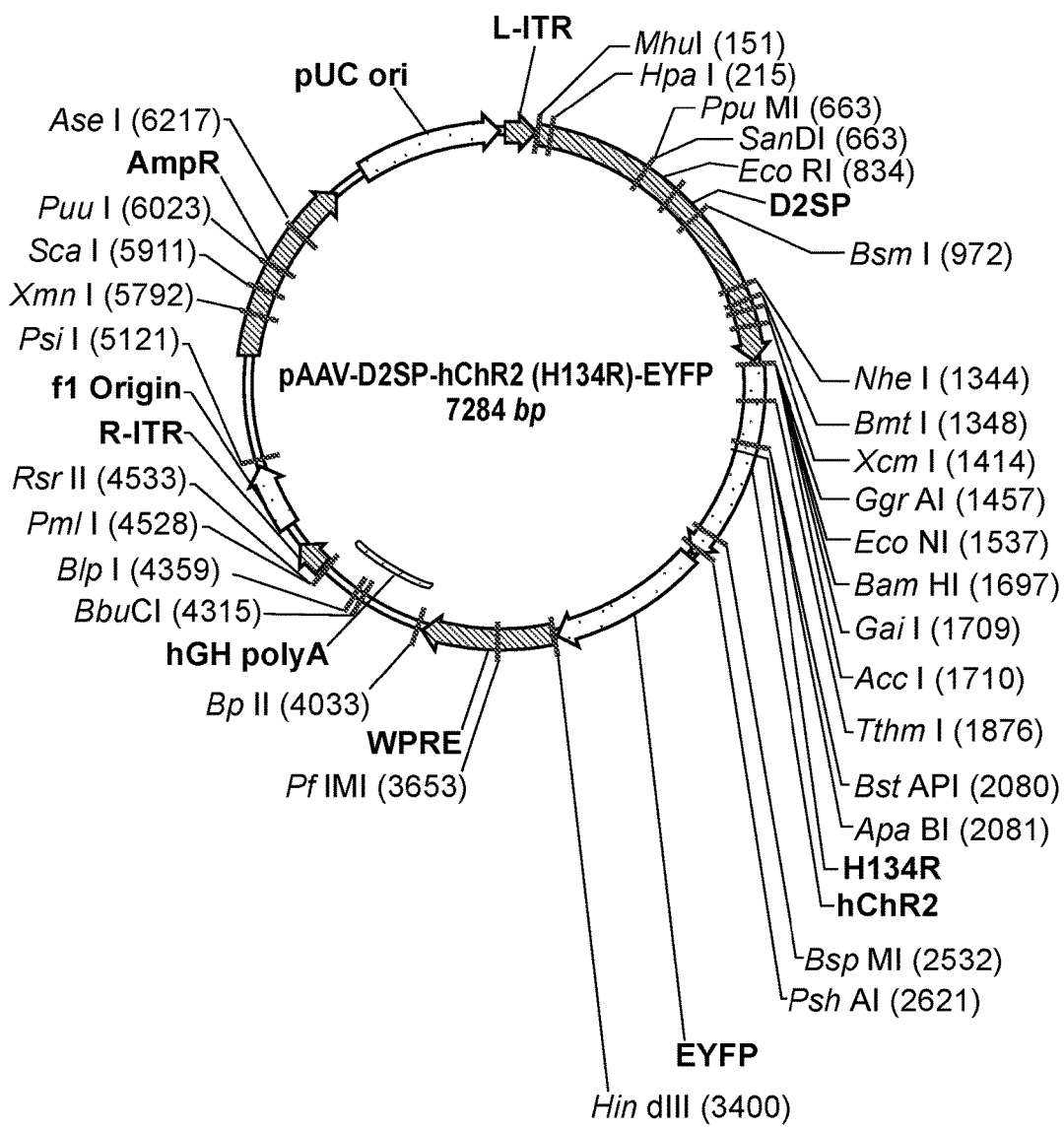
FIGS. 6-14 show schematic maps of recombinant expression vectors containing a D2SP, according to an embodiment of the present disclosure.
Figure 7:
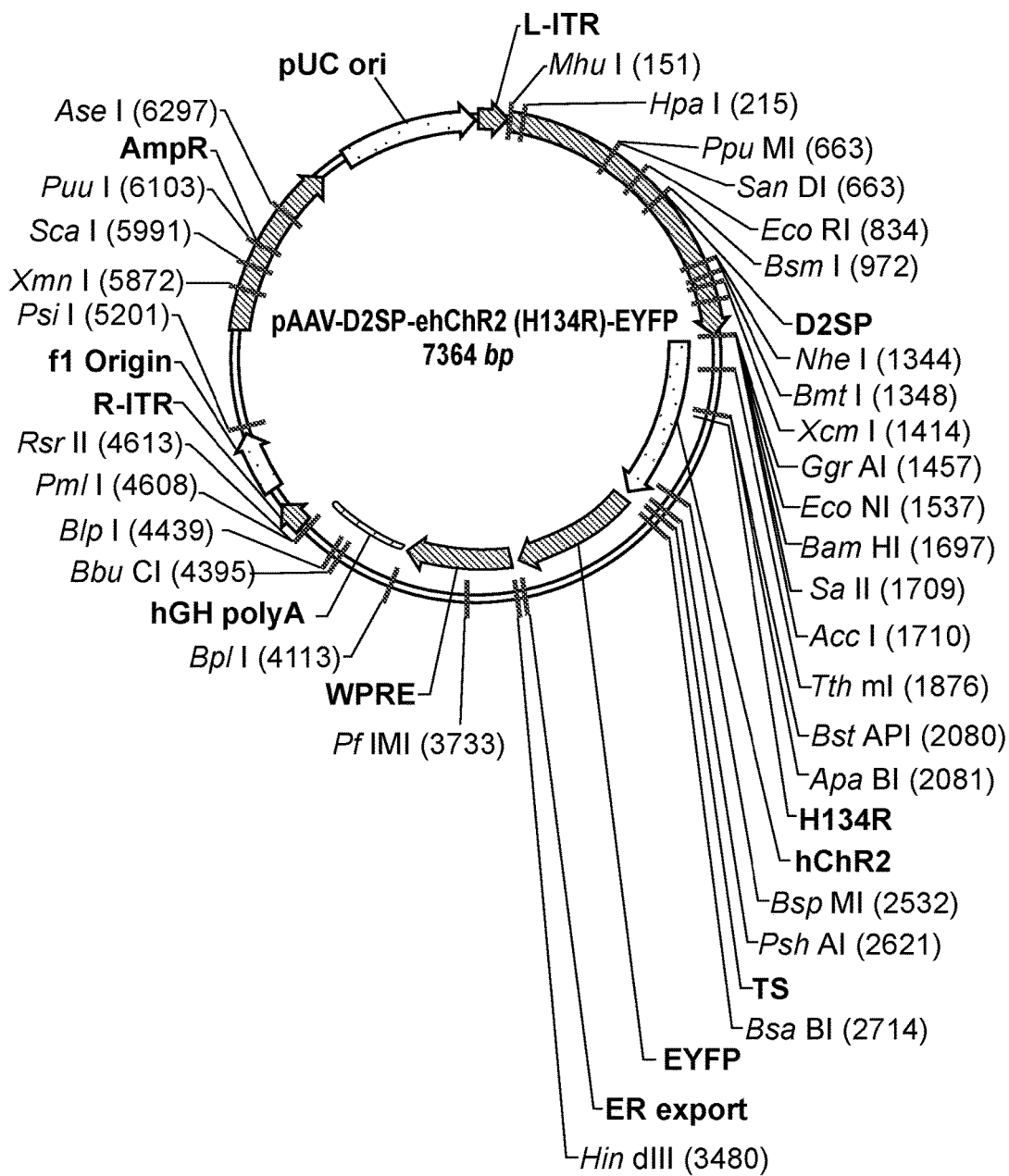
Figure 8:
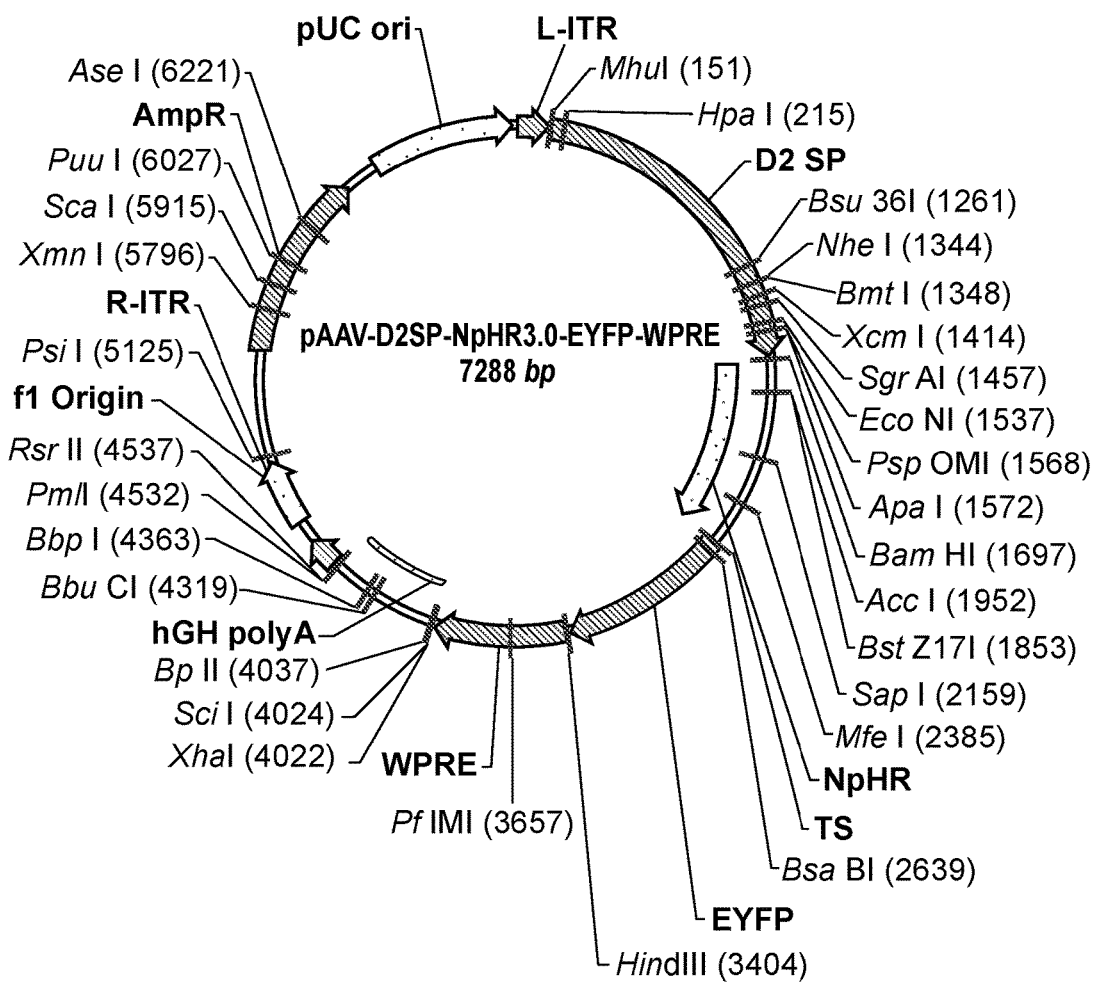
Figure 9:
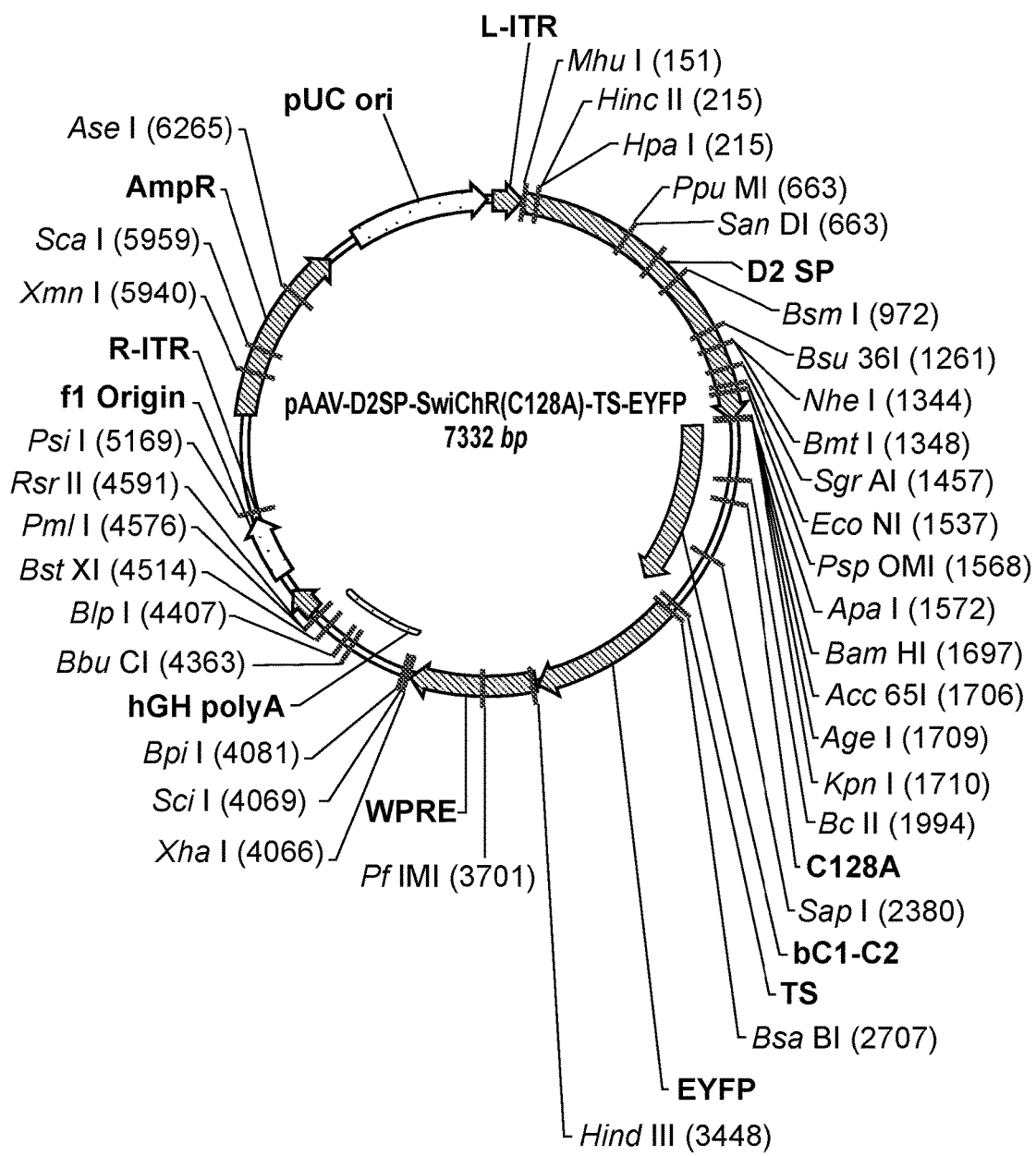
Figure 10:
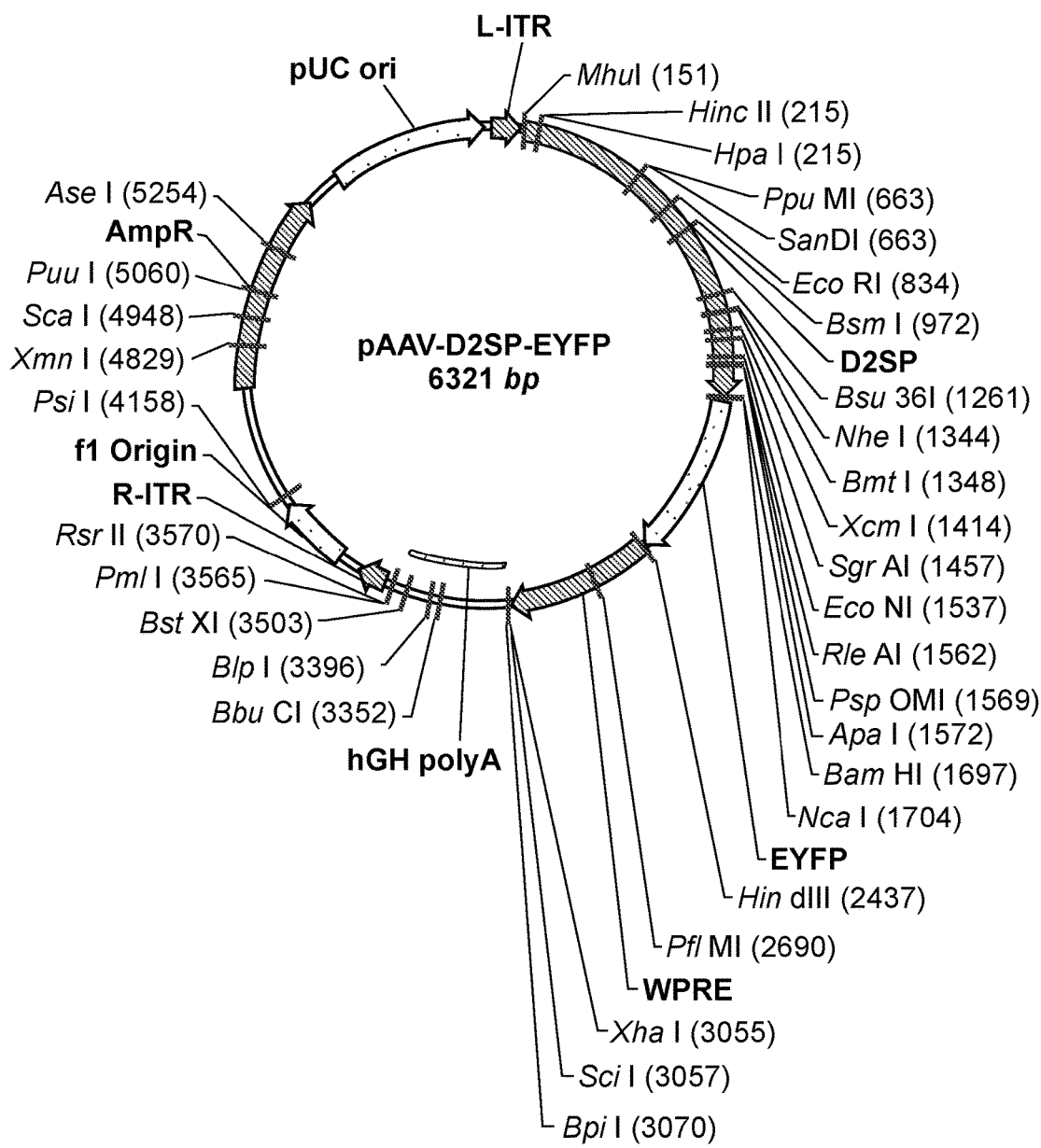
Figure 11:
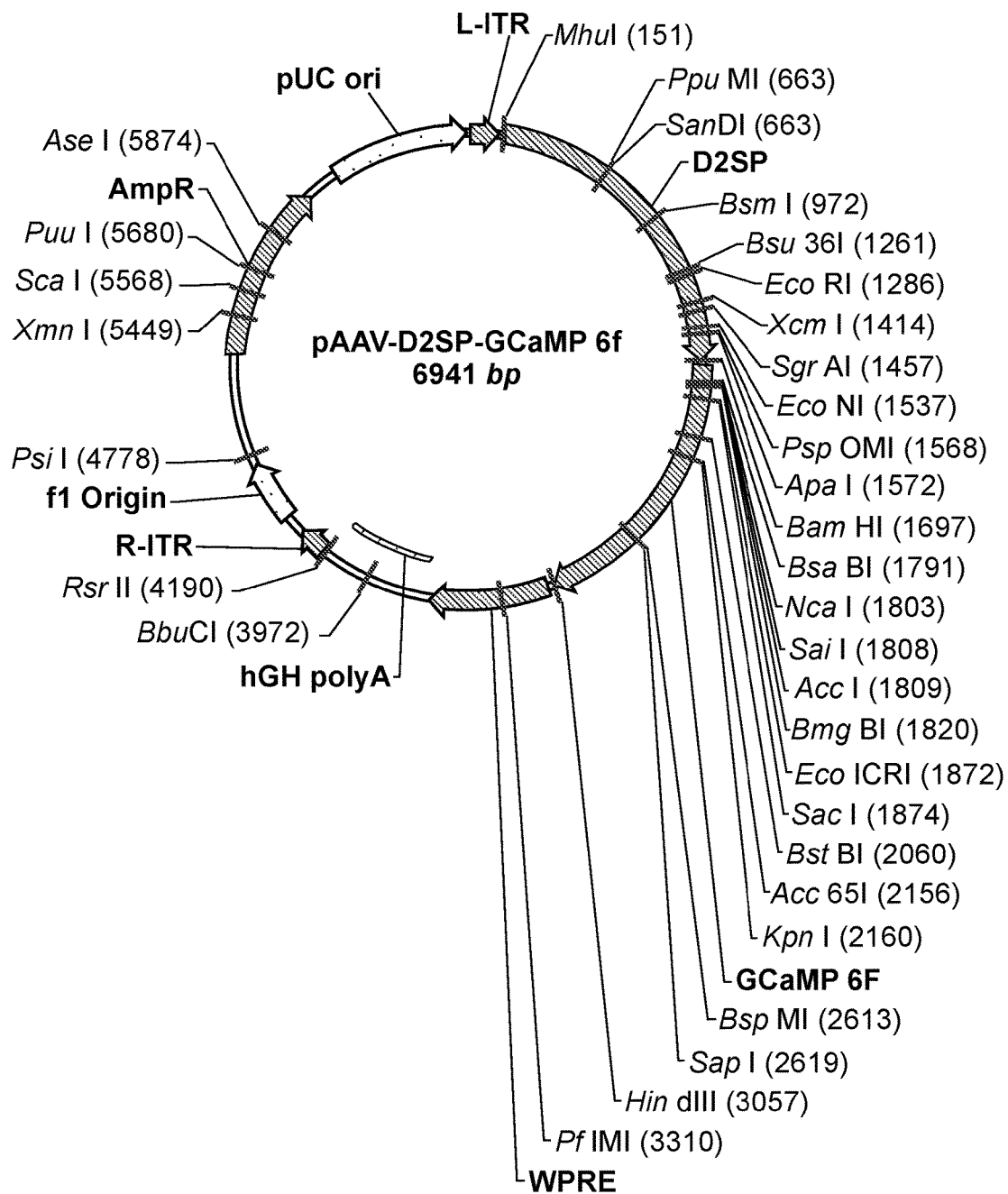
Figure 12:
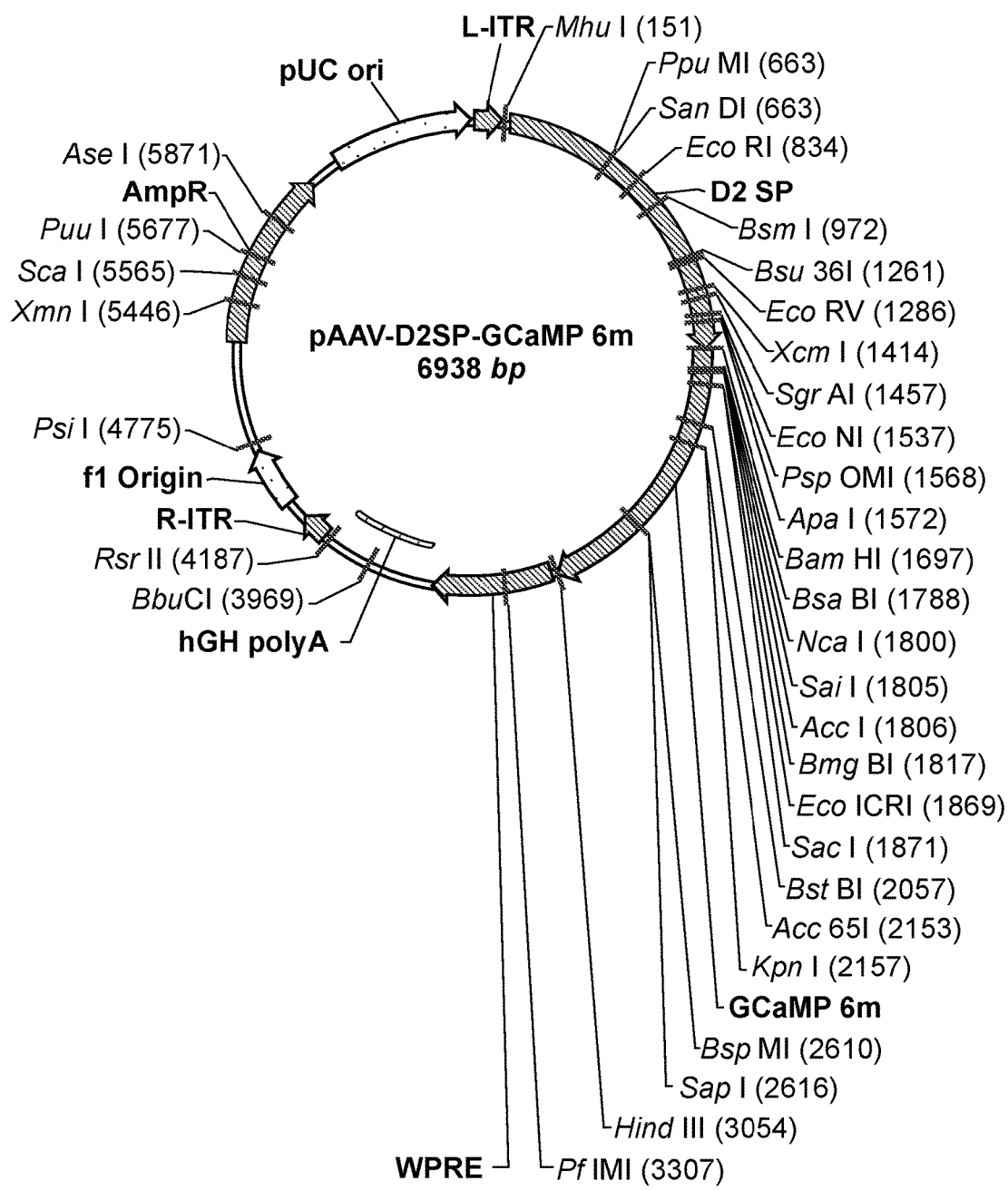
Figure 13:
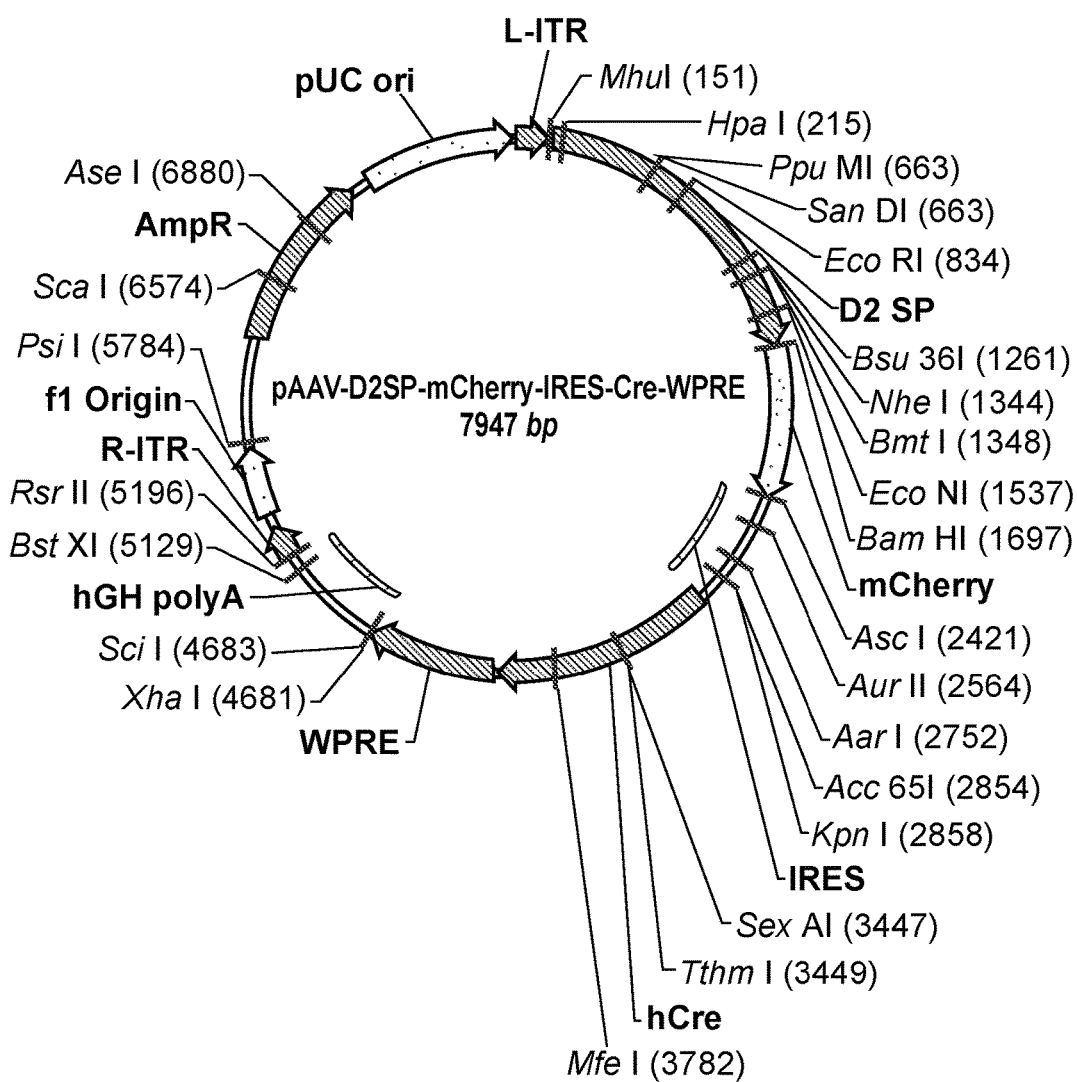
Figure 14:
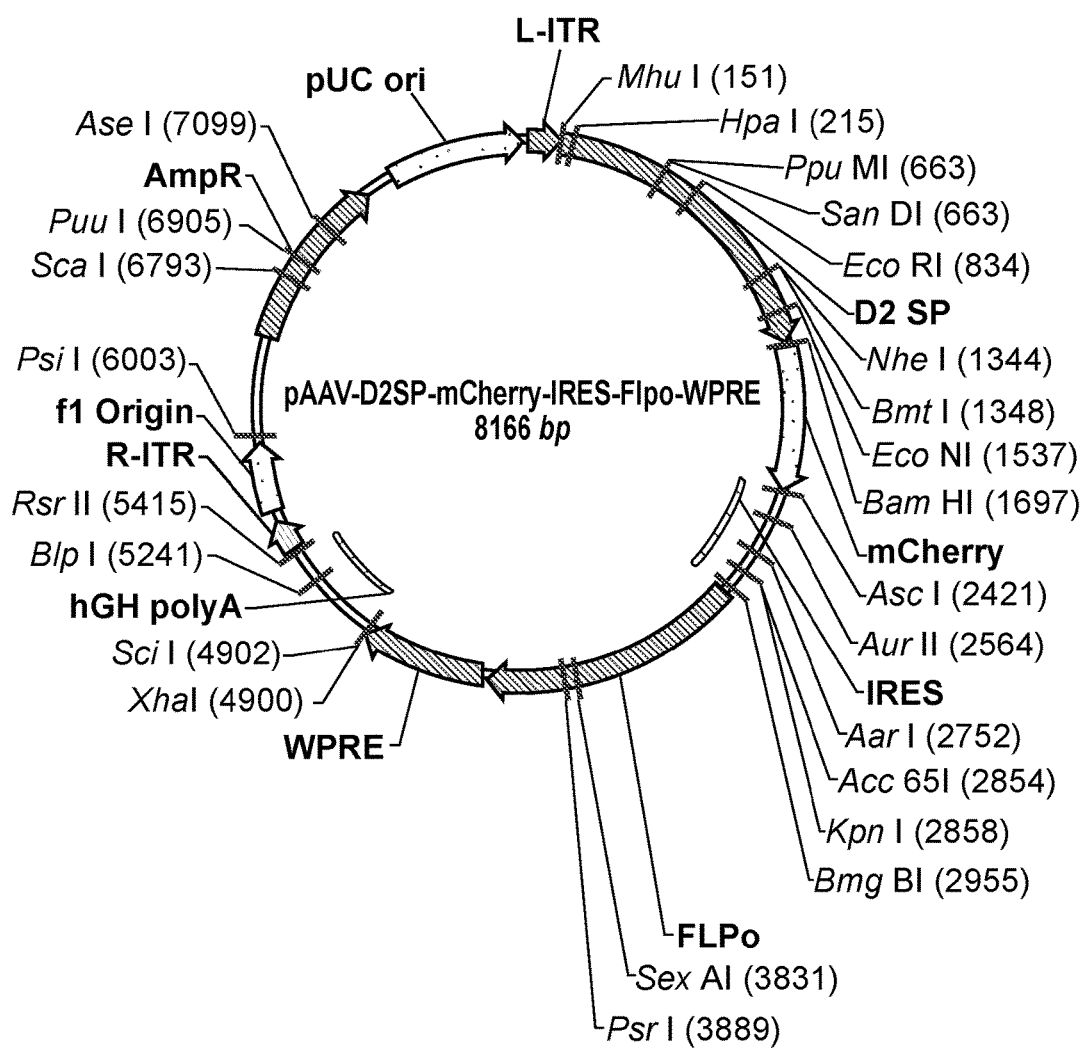

The following recombinant expression vectors that contain D2SP operably linked to nucleotides sequences encoding one or more gene products were constructed:
pAAV-D2SP-hChR2(H134R)-EYFP (FIG. 6);
pAAV-D2SP-ehChR2(H134R)-EYFP (FIG. 7);
pAAV-D2SP-eNpHR 3.0-EYFP (FIG. 8);
pAAV-D2SP-SwiChRca-TS-EYFP (FIG. 9);
pAAV-D2SP-EYFP (FIG. 10);
pAAV-D2SP-GCaMP 6f (FIG. 11);
pAAV-D2SP-GCaMP 6m (FIG. 12);
pAAV-D2SP-mCherry-IRES-Cre (FIG. 13); and
pAAV-D2SP-mCherry-IRES-Flpo (FIG. 14).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A nucleic acid comprising a dopamine receptor type 2-specific promoter (D2SP), wherein the D2SP does not include exon 1 of a D2 receptor gene, wherein the D2SP contains a Kozak sequence, and wherein the D2SP contains a nucleotide sequence having at least 95% sequence identity to the nucleotide sequence set forth in SEQ ID NO: 1.

2. The nucleic acid of claim 1, wherein the Kozak sequence is at the 3' terminus of the D2SP.

3. The nucleic acid of claim 1, wherein the D2SP contains a BamHI restriction site.

4. The nucleic acid of claim 3, wherein the BamHI restriction site is located 5' of the Kozak sequence.

5. The nucleic acid of claim 1, wherein the D2SP contains a nucleotide sequence having at least 98% sequence identity to the nucleotide sequence set forth in SEQ ID NO: 1.

6. The nucleic acid of claim 1, wherein the D2SP is operably linked to a nucleotide sequence encoding a gene product that provides a detectable signal.

7. The nucleic acid of claim 6, wherein the gene product that provides a detectable signal is a fluorescent protein.

8. The nucleic acid of claim 7, wherein the fluorescent protein is selected from the group consisting of a green fluorescent protein, a yellow fluorescent protein, a cyan fluorescent protein, a calcium indicator and a voltage indicator.

9. The nucleic acid of claim 1, wherein the D2SP is operably linked to a nucleotide sequence encoding a light-responsive polypeptide.

10. The nucleic acid of claim 9, wherein the light-responsive polypeptide is a depolarizing light-responsive polypeptide, wherein the depolarizing light-responsive polypeptide contains an amino acid sequence having at least 75% sequence identity to any one of SEQ ID NOs: 4-23.

11. The nucleic acid of claim 9, wherein the light-responsive polypeptide is a hyperpolarizing light-responsive polypeptide, wherein the hyperpolarizing light-responsive polypeptide contains an amino acid sequence having at least 75% sequence identity to any one of SEQ ID NOs: 24-54.

12. The nucleic acid of claim 1, wherein the D2SP is operably linked to a nucleotide sequence encoding a recombinase.

13. The nucleic acid of claim 12, wherein the recombinase is selected from the group consisting of a Cre recombinase and a FLP recombinase.

14. A recombinant expression vector comprising the nucleic acid of claim 1.

15. A genetically modified isolated host cell comprising the nucleic acid of claim 1, or the recombinant expression vector of claim 14.

16. The genetically modified host cell of claim 15, wherein the host cell is a neuronal cell.

17. The genetically modified host cell of claim 15, wherein the host cell is a progenitor cell.

18. The genetically modified host cell of claim 17, wherein the progenitor cell is a stem cell.

19. A method of modulating activity of a target neuron, the method comprising introducing into the target neuron the nucleic acid of claim 1, wherein the D2SP is operably linked to a light-responsive polypeptide that, when activated by light, induces hyperpolarization or depolarization of the target neuron.

20. A method of fluorescently labeling a target cell, the method comprising introducing into the target cell the nucleic acid of claim 1, wherein the D2SP is operably linked to a fluorescent protein that, when expressed, fluorescently labels the target cell.

21. The method of claim 20, wherein the target cell is a neuronal cell.

22. The method of claim 20, wherein the target cell is a progenitor cell.

23. The method of claim 22, wherein the progenitor cell is a stem cell.

24. A kit comprising:
a recombinant expression vector that comprises a nucleic acid comprising a dopamine receptor type 2-specific promoter (D2SP), wherein the D2SP does not include exon 1 of a D2 receptor gene, wherein the D2SP contains a Kozak sequence, and wherein the D2SP comprises a nucleotide sequence having at least 95% sequence identity to the nucleotide sequence set forth in SEQ ID NO: 1; and
instructions for introducing the recombinant expression vector into a target cell.

25. The kit of claim 24, wherein the kit further comprises a control expression vector that contains a nucleic acid containing a dopamine receptor type 2-specific promoter (D2SP), wherein the D2SP does not include exon 1 of a D2 receptor gene, wherein the D2SP comprises a Kozak sequence, and wherein the D2SP comprises a nucleotide sequence having at least 95% sequence identity to the nucleotide sequence set forth in SEQ ID NO: 1.

26. The nucleic acid of claim 1, wherein the length of the nucleotide sequence is 1500 base pairs or more.

* * * * *

SEQUENCE LISTING

```
<160> NUMBER OF SEQ ID NOS: 66

<210> SEQ ID NO 1
<211> LENGTH: 1552
<212> TYPE: DNA
<213> ORGANISM: Artificial sequence
<220> FEATURE:
<223> OTHER INFORMATION: Synthetic nucleic acid

<400> SEQUENCE: 1
ttatcctcgg tgcatctcag agaaataagc attgcttgga ccaatgtgga ccggatgtta      60
acacctagag ccagagagat taaaaaattt aatcaacatc tacaactggc aagggataga     120
cataggacac acgactgggt ggaaaacgta tagaggtgat gggttgagaa gaacaaaatc     180
cctgtttaag taggttattt cttgggaaga acatgtccag ggcacatagg aaaatagtgg     240
ggattcaacc atgtctgtaa tgtgtgagtg ccttaaaagc aaatgtgaaa aattctaatg     300
tttctggtag ttctaacact tccctaccat gcctatagag agccatgaat agaccatacc     360
ccaagaataa tgaatagggg aaggggaggc tagttcccct tttcttaaat gcctccataa     420
ctggccacat ctaagaaaaa tgtgctgtgt atagggactg ttccactgct ggttccccgt     480
gaggtttgga ggggcatgcc tctttgggtc ccagattcca cctttgaaat caaacagggg     540
```

-continued

```
ttagttgaat attagtgtct gtctttccaa ccttaatttt ccaggattgt gtggatcaat      600
ggaaggagtt tcttctttgt ggctaagtgg catgactgcc ggctatatgc agactgtcct      660
ctgtgctcct gcccttggaa ttctgtggtg ccttctcctt ggggacttga attggccaat      720
ggccagctcc tgtgaggtct ccggagctgt cggtactcca cagcacctat ttaagctaca      780
agtatttgga agactctact ctggattgac cccatgcatt ctgaatctca tgtagaagct      840
ggccaaggca ggacagaggg acagaaagca ccagctggat ttgagaagaa gaggatggaa      900
agggttgtag gttccctggg tgggagatga ccctggacag ggctgaagaa gatcacattt      960
ctcttcctcc tgctcctcag tgcagacgga agggtgagct agaattttca cggccttctt     1020
tatcattccc atcttagatc tgctctgccc aagtcttcct ctcagaaagc acaacagcag     1080
aacgaactgc tgtgattttc agacctgagg tctgtacacc gactctggat atccttccgg     1140
aatctatttc tcctttaaag acttgatgta ccacacgtag tgcttcagct agcccttggc     1200
cctgactcct caaaggaggg gatcgacccg ctggtgttgt gattgctaga ccagagtagg     1260
tttggatggg cagggtgtta cttaaaaagt ataggatgac accggcgagc agtccggagc     1320
acaggctatc cccactcaaa gccagagatg gattctcggt ctcagctctc aaggttcctt     1380
ccccaggccc cacagtgcag agatagttct ggggccctgg gtgggtgggg cctctgtaca     1440
aggggcgggg ttcccgggcg cctcgtggcc agggtgaccc cgcccctcc tcctgcgcag      1500 cgctctgatt ccgcggagct gtccagcctc agtgccgggg ggatccgcca cc             1552
```

<210> SEQ ID NO 2
<211> LENGTH: 1810
<212> TYPE: DNA
<213> ORGANISM: Artificial sequence
<220> FEATURE:
<223> OTHER INFORMATION: Synthetic nucleic acid

<400> SEQUENCE: 2

```
ttatcctcgg tgcatctcag agaaataagc attgcttgga ccaatgtgga ccggatgtta       60
acacctagag ccagagagat taaaaatttt aatcaacatc tacaactggc aagggataga      120
cataggacac acgactgggt ggaaaacgta tagaggtgat gggttgagaa gaacaaaatc      180
cctgtttaag taggttattt cttgggaaga acatgtccag ggcacatagg aaaatagtgg      240
ggattcaacc atgtctgtaa tgtgtgagtg ccttaaaagc aaatgtgaaa aattctaatg      300
tttctggtag ttctaacact tccctaccat gcctatagag agccatgaat agaccatacc      360
ccaagaataa tgaatagggg aaggggaggc tagttcccct tttcttaaat gcctccataa      420
ctggccacat ctaagaaaaa tgtgctgtgt atagggactg ttccactgct ggttccccgt      480
gaggtttgga ggggcatgcc tctttgggtc ccagattcca cctttgaaat caaacagggg      540
ttagttgaat attagtgtct gtctttccaa ccttaatttt ccaggattgt gtggatcaat      600
ggaaggagtt tcttctttgt ggctaagtgg catgactgcc ggctatatgc agactgtcct      660
ctgtgctcct gcccttggaa ttctgtggtg ccttctcctt ggggacttga attggccaat      720
ggccagctcc tgtgaggtct ccggagctgt cggtactcca cagcacctat ttaagctaca      780
agtatttgga agactctact ctggattgac cccatgcatt ctgaatctca tgtagaagct      840
ggccaaggca ggacagaggg acagaaagca ccagctggat ttgagaagaa gaggatggaa      900
agggttgtag gttccctggg tgggagatga ccctggacag ggctgaagaa gatcacattt      960
ctcttcctcc tgctcctcag tgcagacgga agggtgagct agaattttca cggccttctt     1020
tatcattccc atcttagatc tgctctgccc aagtcttcct ctcagaaagc acaacagcag     1080
```

```
aacgaactgc tgtgattttc agacctgagg tctgtacacc gactctggat atccttccgg    1140
aatctatttc tcctttaaag acttgatgta ccacacgtag tgcttcagct agcccttggc    1200
cctgactcct caaaggaggg gatcgacccg ctggtgttgt gattgctaga ccagagtagg    1260
tttggatggg cagggtgtta cttaaaaagt ataggatgac accggcgagc agtccggagc    1320
acaggctatc cccactcaaa gccagagatg gattctcggt ctcagctctc aaggttcctt    1380
ccccaggccc cacagtgcag agatagttct ggggccctgg gtgggtgggg cctctgtaca    1440
aggggcgggg ttcccgggcg cctcgtggcc agggtgaccc cgcccctcc tcctgcgcag     1500 cgctctgatt ccgcggagct gtccagcctc agtgccgggg ctggtcccct cttgtgcgcg    1560
gcgcctcctg gccggcttcc cgcctggttc ccgcgctggg ctcccgtcct cccgccccgc    1620
cttcgtcctg ccccgccgcg gccggtctac tgctccccgc gggcccgagc cggccgagcg    1680
gctgcccgcc ggggatctga acggcgcggc ggggccggaa gccgagggac ccgcggaggg    1740
gaccggcggc cccggacggc tgccggaggg gcggccgtgc gtggatgcgg cgggagctgg    1800
aagcctcgag                                                           1810

<210> SEQ ID NO 3
<211> LENGTH: 313
<212> TYPE: DNA
<213> ORGANISM: Artificial sequence
<220> FEATURE:
<223> OTHER INFORMATION: Synthetic nucleic acid

<400> SEQUENCE: 3
ctggtcccct cttgtgcgcg gcgcctcctg gccggcttcc cgcctggttc ccgcgctggg     60
ctcccgtcct cccgccccgc cttcgtcctg ccccgccgcg gccggtctac tgctccccgc    120
gggcccgagc cggccgagcg gctgcccgcc ggggatctga acggcgcggc ggggccggaa    180
gccgagggac ccgcggaggg gaccggcggc cccggacggc tgccggaggg gcggccgtgc    240
gtggatgcgg cgggagctgg aagcctcgag cagccggcgc cttctctggc cccgggcgcc    300
atatggcttg aag                                                       313

<210> SEQ ID NO 4
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 4

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110
```

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 5
<211> LENGTH: 340
<212> TYPE: PRT
<213> ORGANISM: Artificial sequence
<220> FEATURE:
<223> OTHER INFORMATION: Synthetic polypeptide

<400> SEQUENCE: 5

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
    20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

```
Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro Ala Ala Lys Ser Arg Ile Thr Ser Glu
305                 310                 315                 320

Gly Glu Tyr Ile Pro Leu Asp Gln Ile Asp Ile Asn Val Phe Cys Tyr
                325                 330                 335

Glu Asn Glu Val
            340

<210> SEQ ID NO 6
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 6

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175
```

```
Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
        290                 295                 300

Glu Ala Gly Ala Val Pro
305                 310

<210> SEQ ID NO 7
<211> LENGTH: 340
<212> TYPE: PRT
<213> ORGANISM: Artificial sequence
<220> FEATURE:
<223> OTHER INFORMATION: Synthetic polypeptide

<400> SEQUENCE: 7

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220
```

```
Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
            245                 250                 255

Lys Asn Cys Trp Gly Leu Leu Gly His Tyr Leu Arg Val Leu Ile His
        260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
290                 295                 300

Glu Ala Gly Ala Val Pro Ala Ala Ala Lys Ser Arg Ile Thr Ser Glu
305                 310                 315                 320

Gly Glu Tyr Ile Pro Leu Asp Gln Ile Asp Ile Asn Val Phe Cys Tyr
                325                 330                 335

Glu Asn Glu Val
            340

<210> SEQ ID NO 8
<211> LENGTH: 300
<212> TYPE: PRT
<213> ORGANISM: Artificial sequence
<220> FEATURE:
<223> OTHER INFORMATION: Synthetic polypeptide

<400> SEQUENCE: 8

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
    130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240
```

```
Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
                260                 265                 270

Tyr Gly Asp Ile Arg Lys Lys Gln Lys Ile Thr Ile Ala Gly Gln Glu
                275                 280                 285

Met Glu Val Glu Thr Leu Val Ala Glu Glu Asp
                290                 295                 300

<210> SEQ ID NO 9
<211> LENGTH: 330
<212> TYPE: PRT
<213> ORGANISM: Artificial sequence
<220> FEATURE:
<223> OTHER INFORMATION: Synthetic polypeptide

<400> SEQUENCE: 9

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
                20                  25                  30

Gly Trp Leu Arg Ser Arg Gly Thr Ser Ile Glu Lys Thr Ile Ala Ile
            35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
                100                 105                 110

Trp Met Arg Tyr Gly Glu Trp Leu Leu Thr Cys Pro Val Leu Leu Ile
            115                 120                 125

His Leu Ser Asn Leu Thr Gly Leu Lys Asp Asp Tyr Ser Lys Arg Thr
    130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
                180                 185                 190

Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
                260                 265                 270

Tyr Gly Asp Ile Arg Lys Lys Gln Lys Ile Thr Ile Ala Gly Gln Glu
                275                 280                 285

Met Glu Val Glu Thr Leu Val Ala Glu Glu Asp Ala Ala Ala Lys
                290                 295                 300
```

Ser Arg Ile Thr Ser Glu Gly Glu Tyr Ile Pro Leu Asp Gln Ile Asp
305                 310                 315                 320

Ile Asn Val Phe Cys Tyr Glu Asn Glu Val
                325                 330

<210> SEQ ID NO 10
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 10

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 11
<211> LENGTH: 374
<212> TYPE: PRT
<213> ORGANISM: Artificial sequence
<220> FEATURE:
<223> OTHER INFORMATION: Synthetic polypeptide

<400> SEQUENCE: 11

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp Ala Ala Ala Lys Ser Arg Ile Thr
            340                 345                 350

-continued

Ser Gly Glu Tyr Ile Pro Leu Asp Gln Ile Asp Ile Asn Val Phe
    355                 360                 365

Cys Tyr Glu Asn Glu Val
    370

<210> SEQ ID NO 12
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 12

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Val Tyr Gly Ser Thr Val Gly His
        275                 280                 285

Thr Ile Ile Asp Leu Met Ser Lys Asn Cys Trp Gly Leu Leu Gly His
    290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

```
Thr Leu Val Glu Asp Glu Ala Glu Ala Gly Ala Val
            340                 345
```

<210> SEQ ID NO 13
<211> LENGTH: 378
<212> TYPE: PRT
<213> ORGANISM: Artificial sequence
<220> FEATURE:
<223> OTHER INFORMATION: Synthetic polypeptide

<400> SEQUENCE: 13

```
Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Val Tyr Gly Ser Thr Val Gly His
        275                 280                 285

Thr Ile Ile Asp Leu Met Ser Lys Asn Cys Trp Gly Leu Leu Gly His
    290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val Ala Ala Ala Lys
            340                 345                 350
```

-continued

```
Ser Arg Ile Thr Ser Glu Gly Glu Tyr Ile Pro Leu Asp Gln Ile Asp
        355                 360                 365

Ile Asn Val Phe Cys Tyr Glu Asn Glu Val
    370                 375

<210> SEQ ID NO 14
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 14

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Thr Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Glu Met Met Lys Ser Ile Ile Glu Ala Phe His Glu Phe Asp Ser
    130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
    210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Pro Tyr Gly Ser Ala Ile Gly
        275                 280                 285

His Ser Ile Leu Asp Leu Ile Ala Lys Asn Met Trp Gly Val Leu Gly
    290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335
```

Glu Thr Leu Val Ala Glu Glu Asp Lys Tyr Glu Ser Ser
              340                 345                 350

<210> SEQ ID NO 15
<211> LENGTH: 380
<212> TYPE: PRT
<213> ORGANISM: Artificial sequence
<220> FEATURE:
<223> OTHER INFORMATION: Synthetic polypeptide

<400> SEQUENCE: 15

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Thr Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Glu Met Met Lys Ser Ile Ile Glu Ala Phe His Glu Phe Asp Ser
130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Pro Tyr Gly Ser Ala Ile Gly
        275                 280                 285

His Ser Ile Leu Asp Leu Ile Ala Lys Asn Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser Ala Ala
            340                 345                 350

Ala Lys Ser Arg Ile Thr Ser Glu Gly Glu Tyr Ile Pro Leu Asp Gln
        355                 360                 365

Ile Asp Ile Asn Val Phe Cys Tyr Glu Asn Glu Val
370                 375                 380

<210> SEQ ID NO 16
<211> LENGTH: 316
<212> TYPE: PRT
<213> ORGANISM: Artificial sequence
<220> FEATURE:
<223> OTHER INFORMATION: Synthetic polypeptide

<400> SEQUENCE: 16

Met Gly Gly Ala Pro Ala Pro Asp Ala His Ser Ala Pro Pro Gly Asn
1               5                   10                  15

Asp Ser Ala Gly Gly Ser Glu Tyr His Ala Pro Ala Gly Tyr Gln Val
            20                  25                  30

Asn Pro Pro Tyr His Pro Val His Gly Tyr Glu Glu Gln Cys Ser Ser
        35                  40                  45

Ile Tyr Ile Tyr Tyr Gly Ala Leu Trp Glu Gln Glu Thr Ala Arg Gly
    50                  55                  60

Phe Gln Trp Phe Ala Val Phe Leu Ser Ala Leu Phe Leu Ala Phe Tyr
65                  70                  75                  80

Gly Trp His Ala Tyr Lys Ala Ser Val Gly Trp Glu Glu Val Tyr Val
                85                  90                  95

Cys Ser Val Glu Leu Ile Lys Val Ile Leu Glu Ile Tyr Phe Glu Phe
            100                 105                 110

Thr Ser Pro Ala Met Leu Phe Leu Tyr Gly Gly Asn Ile Thr Pro Trp
        115                 120                 125

Leu Arg Tyr Ala Glu Trp Leu Leu Thr Cys Pro Val Ile Leu Ile His
    130                 135                 140

Leu Ser Asn Ile Thr Gly Leu Ser Glu Glu Tyr Asn Lys Arg Thr Met
145                 150                 155                 160

Ala Leu Leu Val Ser Asp Leu Gly Thr Ile Cys Met Gly Val Thr Ala
                165                 170                 175

Ala Leu Ala Thr Gly Trp Val Lys Trp Leu Phe Tyr Cys Ile Gly Leu
            180                 185                 190

Val Tyr Gly Thr Gln Thr Phe Tyr Asn Ala Gly Ile Ile Tyr Val Glu
        195                 200                 205

Ser Tyr Tyr Ile Met Pro Ala Gly Gly Cys Lys Lys Leu Val Leu Ala
    210                 215                 220

Met Thr Ala Val Tyr Tyr Ser Ser Trp Leu Met Phe Pro Gly Leu Phe
225                 230                 235                 240

Ile Phe Gly Pro Glu Gly Met His Thr Leu Ser Val Ala Gly Ser Thr
                245                 250                 255

Ile Gly His Thr Ile Ala Asp Leu Leu Ser Lys Asn Ile Trp Gly Leu
            260                 265                 270

Leu Gly His Phe Leu Arg Ile Lys Ile His Glu His Ile Ile Met Tyr
        275                 280                 285

Gly Asp Ile Arg Arg Pro Val Ser Ser Gln Phe Leu Gly Arg Lys Val
    290                 295                 300

Asp Val Leu Ala Phe Val Thr Glu Glu Asp Lys Val
305                 310                 315

<210> SEQ ID NO 17

<211> LENGTH: 346
<212> TYPE: PRT
<213> ORGANISM: Artificial sequence
<220> FEATURE:
<223> OTHER INFORMATION: Synthetic polypeptide

<400> SEQUENCE: 17

```
Met Gly Gly Ala Pro Ala Pro Asp Ala His Ser Ala Pro Pro Gly Asn
1               5                   10                  15

Asp Ser Ala Gly Gly Ser Glu Tyr His Ala Pro Ala Gly Tyr Gln Val
            20                  25                  30

Asn Pro Pro Tyr His Pro Val His Gly Tyr Glu Glu Gln Cys Ser Ser
        35                  40                  45

Ile Tyr Ile Tyr Tyr Gly Ala Leu Trp Glu Gln Glu Thr Ala Arg Gly
    50                  55                  60

Phe Gln Trp Phe Ala Val Phe Leu Ser Ala Leu Phe Leu Ala Phe Tyr
65                  70                  75                  80

Gly Trp His Ala Tyr Lys Ala Ser Val Gly Trp Glu Val Tyr Val
                85                  90                  95

Cys Ser Val Glu Leu Ile Lys Val Ile Leu Glu Ile Tyr Phe Glu Phe
                100                 105                 110

Thr Ser Pro Ala Met Leu Phe Leu Tyr Gly Gly Asn Ile Thr Pro Trp
            115                 120                 125

Leu Arg Tyr Ala Glu Trp Leu Leu Thr Cys Pro Val Ile Leu Ile His
130                 135                 140

Leu Ser Asn Ile Thr Gly Leu Ser Glu Tyr Asn Lys Arg Thr Met
145                 150                 155                 160

Ala Leu Leu Val Ser Asp Leu Gly Thr Ile Cys Met Gly Val Thr Ala
                165                 170                 175

Ala Leu Ala Thr Gly Trp Val Lys Trp Leu Phe Tyr Cys Ile Gly Leu
            180                 185                 190

Val Tyr Gly Thr Gln Thr Phe Tyr Asn Ala Gly Ile Ile Tyr Val Glu
        195                 200                 205

Ser Tyr Tyr Ile Met Pro Ala Gly Gly Cys Lys Lys Leu Val Leu Ala
    210                 215                 220

Met Thr Ala Val Tyr Tyr Ser Ser Trp Leu Met Phe Pro Gly Leu Phe
225                 230                 235                 240

Ile Phe Gly Pro Glu Gly Met His Thr Leu Ser Val Ala Gly Ser Thr
                245                 250                 255

Ile Gly His Thr Ile Ala Asp Leu Leu Ser Lys Asn Ile Trp Gly Leu
            260                 265                 270

Leu Gly His Phe Leu Arg Ile Lys Ile His Glu His Ile Ile Met Tyr
        275                 280                 285

Gly Asp Ile Arg Arg Pro Val Ser Ser Gln Phe Leu Gly Arg Lys Val
    290                 295                 300

Asp Val Leu Ala Phe Val Thr Glu Glu Asp Lys Val Ala Ala Ala Lys
305                 310                 315                 320

Ser Arg Ile Thr Ser Glu Gly Glu Tyr Ile Pro Leu Asp Gln Ile Asp
                325                 330                 335

Ile Asn Val Phe Cys Tyr Glu Asn Glu Val
            340                 345
```

<210> SEQ ID NO 18
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 18

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
    50                  55                  60

Glu Ala Thr Gly Gly Tyr Leu Val Val Gly Val Lys Lys Gln Ala
65                  70                  75                  80

Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
        115                 120                 125

Cys Cys Val Glu Val Leu Phe Val Thr Leu Glu Ile Phe Lys Glu Phe
    130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
                165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
        195                 200                 205

Gly Leu Ala Thr Asp Trp Leu Lys Trp Leu Leu Tyr Ile Val Ser Cys
    210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
                245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
        275                 280                 285

Ile Gly His Ser Ile Cys Asp Ile Ile Ala Lys Glu Phe Trp Thr Phe
    290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Val
                325                 330                 335

Glu Val Glu Glu Phe Val Glu Glu Glu Asp Glu Asp Thr Val
            340                 345                 350

<210> SEQ ID NO 19
<211> LENGTH: 380
<212> TYPE: PRT
<213> ORGANISM: Artificial sequence
<220> FEATURE:
<223> OTHER INFORMATION: Synthetic polypeptide

<400> SEQUENCE: 19

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
    50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
        115                 120                 125

Cys Cys Val Glu Val Leu Phe Val Thr Leu Glu Ile Phe Lys Glu Phe
130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
                165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
        195                 200                 205

Gly Leu Ala Thr Asp Trp Leu Lys Trp Leu Leu Tyr Ile Val Ser Cys
    210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
                245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
        275                 280                 285

Ile Gly His Ser Ile Cys Asp Ile Ile Ala Lys Glu Phe Trp Thr Phe
    290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Glu Val
                325                 330                 335

Glu Val Glu Glu Phe Val Glu Glu Asp Glu Asp Thr Val Ala Ala
            340                 345                 350

Ala Lys Ser Arg Ile Thr Ser Glu Gly Glu Tyr Ile Pro Leu Asp Gln
        355                 360                 365

Ile Asp Ile Asn Val Phe Cys Tyr Glu Asn Glu Val
    370                 375                 380

<210> SEQ ID NO 20
<211> LENGTH: 345
<212> TYPE: PRT
<213> ORGANISM: Artificial sequence
<220> FEATURE:
<223> OTHER INFORMATION: Synthetic polypeptide

<400> SEQUENCE: 20

Met Ser Arg Leu Val Ala Ala Ser Trp Leu Ala Leu Leu Leu Cys
1               5                   10                  15

Gly Ile Thr Ser Thr Thr Thr Ala Ser Ser Ala Pro Ala Ala Ser Ser
            20                  25                  30

Thr Asp Gly Thr Ala Ala Ala Val Ser His Tyr Ala Met Asn Gly
        35                  40                  45

Phe Asp Glu Leu Ala Lys Gly Ala Val Pro Glu Asp His Phe Val
    50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
            100                 105                 110

Lys Ala Thr Cys Gly Trp Glu Glu Val Tyr Val Cys Cys Val Glu Val
            115                 120                 125

Leu Phe Val Thr Leu Glu Ile Phe Lys Glu Phe Ser Ser Pro Ala Thr
130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
            180                 185                 190

Cys Val Gly Met Ile Val Phe Gly Met Ala Ala Gly Leu Ala Thr Asp
            195                 200                 205

Trp Leu Lys Trp Leu Leu Tyr Ile Val Ser Cys Ile Tyr Gly Gly Tyr
210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
            260                 265                 270

Gly Leu Leu Lys Leu Ser Pro Tyr Ala Asn Ser Ile Gly His Ser Ile
            275                 280                 285

Cys Asp Ile Ile Ala Lys Glu Phe Trp Thr Phe Leu Ala His His Leu
290                 295                 300

Arg Ile Lys Ile His Glu His Ile Leu Ile His Gly Asp Ile Arg Lys
305                 310                 315                 320

Thr Thr Lys Met Glu Ile Gly Gly Glu Glu Val Glu Val Glu Glu Phe
                325                 330                 335

Val Glu Glu Glu Asp Glu Asp Thr Val
            340                 345

<210> SEQ ID NO 21
<211> LENGTH: 375
<212> TYPE: PRT
<213> ORGANISM: Artificial sequence
<220> FEATURE:
<223> OTHER INFORMATION: Synthetic polypeptide

<400> SEQUENCE: 21

| | | | | | | | | | | | | | | | |
|---|---|---|---|---|---|---|---|---|---|---|---|---|---|---|---|
| Met | Ser | Arg | Leu | Val | Ala | Ala | Ser | Trp | Leu | Leu | Ala | Leu | Leu | Leu | Cys |
| 1 | | | | 5 | | | | | 10 | | | | | 15 | |
| Gly | Ile | Thr | Ser | Thr | Thr | Thr | Ala | Ser | Ser | Ala | Pro | Ala | Ala | Ser | Ser |
| | | | 20 | | | | | 25 | | | | | 30 | | |
| Thr | Asp | Gly | Thr | Ala | Ala | Ala | Val | Ser | His | Tyr | Ala | Met | Asn | Gly | |
| | | 35 | | | | | 40 | | | | | 45 | | | |
| Phe | Asp | Glu | Leu | Ala | Lys | Gly | Ala | Val | Val | Pro | Glu | Asp | His | Phe | Val |
| | 50 | | | | | 55 | | | | | 60 | | | | |
| Cys | Gly | Pro | Ala | Asp | Lys | Cys | Tyr | Cys | Ser | Ala | Trp | Leu | His | Ser | Arg |
| 65 | | | | | 70 | | | | | 75 | | | | | 80 |
| Gly | Thr | Pro | Gly | Glu | Lys | Ile | Gly | Ala | Gln | Val | Cys | Gln | Trp | Ile | Ala |
| | | | | 85 | | | | | 90 | | | | | 95 | |
| Phe | Ser | Ile | Ala | Ile | Ala | Leu | Leu | Thr | Phe | Tyr | Gly | Phe | Ser | Ala | Trp |
| | | | 100 | | | | | 105 | | | | | 110 | | |
| Lys | Ala | Thr | Cys | Gly | Trp | Glu | Glu | Val | Tyr | Val | Cys | Cys | Val | Glu | Val |
| | | | 115 | | | | | 120 | | | | | 125 | | |
| Leu | Phe | Val | Thr | Leu | Glu | Ile | Phe | Lys | Glu | Phe | Ser | Ser | Pro | Ala | Thr |
| | 130 | | | | | 135 | | | | | 140 | | | | |
| Val | Tyr | Leu | Ser | Thr | Gly | Asn | His | Ala | Tyr | Cys | Leu | Arg | Tyr | Phe | Glu |
| 145 | | | | | 150 | | | | | 155 | | | | | 160 |
| Trp | Leu | Leu | Ser | Cys | Pro | Val | Ile | Leu | Ile | Lys | Leu | Ser | Asn | Leu | Ser |
| | | | | 165 | | | | | 170 | | | | | 175 | |
| Gly | Leu | Lys | Asn | Asp | Tyr | Ser | Lys | Arg | Thr | Met | Gly | Leu | Ile | Val | Ser |
| | | | 180 | | | | | 185 | | | | | 190 | | |
| Cys | Val | Gly | Met | Ile | Val | Phe | Gly | Met | Ala | Ala | Gly | Leu | Ala | Thr | Asp |
| | | 195 | | | | | 200 | | | | | 205 | | | |
| Trp | Leu | Lys | Trp | Leu | Leu | Tyr | Ile | Val | Ser | Cys | Ile | Tyr | Gly | Gly | Tyr |
| | 210 | | | | | 215 | | | | | 220 | | | | |
| Met | Tyr | Phe | Gln | Ala | Ala | Lys | Cys | Tyr | Val | Glu | Ala | Asn | His | Ser | Val |
| 225 | | | | | 230 | | | | | 235 | | | | | 240 |
| Pro | Lys | Gly | His | Cys | Arg | Met | Val | Val | Lys | Leu | Met | Ala | Tyr | Ala | Tyr |
| | | | | 245 | | | | | 250 | | | | | 255 | |
| Phe | Ala | Ser | Trp | Gly | Ser | Tyr | Pro | Ile | Leu | Trp | Ala | Val | Gly | Pro | Glu |
| | | | 260 | | | | | 265 | | | | | 270 | | |
| Gly | Leu | Leu | Lys | Leu | Ser | Pro | Tyr | Ala | Asn | Ser | Ile | Gly | His | Ser | Ile |
| | | 275 | | | | | 280 | | | | | 285 | | | |
| Cys | Asp | Ile | Ile | Ala | Lys | Glu | Phe | Trp | Thr | Phe | Leu | Ala | His | His | Leu |
| 290 | | | | | 295 | | | | | 300 | | | | | |
| Arg | Ile | Lys | Ile | His | Glu | His | Ile | Leu | Ile | His | Gly | Asp | Ile | Arg | Lys |
| 305 | | | | | 310 | | | | | 315 | | | | | 320 |
| Thr | Thr | Lys | Met | Glu | Ile | Gly | Gly | Glu | Glu | Val | Glu | Val | Glu | Glu | Phe |
| | | | | 325 | | | | | 330 | | | | | 335 | |
| Val | Glu | Glu | Glu | Asp | Glu | Asp | Thr | Val | Ala | Ala | Ala | Lys | Ser | Arg | Ile |
| | | | 340 | | | | | 345 | | | | | 350 | | |
| Thr | Ser | Glu | Gly | Glu | Tyr | Ile | Pro | Leu | Asp | Gln | Ile | Asp | Ile | Asn | Val |
| | | | | 355 | | | | | 360 | | | | | 365 | |
| Phe | Cys | Tyr | Glu | Asn | Glu | Val | | | | | | | | | |
| | 370 | | | | | 375 | | | | | | | | | |

<210> SEQ ID NO 22
<211> LENGTH: 325
<212> TYPE: PRT
<213> ORGANISM: Artificial sequence
<220> FEATURE:
<223> OTHER INFORMATION: Synthetic polypeptide

<400> SEQUENCE: 22

Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Val Val
            20                  25                  30

Thr Pro Ala Ala Asp Ala His Gly Glu Thr Ser Asn Ala Thr Thr Ala
            35                  40                  45

Gly Ala Asp His Gly Cys Phe Pro His Ile Asn His Gly Thr Glu Leu
        50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
        115                 120                 125

Asn Gly Gly Ala Val Ile Trp Leu Arg Tyr Ser Met Trp Leu Leu Thr
    130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
        195                 200                 205

Ile Ala Lys Val Tyr Ile Glu Ser Tyr His Thr Leu Pro Lys Gly Val
    210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
            260                 265                 270

Ser Lys Asn Thr Trp Gly Phe Leu Gly His His Leu Arg Val Lys Ile
        275                 280                 285

His Glu His Ile Leu Ile His Gly Asp Ile Arg Lys Thr Thr Thr Ile
    290                 295                 300

Asn Val Ala Gly Glu Asn Met Glu Ile Glu Thr Phe Val Asp Glu Glu
305                 310                 315                 320

Glu Glu Gly Gly Val
            325

<210> SEQ ID NO 23
<211> LENGTH: 355
<212> TYPE: PRT
<213> ORGANISM: Artificial sequence
<220> FEATURE:
<223> OTHER INFORMATION: Synthetic polypeptide

<400> SEQUENCE: 23

Met Glu Thr Ala Ala Thr Met Thr His Ala Phe Ile Ser Ala Val Pro

```
  1               5                   10                  15
Ser Ala Glu Ala Thr Ile Arg Gly Leu Leu Ser Ala Ala Val Val
              20                  25                  30

Thr Pro Ala Ala Asp Ala His Gly Glu Thr Ser Asn Ala Thr Thr Ala
              35                  40                  45

Gly Ala Asp His Gly Cys Phe Pro His Ile Asn His Gly Thr Glu Leu
          50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                  85                  90                  95

Gly Trp Glu Glu Val Tyr Val Cys Val Ile Glu Leu Val Lys Cys Phe
              100                 105                 110

Ile Glu Leu Phe His Glu Val Asp Ser Pro Ala Thr Val Tyr Gln Thr
              115                 120                 125

Asn Gly Gly Ala Val Ile Trp Leu Arg Tyr Ser Met Trp Leu Leu Thr
          130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                  165                 170                 175

Ile Val Trp Gly Ile Thr Ala Ala Phe Thr Lys Gly Pro Leu Lys Ile
              180                 185                 190

Leu Phe Phe Met Ile Gly Leu Phe Tyr Gly Val Thr Cys Phe Phe Gln
              195                 200                 205

Ile Ala Lys Val Tyr Ile Glu Ser Tyr His Thr Leu Pro Lys Gly Val
          210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                  245                 250                 255

Ile Thr Pro Tyr Thr Ser Gly Ile Gly His Leu Ile Leu Asp Leu Ile
              260                 265                 270

Ser Lys Asn Thr Trp Gly Phe Leu Gly His His Leu Arg Val Lys Ile
              275                 280                 285

His Glu His Ile Leu Ile His Gly Asp Ile Arg Lys Thr Thr Thr Ile
          290                 295                 300

Asn Val Ala Gly Glu Asn Met Glu Ile Glu Thr Phe Val Asp Glu Glu
305                 310                 315                 320

Glu Glu Gly Gly Val Ala Ala Ala Lys Ser Arg Ile Thr Ser Glu Gly
              325                 330                 335

Glu Tyr Ile Pro Leu Asp Gln Ile Asp Ile Asn Val Phe Cys Tyr Glu
              340                 345                 350

Asn Glu Val
          355

<210> SEQ ID NO 24
<211> LENGTH: 258
<212> TYPE: PRT
<213> ORGANISM: Artificial sequence
<220> FEATURE:
<223> OTHER INFORMATION: Synthetic polypeptide

<400> SEQUENCE: 24

Met Asp Pro Ile Ala Leu Gln Ala Gly Tyr Asp Leu Leu Gly Asp Gly
```

```
               1               5                  10                 15
            Arg Pro Glu Thr Leu Trp Leu Gly Ile Gly Thr Leu Met Leu Ile
                           20                 25                 30
            Gly Thr Phe Tyr Phe Leu Val Arg Gly Trp Gly Val Thr Asp Lys Asp
                           35                 40                 45
            Ala Arg Glu Tyr Tyr Ala Val Thr Ile Leu Val Pro Gly Ile Ala Ser
                50                    55                 60
            Ala Ala Tyr Leu Ser Met Phe Phe Gly Ile Gly Leu Thr Glu Val Thr
             65                    70                 75                 80
            Val Gly Gly Glu Met Leu Asp Ile Tyr Tyr Ala Arg Tyr Ala Asp Trp
                           85                 90                 95
            Leu Phe Thr Thr Pro Leu Leu Leu Asp Leu Ala Leu Leu Ala Lys
                           100                105                110
            Val Asp Arg Val Thr Ile Gly Thr Leu Val Gly Val Asp Ala Leu Met
                           115                120                125
            Ile Val Thr Gly Leu Ile Gly Ala Leu Ser His Thr Ala Ile Ala Arg
                           130                135                140
            Tyr Ser Trp Trp Leu Phe Ser Thr Ile Cys Met Ile Val Val Leu Tyr
            145                    150                155                160
            Phe Leu Ala Thr Ser Leu Arg Ser Ala Ala Lys Glu Arg Gly Pro Glu
                           165                170                175
            Val Ala Ser Thr Phe Asn Thr Leu Thr Ala Leu Val Leu Val Leu Trp
                           180                185                190
            Thr Ala Tyr Pro Ile Leu Trp Ile Ile Gly Thr Glu Gly Ala Gly Val
                           195                200                205
            Val Gly Leu Gly Ile Glu Thr Leu Leu Phe Met Val Leu Asp Val Thr
                           210                215                220
            Ala Lys Val Gly Phe Gly Phe Ile Leu Leu Arg Ser Arg Ala Ile Leu
            225                    230                235                240
            Gly Asp Thr Glu Ala Pro Glu Pro Ser Ala Gly Ala Asp Val Ser Ala
                           245                250                255
            Ala Asp

<210> SEQ ID NO 25
<211> LENGTH: 293
<212> TYPE: PRT
<213> ORGANISM: Artificial sequence
<220> FEATURE:
<223> OTHER INFORMATION: Synthetic polypeptide

<400> SEQUENCE: 25

Met Asp Pro Ile Ala Leu Gln Ala Gly Tyr Asp Leu Leu Gly Asp Gly
1               5                  10                 15
Arg Pro Glu Thr Leu Trp Leu Gly Ile Gly Thr Leu Met Leu Ile
               20                 25                 30
Gly Thr Phe Tyr Phe Leu Val Arg Gly Trp Gly Val Thr Asp Lys Asp
               35                 40                 45
Ala Arg Glu Tyr Tyr Ala Val Thr Ile Leu Val Pro Gly Ile Ala Ser
    50                    55                 60
Ala Ala Tyr Leu Ser Met Phe Phe Gly Ile Gly Leu Thr Glu Val Thr
 65                    70                 75                 80
Val Gly Gly Glu Met Leu Asp Ile Tyr Tyr Ala Arg Tyr Ala Asp Trp
               85                 90                 95
Leu Phe Thr Thr Pro Leu Leu Leu Asp Leu Ala Leu Leu Ala Lys
               100                105                110
```

```
Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
        130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Arg Pro Val Val Ala Ala Ala Lys Ser Arg Ile Thr Ser
            260                 265                 270

Glu Gly Glu Tyr Ile Pro Leu Asp Gln Ile Asp Ile Asn Val Phe Cys
        275                 280                 285

Tyr Glu Asn Glu Val
        290

<210> SEQ ID NO 26
<211> LENGTH: 248
<212> TYPE: PRT
<213> ORGANISM: Artificial sequence
<220> FEATURE:
<223> OTHER INFORMATION: Synthetic polypeptide

<400> SEQUENCE: 26

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Ile Val Lys Gly Trp Gly Val Thr Asp Lys Glu
        35                  40                  45

Ala Arg Glu Tyr Tyr Ser Ile Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Ala Gly Glu Val Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Ser Ile Gly Thr Leu Val Gly Val Asp Ala Leu Met
            115                 120                 125

Ile Val Thr Gly Leu Ile Gly Ala Leu Ser His Thr Pro Leu Ala Arg
        130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
                165                 170                 175
```

-continued

```
Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
            210                 215                 220

Ala Lys Val Gly Phe Gly Phe Ile Leu Arg Ser Arg Ala Ile Leu
225                 230                 235                 240

Gly Asp Thr Glu Ala Pro Glu Pro
                245
```

<210> SEQ ID NO 27
<211> LENGTH: 278
<212> TYPE: PRT
<213> ORGANISM: Artificial sequence
<220> FEATURE:
<223> OTHER INFORMATION: Synthetic polypeptide

<400> SEQUENCE: 27

```
Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Ile Val Lys Gly Trp Gly Val Thr Asp Lys Glu
        35                  40                  45

Ala Arg Glu Tyr Tyr Ser Ile Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Ala Gly Glu Val Leu Asp Ile Tyr Tyr Ala Arg Tyr Ala Asp Trp
                85                  90                  95

Leu Phe Thr Thr Pro Leu Leu Leu Asp Leu Ala Leu Leu Ala Lys
            100                 105                 110

Val Asp Arg Val Ser Ile Gly Thr Leu Val Gly Val Asp Ala Leu Met
            115                 120                 125

Ile Val Thr Gly Leu Ile Gly Ala Leu Ser His Thr Pro Leu Ala Arg
        130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
            210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ala Ala Lys Ser Arg Ile Thr
                245                 250                 255

Ser Glu Gly Glu Tyr Ile Pro Leu Asp Gln Ile Asp Ile Asn Val Phe
            260                 265                 270

Cys Tyr Glu Asn Glu Val
            275
```

```
<210> SEQ ID NO 28
<211> LENGTH: 242
<212> TYPE: PRT
<213> ORGANISM: Artificial sequence
<220> FEATURE:
<223> OTHER INFORMATION: Synthetic polypeptide

<400> SEQUENCE: 28
```

Met Leu Val Gly Glu Gly Ala Lys Leu Asp Val His Gly Cys Lys Thr
1               5                   10                  15

Val Asp Met Ala Ser Ser Phe Gly Lys Ala Leu Leu Glu Phe Val Phe
            20                  25                  30

Ile Val Phe Ala Cys Ile Thr Leu Leu Gly Ile Asn Ala Ala Lys
        35                  40                  45

Ser Lys Ala Ala Ser Arg Val Leu Phe Pro Ala Thr Phe Val Thr Gly
50                  55                  60

Ile Ala Ser Ile Ala Tyr Phe Ser Met Ala Ser Gly Gly Gly Trp Val
65                  70                  75                  80

Ile Ala Pro Asp Cys Arg Gln Leu Phe Val Ala Arg Tyr Leu Asp Trp
                85                  90                  95

Leu Ile Thr Thr Pro Leu Leu Leu Ile Asp Leu Gly Leu Val Ala Gly
            100                 105                 110

Val Ser Arg Trp Asp Ile Met Ala Leu Cys Leu Ser Asp Val Leu Met
        115                 120                 125

Ile Ala Thr Gly Ala Phe Gly Ser Leu Thr Val Gly Asn Val Lys Trp
130                 135                 140

Val Trp Trp Phe Phe Gly Met Cys Trp Phe Leu His Ile Ile Phe Ala
145                 150                 155                 160

Leu Gly Lys Ser Trp Ala Glu Ala Ala Lys Ala Lys Gly Gly Asp Ser
                165                 170                 175

Ala Ser Val Tyr Ser Lys Ile Ala Gly Ile Thr Val Ile Thr Trp Phe
            180                 185                 190

Cys Tyr Pro Val Val Trp Val Phe Ala Glu Gly Phe Gly Asn Phe Ser
        195                 200                 205

Val Thr Phe Glu Val Leu Ile Tyr Gly Val Leu Asp Val Ile Ser Lys
210                 215                 220

Ala Val Phe Gly Leu Ile Leu Met Ser Gly Ala Ala Thr Gly Tyr Glu
225                 230                 235                 240

Ser Ile

```
<210> SEQ ID NO 29
<211> LENGTH: 272
<212> TYPE: PRT
<213> ORGANISM: Artificial sequence
<220> FEATURE:
<223> OTHER INFORMATION: Synthetic polypeptide

<400> SEQUENCE: 29
```

Met Leu Val Gly Glu Gly Ala Lys Leu Asp Val His Gly Cys Lys Thr
1               5                   10                  15

Val Asp Met Ala Ser Ser Phe Gly Lys Ala Leu Leu Glu Phe Val Phe
            20                  25                  30

Ile Val Phe Ala Cys Ile Thr Leu Leu Gly Ile Asn Ala Ala Lys
        35                  40                  45

Ser Lys Ala Ala Ser Arg Val Leu Phe Pro Ala Thr Phe Val Thr Gly
50                  55                  60

```
Ile Ala Ser Ile Ala Tyr Phe Ser Met Ala Ser Gly Gly Gly Trp Val
 65                  70                  75                  80

Ile Ala Pro Asp Cys Arg Gln Leu Phe Val Ala Arg Tyr Leu Asp Trp
                 85                  90                  95

Leu Ile Thr Thr Pro Leu Leu Leu Ile Asp Leu Gly Leu Val Ala Gly
            100                 105                 110

Val Ser Arg Trp Asp Ile Met Ala Leu Cys Leu Ser Asp Val Leu Met
        115                 120                 125

Ile Ala Thr Gly Ala Phe Gly Ser Leu Thr Val Gly Asn Val Lys Trp
    130                 135                 140

Val Trp Trp Phe Phe Gly Met Cys Trp Phe Leu His Ile Ile Phe Ala
145                 150                 155                 160

Leu Gly Lys Ser Trp Ala Glu Ala Ala Lys Ala Lys Gly Gly Asp Ser
                165                 170                 175

Ala Ser Val Tyr Ser Lys Ile Ala Gly Ile Thr Val Ile Thr Trp Phe
            180                 185                 190

Cys Tyr Pro Val Val Trp Val Phe Ala Glu Gly Phe Gly Asn Phe Ser
        195                 200                 205

Val Thr Phe Glu Val Leu Ile Tyr Gly Val Leu Asp Val Ile Ser Lys
    210                 215                 220

Ala Val Phe Gly Leu Ile Leu Met Ser Gly Ala Ala Thr Gly Tyr Glu
225                 230                 235                 240

Ser Ile Ala Ala Ala Lys Ser Arg Ile Thr Ser Glu Gly Glu Tyr Ile
                245                 250                 255

Pro Leu Asp Gln Ile Asp Ile Asn Val Phe Cys Tyr Glu Asn Glu Val
            260                 265                 270

<210> SEQ ID NO 30
<211> LENGTH: 262
<212> TYPE: PRT
<213> ORGANISM: Artificial sequence
<220> FEATURE:
<223> OTHER INFORMATION: Synthetic polypeptide

<400> SEQUENCE: 30

Met Ala Pro Leu Ala Gln Asp Trp Thr Tyr Ala Glu Trp Ser Ala Val
  1               5                  10                  15

Tyr Asn Ala Leu Ser Phe Gly Ile Ala Gly Met Gly Ser Ala Thr Ile
                 20                  25                  30

Phe Phe Trp Leu Gln Leu Pro Asn Val Thr Lys Asn Tyr Arg Thr Ala
             35                  40                  45

Leu Thr Ile Thr Gly Ile Val Thr Leu Ile Ala Thr Tyr His Tyr Phe
     50                  55                  60

Arg Ile Phe Asn Ser Trp Val Ala Ala Phe Asn Val Gly Leu Gly Val
 65                  70                  75                  80

Asn Gly Ala Tyr Glu Val Thr Val Ser Gly Thr Pro Phe Asn Asp Ala
                 85                  90                  95

Tyr Arg Tyr Val Asp Trp Leu Leu Thr Val Pro Leu Leu Leu Val Glu
                100                 105                 110

Leu Ile Leu Val Met Lys Leu Pro Ala Lys Glu Thr Val Cys Leu Ala
            115                 120                 125

Trp Thr Leu Gly Ile Ala Ser Ala Val Met Val Ala Leu Gly Tyr Pro
    130                 135                 140

Gly Glu Ile Gln Asp Asp Leu Ser Val Arg Trp Phe Trp Trp Ala Cys
145                 150                 155                 160
```

```
Ala Met Val Pro Phe Val Tyr Val Gly Thr Leu Val Val Gly Leu
            165                 170                 175

Gly Ala Ala Thr Ala Lys Gln Pro Glu Gly Val Val Asp Leu Val Ser
            180                 185                 190

Ala Ala Arg Tyr Leu Thr Val Val Ser Trp Leu Thr Tyr Pro Phe Val
            195                 200                 205

Tyr Ile Val Lys Asn Ile Gly Leu Ala Gly Ser Thr Ala Thr Met Tyr
        210                 215                 220

Glu Gln Ile Gly Tyr Ser Ala Ala Asp Val Thr Ala Lys Ala Val Phe
225                 230                 235                 240

Gly Val Leu Ile Trp Ala Ile Ala Asn Ala Lys Ser Arg Leu Glu Glu
            245                 250                 255

Glu Gly Lys Leu Arg Ala
            260
```

<210> SEQ ID NO 31
<211> LENGTH: 292
<212> TYPE: PRT
<213> ORGANISM: Artificial sequence
<220> FEATURE:
<223> OTHER INFORMATION: Synthetic polypeptide

<400> SEQUENCE: 31

```
Met Ala Pro Leu Ala Gln Asp Trp Thr Tyr Ala Glu Trp Ser Ala Val
1               5                   10                  15

Tyr Asn Ala Leu Ser Phe Gly Ile Ala Gly Met Gly Ser Ala Thr Ile
            20                  25                  30

Phe Phe Trp Leu Gln Leu Pro Asn Val Thr Lys Asn Tyr Arg Thr Ala
        35                  40                  45

Leu Thr Ile Thr Gly Ile Val Thr Leu Ile Ala Thr Tyr His Tyr Phe
    50                  55                  60

Arg Ile Phe Asn Ser Trp Val Ala Ala Phe Asn Val Gly Leu Gly Val
65                  70                  75                  80

Asn Gly Ala Tyr Glu Val Thr Val Ser Gly Thr Pro Phe Asn Asp Ala
            85                  90                  95

Tyr Arg Tyr Val Asp Trp Leu Leu Thr Val Pro Leu Leu Leu Val Glu
            100                 105                 110

Leu Ile Leu Val Met Lys Leu Pro Ala Lys Glu Thr Val Cys Leu Ala
        115                 120                 125

Trp Thr Leu Gly Ile Ala Ser Ala Val Met Val Ala Leu Gly Tyr Pro
    130                 135                 140

Gly Glu Ile Gln Asp Asp Leu Ser Val Arg Trp Phe Trp Trp Ala Cys
145                 150                 155                 160

Ala Met Val Pro Phe Val Tyr Val Gly Thr Leu Val Val Gly Leu
            165                 170                 175

Gly Ala Ala Thr Ala Lys Gln Pro Glu Gly Val Val Asp Leu Val Ser
            180                 185                 190

Ala Ala Arg Tyr Leu Thr Val Val Ser Trp Leu Thr Tyr Pro Phe Val
            195                 200                 205

Tyr Ile Val Lys Asn Ile Gly Leu Ala Gly Ser Thr Ala Thr Met Tyr
        210                 215                 220

Glu Gln Ile Gly Tyr Ser Ala Ala Asp Val Thr Ala Lys Ala Val Phe
225                 230                 235                 240

Gly Val Leu Ile Trp Ala Ile Ala Asn Ala Lys Ser Arg Leu Glu Glu
            245                 250                 255
```

-continued

Glu Gly Lys Leu Arg Ala Ala Ala Lys Ser Arg Ile Thr Ser Glu
        260                 265                 270

Gly Glu Tyr Ile Pro Leu Asp Gln Ile Asp Ile Asn Val Phe Cys Tyr
            275                 280                 285

Glu Asn Glu Val
    290

<210> SEQ ID NO 32
<211> LENGTH: 313
<212> TYPE: PRT
<213> ORGANISM: Artificial sequence
<220> FEATURE:
<223> OTHER INFORMATION: Synthetic polypeptide

<400> SEQUENCE: 32

Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
        35                  40                  45

Asp Ser Gly Ser Lys Thr Leu Trp Val Val Phe Val Leu Met Leu Ile
    50                  55                  60

Ala Ser Ala Ala Phe Thr Ala Leu Ser Trp Lys Ile Pro Val Asn Arg
65                  70                  75                  80

Arg Leu Tyr His Val Ile Thr Thr Ile Ile Thr Leu Thr Ala Ala Leu
                85                  90                  95

Ser Tyr Phe Ala Met Ala Thr Gly His Gly Val Ala Leu Asn Lys Ile
            100                 105                 110

Val Ile Arg Thr Gln His Asp His Val Pro Asp Thr Tyr Glu Thr Val
        115                 120                 125

Tyr Arg Gln Val Tyr Tyr Ala Arg Tyr Ile Asp Trp Ala Ile Thr Thr
    130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
    210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
        275                 280                 285

Val Glu Leu Asn Gly Phe Trp Ala Asn Gly Leu Asn Arg Glu Gly Ala
    290                 295                 300

Ile Arg Ile Gly Glu Asp Asp Gly Ala
305                 310

<210> SEQ ID NO 33
<211> LENGTH: 351
<212> TYPE: PRT
<213> ORGANISM: Artificial sequence
<220> FEATURE:
<223> OTHER INFORMATION: Synthetic polypeptide

<400> SEQUENCE: 33

Met Ile Val Asp Gln Phe Glu Val Leu Met Lys Thr Ser Gln Leu
1               5                   10                  15

Phe Pro Leu Pro Thr Ala Thr Gln Ser Ala Gln Pro Thr His Val Ala
                20                  25                  30

Pro Val Pro Thr Val Leu Pro Asp Thr Pro Ile Tyr Glu Thr Val Gly
            35                  40                  45

Asp Ser Gly Ser Lys Thr Leu Trp Val Val Phe Val Leu Met Leu Ile
50                  55                  60

Ala Ser Ala Ala Phe Thr Ala Leu Ser Trp Lys Ile Pro Val Asn Arg
65                  70                  75                  80

Arg Leu Tyr His Val Ile Thr Ile Ile Thr Leu Thr Ala Ala Leu
                85                  90                  95

Ser Tyr Phe Ala Met Ala Thr Gly His Gly Val Ala Leu Asn Lys Ile
                100                 105                 110

Val Ile Arg Thr Gln His Asp His Val Pro Asp Thr Tyr Glu Thr Val
            115                 120                 125

Tyr Arg Gln Val Tyr Tyr Ala Arg Tyr Ile Asp Trp Ala Ile Thr Thr
        130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
        275                 280                 285

Val Glu Leu Asn Gly Phe Trp Ala Asn Gly Leu Asn Arg Glu Gly Ala
290                 295                 300

Ile Arg Ile Gly Glu Asp Asp Gly Ala Arg Pro Val Ala Val Ser
305                 310                 315                 320

Lys Ala Ala Ala Lys Ser Arg Ile Thr Ser Glu Gly Glu Tyr Ile Pro
                325                 330                 335

Leu Asp Gln Ile Asp Ile Asn Val Phe Cys Tyr Glu Asn Glu Val
            340                 345                 350

<210> SEQ ID NO 34

<211> LENGTH: 291
<212> TYPE: PRT
<213> ORGANISM: Artificial sequence
<220> FEATURE:
<223> OTHER INFORMATION: Synthetic polypeptide

<400> SEQUENCE: 34

```
Met Thr Glu Thr Leu Pro Pro Val Thr Glu Ser Ala Val Ala Leu Gln
 1               5                  10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
 50                  55                  60

Lys Leu Ile Ala Val Ser Thr Ile Leu Val Pro Val Ser Ile Ala
 65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp
    290
```

<210> SEQ ID NO 35
<211> LENGTH: 320
<212> TYPE: PRT
<213> ORGANISM: Artificial sequence
<220> FEATURE:
<223> OTHER INFORMATION: Synthetic polypeptide

<400> SEQUENCE: 35

```
Met Thr Glu Thr Leu Pro Pro Val Thr Glu Ser Ala Val Ala Leu Gln
 1               5                  10                  15

Ala Glu Val Thr Gln Arg Glu Leu Phe Glu Phe Val Leu Asn Asp Pro
```

```
                    20                  25                  30
Leu Leu Ala Ser Ser Leu Tyr Ile Asn Ile Ala Leu Ala Gly Leu Ser
                35                  40                  45

Ile Leu Leu Phe Val Phe Met Thr Arg Gly Leu Asp Asp Pro Arg Ala
 50                  55                  60

Lys Leu Ile Ala Val Ser Thr Ile Leu Val Pro Val Val Ser Ile Ala
 65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
                100                 105                 110

Glu Val Asp Gly Val Val Thr Met Trp Gly Arg Tyr Leu Thr Trp Ala
                115                 120                 125

Leu Ser Thr Pro Met Ile Leu Leu Ala Leu Gly Leu Leu Ala Gly Ser
            130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
                180                 185                 190

Ile Leu Leu Val Glu Trp Ala Gln Asp Ala Lys Ala Ala Gly Thr Ala
                195                 200                 205

Asp Met Phe Asn Thr Leu Lys Leu Leu Thr Val Val Met Trp Leu Gly
            210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
                260                 265                 270

Val Val Ser Gly Ser Ile Leu Asp Val Pro Ser Ala Ser Gly Thr Pro
                275                 280                 285

Ala Asp Asp Ala Ala Ala Lys Ser Arg Ile Thr Ser Glu Gly Glu Tyr
            290                 295                 300

Ile Pro Leu Asp Gln Ile Asp Ile Asn Phe Cys Tyr Glu Asn Glu Val
305                 310                 315                 320

<210> SEQ ID NO 36
<211> LENGTH: 303
<212> TYPE: PRT
<213> ORGANISM: Artificial sequence
<220> FEATURE:
<223> OTHER INFORMATION: Synthetic polypeptide

<400> SEQUENCE: 36

Met Val Thr Gln Arg Glu Leu Phe Glu Phe Val Leu Asn Asp Pro Leu
 1               5                  10                  15

Leu Ala Ser Ser Leu Tyr Ile Asn Ile Ala Leu Ala Gly Leu Ser Ile
                20                  25                  30

Leu Leu Phe Val Phe Met Thr Arg Gly Leu Asp Asp Pro Arg Ala Lys
                35                  40                  45

Leu Ile Ala Val Ser Thr Ile Leu Val Pro Val Val Ser Ile Ala Ser
 50                  55                  60

Tyr Thr Gly Leu Ala Ser Gly Leu Thr Ile Ser Val Leu Glu Met Pro
```

```
                65                  70                  75                  80
Ala Gly His Phe Ala Glu Gly Ser Ser Val Met Leu Gly Gly Glu Glu
                    85                  90                  95

Val Asp Gly Val Val Thr Met Trp Gly Arg Tyr Leu Thr Trp Ala Leu
                    100                 105                 110

Ser Thr Pro Met Ile Leu Leu Ala Leu Gly Leu Leu Ala Gly Ser Asn
                    115                 120                 125

Ala Thr Lys Leu Phe Thr Ala Ile Thr Phe Asp Ile Ala Met Cys Val
            130                 135                 140

Thr Gly Leu Ala Ala Ala Leu Thr Thr Ser Ser His Leu Met Arg Trp
145                 150                 155                 160

Phe Trp Tyr Ala Ile Ser Cys Ala Cys Phe Leu Val Val Leu Tyr Ile
                        165                 170                 175

Leu Leu Val Glu Trp Ala Gln Asp Ala Lys Ala Ala Gly Thr Ala Asp
                    180                 185                 190

Met Phe Asn Thr Leu Lys Leu Leu Thr Val Val Met Trp Leu Gly Tyr
                    195                 200                 205

Pro Ile Val Trp Ala Leu Gly Val Glu Gly Ile Ala Val Leu Pro Val
                    210                 215                 220

Gly Val Thr Ser Trp Gly Tyr Ser Phe Leu Asp Ile Val Ala Lys Tyr
225                 230                 235                 240

Ile Phe Ala Phe Leu Leu Leu Asn Tyr Leu Thr Ser Asn Glu Ser Val
                    245                 250                 255

Val Ser Gly Ser Ile Leu Asp Val Pro Ser Ala Ser Gly Thr Pro Ala
                    260                 265                 270

Asp Asp Ala Ala Ala Lys Ser Arg Ile Thr Ser Glu Gly Glu Tyr Ile
                275                 280                 285

Pro Leu Asp Gln Ile Asp Ile Asn Phe Cys Tyr Glu Asn Glu Val
        290                 295                 300

<210> SEQ ID NO 37
<211> LENGTH: 365
<212> TYPE: PRT
<213> ORGANISM: Artificial sequence
<220> FEATURE:
<223> OTHER INFORMATION: Synthetic polypeptide

<400> SEQUENCE: 37

Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
                20                  25                  30

Glu Arg Arg Pro Pro Ser Glu Arg Asn Thr Pro Tyr Ala Asn Ile Lys
            35                  40                  45

Lys Val Pro Asn Ile Thr Glu Pro Asn Ala Asn Val Gln Leu Asp Gly
        50                  55                  60

Trp Ala Leu Tyr Gln Asp Phe Tyr Tyr Leu Ala Gly Ser Asp Lys Glu
65                  70                  75                  80

Trp Val Val Gly Pro Ser Asp Gln Cys Tyr Cys Arg Ala Trp Ser Lys
                    85                  90                  95

Ser His Gly Thr Asp Arg Glu Gly Glu Ala Ala Val Val Trp Ala Tyr
                100                 105                 110

Ile Val Phe Ala Ile Cys Ile Val Gln Leu Val Tyr Phe Met Phe Ala
            115                 120                 125

Ala Trp Lys Ala Thr Val Gly Trp Glu Glu Val Tyr Val Asn Ile Ile
```

```
                    130                 135                 140
Glu Leu Val His Ile Ala Leu Val Ile Trp Val Glu Phe Asp Lys Pro
145                 150                 155                 160

Ala Met Leu Tyr Leu Asn Asp Gly Gln Met Val Pro Trp Leu Arg Tyr
                165                 170                 175

Ser Ala Trp Leu Leu Ser Cys Pro Val Ile Leu Ile His Leu Ser Asn
            180                 185                 190

Leu Thr Gly Leu Lys Gly Asp Tyr Ser Lys Arg Thr Met Gly Leu Leu
        195                 200                 205

Val Ser Asp Ile Gly Thr Ile Val Phe Gly Thr Ser Ala Ala Leu Ala
    210                 215                 220

Pro Pro Asn His Val Lys Val Ile Leu Phe Thr Ile Gly Leu Leu Tyr
225                 230                 235                 240

Gly Leu Phe Thr Phe Phe Thr Ala Ala Lys Val Tyr Ile Glu Ala Tyr
                245                 250                 255

His Thr Val Pro Lys Gly Gln Cys Arg Asn Leu Val Arg Ala Met Ala
            260                 265                 270

Trp Thr Tyr Phe Val Ser Trp Ala Met Phe Pro Ile Leu Phe Ile Leu
        275                 280                 285

Gly Arg Glu Gly Phe Gly His Ile Thr Tyr Phe Gly Ser Ser Ile Gly
    290                 295                 300

His Phe Ile Leu Glu Ile Phe Ser Lys Asn Leu Trp Ser Leu Leu Gly
305                 310                 315                 320

His Gly Leu Arg Tyr Arg Ile Arg Gln His Ile Ile His Gly Asn
                325                 330                 335

Leu Thr Lys Lys Asn Lys Ile Asn Ile Ala Gly Asp Asn Val Glu Val
            340                 345                 350

Glu Glu Tyr Val Asp Ser Asn Asp Lys Asp Ser Asp Val
        355                 360                 365

<210> SEQ ID NO 38
<211> LENGTH: 395
<212> TYPE: PRT
<213> ORGANISM: Artificial sequence
<220> FEATURE:
<223> OTHER INFORMATION: Synthetic polypeptide

<400> SEQUENCE: 38

Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
            20                  25                  30

Glu Arg Arg Pro Pro Ser Glu Arg Asn Thr Pro Tyr Ala Asn Ile Lys
        35                  40                  45

Lys Val Pro Asn Ile Thr Glu Pro Asn Ala Asn Val Gln Leu Asp Gly
    50                  55                  60

Trp Ala Leu Tyr Gln Asp Phe Tyr Tyr Leu Ala Gly Ser Asp Lys Glu
65                  70                  75                  80

Trp Val Val Gly Pro Ser Asp Gln Cys Tyr Cys Arg Ala Trp Ser Lys
                85                  90                  95

Ser His Gly Thr Asp Arg Glu Gly Glu Ala Ala Val Val Trp Ala Tyr
            100                 105                 110

Ile Val Phe Ala Ile Cys Ile Val Gln Leu Val Tyr Phe Met Phe Ala
        115                 120                 125

Ala Trp Lys Ala Thr Val Gly Trp Glu Glu Val Tyr Val Asn Ile Ile
```

```
            130                 135                 140
    Glu Leu Val His Ile Ala Leu Val Ile Trp Val Glu Phe Asp Lys Pro
    145                 150                 155                 160

Ala Met Leu Tyr Leu Asn Asp Gly Gln Met Val Pro Trp Leu Arg Tyr
                    165                 170                 175

Ser Ala Trp Leu Leu Ser Cys Pro Val Ile Leu Ile His Leu Ser Asn
                    180                 185                 190

Leu Thr Gly Leu Lys Gly Asp Tyr Ser Lys Arg Thr Met Gly Leu Leu
                    195                 200                 205

Val Ser Asp Ile Gly Thr Ile Val Phe Gly Thr Ser Ala Ala Leu Ala
                    210                 215                 220

Pro Pro Asn His Val Lys Val Ile Leu Phe Thr Ile Gly Leu Leu Tyr
    225                 230                 235                 240

Gly Leu Phe Thr Phe Phe Thr Ala Ala Lys Val Tyr Ile Glu Ala Tyr
                    245                 250                 255

His Thr Val Pro Lys Gly Gln Cys Arg Asn Leu Val Arg Ala Met Ala
                    260                 265                 270

Trp Thr Tyr Phe Val Ser Trp Ala Met Phe Pro Ile Leu Phe Ile Leu
                    275                 280                 285

Gly Arg Glu Gly Phe Gly His Ile Thr Tyr Phe Gly Ser Ser Ile Gly
                    290                 295                 300

His Phe Ile Leu Glu Ile Phe Ser Lys Asn Leu Trp Ser Leu Leu Gly
    305                 310                 315                 320

His Gly Leu Arg Tyr Arg Ile Arg Gln His Ile Ile His Gly Asn
                    325                 330                 335

Leu Thr Lys Lys Asn Lys Ile Asn Ile Ala Gly Asp Asn Val Glu Val
                    340                 345                 350

Glu Glu Tyr Val Asp Ser Asn Asp Lys Asp Ser Asp Val Ala Ala Ala
                    355                 360                 365

Lys Ser Arg Ile Thr Ser Glu Gly Glu Tyr Ile Pro Leu Asp Gln Ile
                    370                 375                 380

Asp Ile Asn Val Phe Cys Tyr Glu Asn Glu Val
    385                 390                 395

<210> SEQ ID NO 39
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 39

Met Ser Arg Arg Pro Trp Leu Leu Ala Leu Ala Leu Ala Val Ala Leu
    1               5                   10                  15

Ala Ala Gly Ser Ala Gly Ala Ser Thr Gly Ser Asp Ala Thr Val Pro
                    20                  25                  30

Val Ala Thr Gln Asp Gly Pro Asp Tyr Val Phe His Arg Ala His Glu
                    35                  40                  45

Arg Met Leu Phe Gln Thr Ser Tyr Thr Leu Glu Asn Asn Gly Ser Val
                    50                  55                  60

Ile Cys Ile Pro Asn Asn Gly Gln Cys Phe Cys Leu Ala Trp Leu Lys
    65                  70                  75                  80

Ser Asn Gly Thr Asn Ala Glu Lys Leu Ala Ala Asn Ile Leu Gln Trp
                    85                  90                  95

Ile Ser Phe Ala Leu Ser Ala Leu Cys Leu Met Phe Tyr Gly Tyr Gln
```

```
              100                 105                 110
Thr Trp Lys Ser Thr Cys Gly Trp Glu Glu Ile Tyr Val Ala Thr Ile
            115                 120                 125
Ser Met Ile Lys Phe Ile Ile Glu Tyr Phe His Ser Phe Asp Glu Pro
            130                 135                 140
Ala Val Ile Tyr Ser Ser Asn Gly Asn Lys Thr Lys Trp Leu Arg Tyr
145                 150                 155                 160
Ala Ser Trp Leu Leu Thr Cys Pro Val Ile Leu Ile Arg Leu Ser Asn
                165                 170                 175
Leu Thr Gly Leu Ala Asn Asp Tyr Asn Lys Arg Thr Met Gly Leu Leu
                180                 185                 190
Val Ser Asp Ile Gly Thr Ile Val Trp Gly Thr Thr Ala Ala Leu Ser
            195                 200                 205
Lys Gly Tyr Val Arg Val Ile Phe Phe Leu Met Gly Leu Cys Tyr Gly
            210                 215                 220
Ile Tyr Thr Phe Phe Asn Ala Ala Lys Val Tyr Ile Glu Ala Tyr His
225                 230                 235                 240
Thr Val Pro Lys Gly Arg Cys Arg Gln Val Val Thr Gly Met Ala Trp
                245                 250                 255
Leu Phe Phe Val Ser Trp Gly Met Phe Pro Ile Leu Phe Ile Leu Gly
                260                 265                 270
Pro Glu Gly Phe Gly Val Leu Ser Lys Tyr Gly Ser Asn Val Gly His
            275                 280                 285
Thr Ile Ile Asp Leu Met Ser Lys Gln Cys Trp Gly Leu Leu Gly His
            290                 295                 300
Tyr Leu Arg Val Leu Ile His Glu His Ile Leu Ile His Gly Asp Ile
305                 310                 315                 320
Arg Lys Thr Thr Lys Leu Asn Ile Gly Gly Thr Glu Ile Glu Val Glu
                325                 330                 335
Thr Leu Val Glu Asp Glu Ala Glu Ala Gly Ala Val
                340                 345

<210> SEQ ID NO 40
<211> LENGTH: 378
<212> TYPE: PRT
<213> ORGANISM: Artificial sequence
<220> FEATURE:
<223> OTHER INFORMATION: Synthetic polypeptide

<400> SEQUENCE: 40

Met Ser Arg Arg Pro Trp Leu Leu Ala Leu Ala Leu Ala Val Ala Leu
1               5                   10                  15
Ala Ala Gly Ser Ala Gly Ala Ser Thr Gly Ser Asp Ala Thr Val Pro
                20                  25                  30
Val Ala Thr Gln Asp Gly Pro Asp Tyr Val Phe His Arg Ala His Glu
            35                  40                  45
Arg Met Leu Phe Gln Thr Ser Tyr Thr Leu Glu Asn Asn Gly Ser Val
        50                  55                  60
Ile Cys Ile Pro Asn Asn Gly Gln Cys Phe Cys Leu Ala Trp Leu Lys
65                  70                  75                  80
Ser Asn Gly Thr Asn Ala Glu Lys Leu Ala Ala Asn Ile Leu Gln Trp
                85                  90                  95
Ile Ser Phe Ala Leu Ser Ala Leu Cys Leu Met Phe Tyr Gly Tyr Gln
                100                 105                 110
Thr Trp Lys Ser Thr Cys Gly Trp Glu Glu Ile Tyr Val Ala Thr Ile
```

```
                        115                 120                 125
Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Ile Leu Arg Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

Thr Ile Ile Asp Leu Met Ser Lys Gln Cys Trp Gly Leu Leu Gly His
    290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val Ala Ala Ala Lys
            340                 345                 350

Ser Arg Ile Thr Ser Glu Gly Glu Tyr Ile Pro Leu Asp Gln Ile Asp
        355                 360                 365

Ile Asn Val Phe Cys Tyr Glu Asn Glu Val
    370                 375

<210> SEQ ID NO 41
<211> LENGTH: 348
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (167)..(167)
<223> OTHER INFORMATION: Xaa can be any naturally occurring amino acid

<400> SEQUENCE: 41

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80
```

```
Ser Asn Gly Thr Asn Ala Glu Lys Leu Ala Asn Ile Leu Gln Trp
            85                  90                  95

Ile Ser Phe Ala Leu Ser Ala Leu Cys Leu Met Phe Tyr Gly Tyr Gln
        100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
        130                 135                 140

Ala Val Ile Tyr Ser Ser Asn Gly Asn Lys Thr Lys Trp Leu Arg Tyr
145                 150                 155                 160

Ala Ser Trp Leu Leu Thr Xaa Pro Val Ile Leu Ile Arg Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
        210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

Thr Ile Ile Asp Leu Met Ser Lys Gln Cys Trp Gly Leu Leu Gly His
        290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 42
<211> LENGTH: 378
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (167)..(167)
<223> OTHER INFORMATION: Xaa is any amino acid.

<400> SEQUENCE: 42

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80
```

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
                115                 120                 125

Ser Met Ile Lys Phe Ile Ile Glu Tyr Phe His Ser Phe Asp Glu Pro
                130                 135                 140

Ala Val Ile Tyr Ser Ser Asn Gly Asn Lys Thr Lys Trp Leu Arg Tyr
145                 150                 155                 160

Ala Ser Trp Leu Leu Thr Xaa Pro Val Ile Leu Ile Arg Leu Ser Asn
                165                 170                 175

Leu Thr Gly Leu Ala Asn Asp Tyr Asn Lys Arg Thr Met Gly Leu Leu
                180                 185                 190

Val Ser Asp Ile Gly Thr Ile Val Trp Gly Thr Thr Ala Ala Leu Ser
                195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
                260                 265                 270

Pro Glu Gly Phe Gly Val Leu Ser Lys Tyr Gly Ser Asn Val Gly His
                275                 280                 285

Thr Ile Ile Asp Leu Met Ser Lys Gln Cys Trp Gly Leu Leu Gly His
                290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val Ala Ala Ala Lys
                340                 345                 350

Ser Arg Ile Thr Ser Glu Gly Glu Tyr Ile Pro Leu Asp Gln Ile Asp
                355                 360                 365

Ile Asn Val Phe Cys Tyr Glu Asn Glu Val
                370                 375

<210> SEQ ID NO 43
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 43

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Ile Ser Phe Ala Leu Ser Ala
50                  55                  60

```
Leu Cys Leu Met Phe Tyr Gly Tyr Gln Thr Trp Lys Ser Thr Cys Gly
 65                  70                  75                  80

Trp Glu Glu Ile Tyr Val Ala Thr Ile Ser Met Ile Lys Phe Ile Ile
                 85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Cys
        115                 120                 125

Pro Val Ile Leu Ile Arg Leu Ser Asn Leu Thr Gly Leu Ala Asn Asp
130                 135                 140

Tyr Asn Lys Arg Thr Met Gly Leu Leu Val Ser Asp Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
            180                 185                 190

Ala Lys Val Tyr Ile Glu Ala Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val
305

<210> SEQ ID NO 44
<211> LENGTH: 339
<212> TYPE: PRT
<213> ORGANISM: Artificial sequence
<220> FEATURE:
<223> OTHER INFORMATION: Synthetic polypeptide

<400> SEQUENCE: 44

Met Asp Tyr Gly Gly Ala Leu Ser Ala Val Gly Leu Phe Gln Thr Ser
 1               5                  10                  15

Tyr Thr Leu Glu Asn Asn Gly Ser Val Ile Cys Ile Pro Asn Asn Gly
                 20                  25                  30

Gln Cys Phe Cys Leu Ala Trp Leu Lys Ser Asn Gly Thr Asn Ala Glu
             35                  40                  45

Lys Leu Ala Ala Asn Ile Leu Gln Trp Ile Ser Phe Ala Leu Ser Ala
         50                  55                  60

Leu Cys Leu Met Phe Tyr Gly Tyr Gln Thr Trp Lys Ser Thr Cys Gly
 65                  70                  75                  80

Trp Glu Glu Ile Tyr Val Ala Thr Ile Ser Met Ile Lys Phe Ile Ile
                 85                  90                  95

Glu Tyr Phe His Ser Phe Asp Glu Pro Ala Val Ile Tyr Ser Ser Asn
            100                 105                 110
```

Gly Asn Lys Thr Lys Trp Leu Arg Tyr Ala Ser Trp Leu Leu Thr Cys
            115                 120                 125

Pro Val Ile Leu Ile Arg Leu Ser Asn Leu Thr Gly Leu Ala Asn Asp
            130                 135                 140

Tyr Asn Lys Arg Thr Met Gly Leu Leu Val Ser Asp Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
                180                 185                 190

Ala Lys Val Tyr Ile Glu Ala Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Ala Ala Lys Ser Arg Ile Thr Ser Glu Gly
305                 310                 315                 320

Glu Tyr Ile Pro Leu Asp Gln Ile Asp Ile Asn Val Phe Cys Tyr Glu
            325                 330                 335

Asn Glu Val

<210> SEQ ID NO 45
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 45

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ser Ala Gly Phe Ser Ile
            50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Ser Met Val Lys Val Ile Leu
                85                  90                  95

Glu Phe Phe Phe Ser Phe Lys Asn Pro Ser Met Leu Tyr Leu Ala Thr
                100                 105                 110

Gly His Arg Val Lys Trp Leu Arg Tyr Ala Ser Trp Leu Leu Thr Cys
            115                 120                 125

Pro Val Ile Leu Ile Arg Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 46
<211> LENGTH: 340
<212> TYPE: PRT
<213> ORGANISM: Artificial sequence
<220> FEATURE:
<223> OTHER INFORMATION: Synthetic polypeptide

<400> SEQUENCE: 46

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ser Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Ser Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Lys Trp Leu Arg Tyr Ala Ser Trp Leu Leu Thr Cys
        115                 120                 125

Pro Val Ile Leu Ile Arg Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

```
Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro Ala Ala Lys Ser Arg Ile Thr Ser Glu
305                 310                 315                 320

Gly Glu Tyr Ile Pro Leu Asp Gln Ile Asp Ile Asn Val Phe Cys Tyr
                325                 330                 335

Glu Asn Glu Val
            340

<210> SEQ ID NO 47
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 47

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Leu Leu Ile Arg Leu Ser Asn
                165                 170                 175

Leu Thr Gly Leu Lys Asp Asp Tyr Ser Lys Arg Thr Met Gly Leu Leu
            180                 185                 190
```

```
Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
        260                 265                 270

Thr Glu Gly Phe Gly His Ile Ser Lys Tyr Gly Ser Asn Ile Gly His
        275                 280                 285

Ser Ile Leu Asp Leu Ile Ala Lys Gln Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
            325                 330                 335

Thr Leu Val Ala Glu Glu Glu Asp
            340

<210> SEQ ID NO 48
<211> LENGTH: 374
<212> TYPE: PRT
<213> ORGANISM: Artificial sequence
<220> FEATURE:
<223> OTHER INFORMATION: Synthetic polypeptide

<400> SEQUENCE: 48

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Leu Leu Ile Arg Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205
```

```
Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Lys Tyr Gly Ser Asn Ile Gly His
                275                 280                 285

Ser Ile Leu Asp Leu Ile Ala Lys Gln Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp Ala Ala Lys Ser Arg Ile Thr
                340                 345                 350

Ser Glu Gly Glu Tyr Ile Pro Leu Asp Gln Ile Asp Ile Asn Val Phe
                355                 360                 365

Cys Tyr Glu Asn Glu Val
370

<210> SEQ ID NO 49
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 49

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Ile Ser Phe Ala Leu Ser Ala
50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
                100                 105                 110

Gly Asn Lys Thr Lys Trp Leu Arg Tyr Ala Ser Trp Leu Leu Thr Cys
            115                 120                 125

Pro Val Leu Leu Ile Arg Leu Ser Asn Leu Thr Gly Leu Lys Asp Asp
            130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
                180                 185                 190
```

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220

Met Phe Pro Val Leu Phe Leu Leu Gly Thr Glu Gly Phe Gly His Ile
225                 230                 235                 240

Ser Lys Tyr Gly Ser Asn Ile Gly His Ser Ile Leu Asp Leu Ile Ala
            245                 250                 255

Lys Gln Met Trp Gly Val Leu Gly Asn Tyr Leu Arg Val Lys Ile His
                260                 265                 270

Glu His Ile Leu Leu Tyr Gly Asp Ile Arg Lys Gln Lys Ile Thr
        275                 280                 285

Ile Ala Gly Gln Glu Met Glu Val Glu Thr Leu Val Ala Glu Glu Glu
    290                 295                 300

Asp
305

<210> SEQ ID NO 50
<211> LENGTH: 335
<212> TYPE: PRT
<213> ORGANISM: Artificial sequence
<220> FEATURE:
<223> OTHER INFORMATION: Synthetic polypeptide

<400> SEQUENCE: 50

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Cys
        115                 120                 125

Pro Val Leu Leu Ile Arg Leu Ser Asn Leu Thr Gly Leu Lys Asp Asp
    130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220

Met Phe Pro Val Leu Phe Leu Leu Gly Thr Glu Gly Phe Gly His Ile
225                 230                 235                 240

```
Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Gln Lys Ile Thr
            275                 280                 285

Ile Ala Gly Gln Glu Met Glu Val Glu Thr Leu Val Ala Glu Glu Glu
            290                 295                 300

Asp Ala Ala Ala Lys Ser Arg Ile Thr Ser Glu Gly Glu Tyr Ile Pro
305                 310                 315                 320

Leu Asp Gln Ile Asp Ile Asn Val Phe Cys Tyr Glu Asn Glu Val
                325                 330                 335

<210> SEQ ID NO 51
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 51

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
            115                 120                 125

Ile Ser Met Met Lys Ser Ile Ile Glu Ala Phe His Ser Phe Asp Ser
130                 135                 140

Pro Ala Thr Leu Trp Leu Ser Ser Gly Asn Gly Val Lys Trp Met Arg
145                 150                 155                 160

Tyr Gly Ser Trp Leu Leu Thr Cys Pro Val Ile Leu Ile Arg Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
            195                 200                 205

Cys Thr Gly Trp Thr Lys Ile Leu Phe Phe Leu Ile Ser Leu Ser Tyr
    210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270
```

```
Gly Pro Glu Gly Phe Gly His Ile Ser Lys Tyr Gly Ser Asn Ile Gly
            275                 280                 285

His Ser Ile Leu Asp Leu Ile Ala Lys Gln Met Trp Gly Val Leu Gly
    290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350
```

<210> SEQ ID NO 52
<211> LENGTH: 380
<212> TYPE: PRT
<213> ORGANISM: Artificial sequence
<220> FEATURE:
<223> OTHER INFORMATION: Synthetic polypeptide

<400> SEQUENCE: 52

```
Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Ser Met Met Lys Ser Ile Ile Glu Ala Phe His Ser Phe Asp Ser
    130                 135                 140

Pro Ala Thr Leu Trp Leu Ser Ser Gly Asn Gly Val Lys Trp Met Arg
145                 150                 155                 160

Tyr Gly Ser Trp Leu Leu Thr Cys Pro Val Ile Leu Ile Arg Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
    210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Lys Tyr Gly Ser Asn Ile Gly
        275                 280                 285
```

```
His Ser Ile Leu Asp Leu Ile Ala Lys Gln Met Trp Gly Val Leu Gly
    290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser Ala Ala
            340                 345                 350

Ala Lys Ser Arg Ile Thr Ser Glu Gly Tyr Ile Pro Leu Asp Gln
                355                 360                 365

Ile Asp Ile Asn Val Phe Cys Tyr Glu Asn Glu Val
370                 375                 380

<210> SEQ ID NO 53
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 53

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Val Ser Phe Ala Leu Ser Val
50                  55                  60

Ala Cys Leu Gly Trp Tyr Ala Tyr Gln Ala Trp Arg Ala Thr Cys Gly
65                  70                  75                  80

Trp Glu Glu Val Tyr Val Ala Leu Ile Ser Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Lys Trp Met Arg Tyr Gly Ser Trp Leu Leu Thr Cys
        115                 120                 125

Pro Val Ile Leu Ile Arg Leu Ser Asn Leu Thr Gly Leu Lys Asp Asp
130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
210                 215                 220

Met Phe Pro Val Leu Phe Leu Gly Pro Glu Gly Phe Gly His Ile
225                 230                 235                 240

Ser Lys Tyr Gly Ser Asn Ile Gly His Ser Ile Leu Asp Leu Ile Ala
            245                 250                 255

Lys Gln Met Trp Gly Val Leu Gly Asn Tyr Leu Arg Val Lys Ile His
        260                 265                 270
```

```
Glu His Ile Leu Leu Tyr Gly Asp Ile Arg Lys Lys Gln Lys Ile Thr
            275                 280                 285
Ile Ala Gly Gln Glu Met Glu Val Glu Thr Leu Val Ala Glu Glu Glu
        290                 295                 300
Asp Lys Tyr Glu Ser Ser
305                 310
```

<210> SEQ ID NO 54
<211> LENGTH: 340
<212> TYPE: PRT
<213> ORGANISM: Artificial sequence
<220> FEATURE:
<223> OTHER INFORMATION: Synthetic polypeptide

<400> SEQUENCE: 54

```
Met Asp Tyr Gly Gly Ala Leu Ser Ala Val Gly Leu Phe Gln Thr Ser
1               5                   10                  15
Tyr Thr Leu Glu Asn Asn Gly Ser Val Ile Cys Ile Pro Asn Asn Gly
            20                  25                  30
Gln Cys Phe Cys Leu Ala Trp Leu Lys Ser Asn Gly Thr Asn Ala Glu
        35                  40                  45
Lys Leu Ala Ala Asn Ile Leu Gln Trp Val Ser Phe Ala Leu Ser Val
    50                  55                  60
Ala Cys Leu Gly Trp Tyr Ala Tyr Gln Ala Trp Arg Ala Thr Cys Gly
65                  70                  75                  80
Trp Glu Glu Val Tyr Val Ala Leu Ile Ser Met Met Lys Ser Ile Ile
                85                  90                  95
Glu Ala Phe His Ser Phe Asp Ser Pro Ala Thr Leu Trp Leu Ser Ser
            100                 105                 110
Gly Asn Gly Val Lys Trp Met Arg Tyr Gly Ser Trp Leu Leu Thr Cys
        115                 120                 125
Pro Val Ile Leu Ile Arg Leu Ser Asn Leu Thr Gly Leu Lys Asp Asp
    130                 135                 140
Tyr Ser Lys Arg Thr Met Gly Leu Leu Val Ser Asp Val Gly Cys Ile
145                 150                 155                 160
Val Trp Gly Ala Thr Ser Ala Met Cys Thr Gly Trp Thr Lys Ile Leu
                165                 170                 175
Phe Phe Leu Ile Ser Leu Ser Tyr Gly Met Tyr Thr Tyr Phe His Ala
            180                 185                 190
Ala Lys Val Tyr Ile Glu Ala Phe His Thr Val Pro Lys Gly Leu Cys
        195                 200                 205
Arg Gln Leu Val Arg Ala Met Ala Trp Leu Phe Phe Val Ser Trp Gly
    210                 215                 220
Met Phe Pro Val Leu Phe Leu Leu Gly Pro Glu Gly Phe Gly His Ile
225                 230                 235                 240
Ser Lys Tyr Gly Ser Asn Ile Gly His Ser Ile Leu Asp Leu Ile Ala
                245                 250                 255
Lys Gln Met Trp Gly Val Leu Gly Asn Tyr Leu Arg Val Lys Ile His
            260                 265                 270
Glu His Ile Leu Leu Tyr Gly Asp Ile Arg Lys Lys Gln Lys Ile Thr
        275                 280                 285
Ile Ala Gly Gln Glu Met Glu Val Glu Thr Leu Val Ala Glu Glu Glu
    290                 295                 300
Asp Lys Tyr Glu Ser Ser Ala Ala Lys Ser Arg Ile Thr Ser Glu
305                 310                 315                 320
```

Gly Glu Tyr Ile Pro Leu Asp Gln Ile Asp Ile Asn Val Phe Cys Tyr
                325                 330                 335

Glu Asn Glu Val
            340

<210> SEQ ID NO 55
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 55

Met Asp Tyr Gly Gly Ala Leu Ser Ala Val Gly
1               5                   10

<210> SEQ ID NO 56
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 56

Lys Ser Arg Ile Thr Ser Glu Gly Glu Tyr Ile Pro Leu Asp Gln Ile
1               5                   10                  15

Asp Ile Asn Val
            20

<210> SEQ ID NO 57
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 57

Val Lys Glu Ser Leu
1               5

<210> SEQ ID NO 58
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 58

Val Leu Gly Ser Leu
1               5

<210> SEQ ID NO 59
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 59

Asn Ala Asn Ser Phe Cys Tyr Glu Asn Glu Val Ala Leu Thr Ser Lys
1               5                   10                  15

<210> SEQ ID NO 60
<211> LENGTH: 6
<212> TYPE: PRT
<213> ORGANISM: Artificial sequence

```
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa is any amino acid.

<400> SEQUENCE: 60

Phe Xaa Tyr Glu Asn Glu
1               5

<210> SEQ ID NO 61
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 61

Phe Cys Tyr Glu Asn Glu Val
1               5

<210> SEQ ID NO 62
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 62

Met Asp Tyr Gly Gly Ala Leu Ser Ala Val Gly Arg Glu Leu Leu Phe
1               5                   10                  15

Val Thr Asn Pro Val Val Val Asn Gly Ser
            20                  25

<210> SEQ ID NO 63
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 63

Met Ala Gly His Ser Asn Ser Met Ala Leu Phe Ser Phe Ser Leu Leu
1               5                   10                  15

Trp Leu Cys Ser Gly Val Leu Gly Thr Glu Phe
            20                  25

<210> SEQ ID NO 64
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 64

Met Gly Leu Arg Ala Leu Met Leu Trp Leu Leu Ala Ala Ala Gly Leu
1               5                   10                  15

Val Arg Glu Ser Leu Gln Gly
            20

<210> SEQ ID NO 65
<211> LENGTH: 18
<212> TYPE: PRT
<213> ORGANISM: Artificial sequence
<220> FEATURE:
```

```
<223> OTHER INFORMATION: Synthetic polypeptide

<400> SEQUENCE: 65

Met Arg Gly Thr Pro Leu Leu Leu Val Val Ser Leu Phe Ser Leu Leu
1               5                   10                  15

Gln Asp

<210> SEQ ID NO 66
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 66

Met Thr Glu Thr Leu Pro Pro Val Thr Glu Ser Ala Val Ala Leu Gln
1               5                   10                  15

Ala Glu
```